(12) United States Patent (10) Patent No.: US 8,372,152 B2
Kirschman (45) Date of Patent: Feb. 12, 2013

(54) SPINAL FUSION SYSTEM UTILIZING AN IMPLANT PLATE HAVING AT LEAST ONE INTEGRAL LOCK AND RATCHET LOCK

(75) Inventor: David Louis Kirschman, Dayton, OH (US)

(73) Assignee: X-spine Systems, Inc., Miamisburg, OH (US)

( * ) Notice: Subject to any disclaimer, the term of this patent is extended or adjusted under 35 U.S.C. 154(b) by 1334 days.

(21) Appl. No.: 11/778,270

(22) Filed: Jul. 16, 2007

(65) Prior Publication Data

US 2008/0021476 A1 Jan. 24, 2008

Related U.S. Application Data

(63) Continuation-in-part of application No. 11/379,301, filed on Apr. 19, 2006, which is a continuation-in-part of application No. 10/858,629, filed on Jun. 2, 2004, now Pat. No. 7,641,701, which is a continuation-in-part of application No. 10/675,361, filed on Sep. 30, 2003, now Pat. No. 7,182,782.

(51) Int. Cl.
*A61F 2/44* (2006.01)
*A61B 17/80* (2006.01)
(52) U.S. Cl. ............. 623/17.16; 606/289; 606/293; 606/295
(58) Field of Classification Search .......... 606/70–71, 606/280–299; 623/17.11–17.16
See application file for complete search history.

(56) References Cited

U.S. PATENT DOCUMENTS

| | | |
|---|---|---|
| 1,025,008 A | 4/1912 | Miner |
| 2,677,369 A | 5/1954 | Knowles |
| 3,848,601 A | 11/1974 | Ma et al. |
| 3,867,728 A | 2/1975 | Stubstad et al. |
| 4,157,715 A | 6/1979 | Westerhoff |
| 4,309,777 A | 1/1982 | Patil |
| 4,349,921 A | 9/1982 | Kuntz |
| 4,488,543 A | 12/1984 | Tornier |
| 4,553,273 A | 11/1985 | Wu |
| 4,599,086 A | 7/1986 | Doty |
| 4,611,581 A | 9/1986 | Steffee |
| 4,696,290 A | 9/1987 | Steffee |
| 4,714,469 A | 12/1987 | Kenna |
| 4,743,256 A | 5/1988 | Brantigan |
| 4,759,766 A | 7/1988 | Buettner-Janz et al. |
| 4,834,757 A | 5/1989 | Brantigan |
| 4,878,915 A | 11/1989 | Brantigan |
| 4,904,261 A | 2/1990 | Dove et al. |
| 4,988,349 A | 1/1991 | Pennig |
| 4,997,432 A | 3/1991 | Keller |
| 5,041,113 A | 8/1991 | Biedermann et al. |
| 5,084,049 A | 1/1992 | Asher et al. |
| 5,085,660 A | 2/1992 | Lin |
| 5,192,327 A | 3/1993 | Brantigan |
| 5,246,443 A | 9/1993 | Mai |
| 5,261,911 A | 11/1993 | Carl |
| 5,275,601 A | 1/1994 | Gogolewski et al. |
| 5,290,312 A | 3/1994 | Kojimoto et al. |

(Continued)

FOREIGN PATENT DOCUMENTS

| | | |
|---|---|---|
| CA | 1292596 | 12/1991 |
| CA | 2133276 | 4/1995 |

(Continued)

*Primary Examiner* — Thomas C. Barrett
*Assistant Examiner* — Matthew Lawson
(74) *Attorney, Agent, or Firm* — Jacox, Meckstroth & Jenkins

(57) ABSTRACT

Spinal fusion system and method utilizing an implant plate and screw, wherein at least one pawl is mounted on or integral with at least one of said plate and becomes operatively related to the screw after the screw is inserted in the implant plate to prevent the screw from moving in at least one of an axial direction or a rotational direction. Other features and embodiments are described and claimed.

66 Claims, 27 Drawing Sheets

U.S. PATENT DOCUMENTS

| | | | |
|---|---|---|---|
| 5,324,290 A | 6/1994 | Zdeblick et al. |
| 5,330,473 A | 7/1994 | Howland |
| 5,364,399 A | 11/1994 | Lowery et al. |
| 5,405,391 A | 4/1995 | Hednerson et al. |
| 5,425,772 A | 6/1995 | Brantigan |
| 5,439,463 A | 8/1995 | Lin |
| 5,549,612 A | 8/1996 | Yapp et al. |
| 5,554,191 A | 9/1996 | Lahille et al. |
| 5,601,551 A | 2/1997 | Taylor et al. |
| 5,601,553 A | 2/1997 | Trebing et al. |
| 5,609,637 A | 3/1997 | Biedermann et al. |
| 5,616,142 A | 4/1997 | Yuan et al. |
| 5,616,144 A | 4/1997 | Yapp et al. |
| 5,620,443 A | 4/1997 | Gertzbein et al. |
| 5,672,177 A | 9/1997 | Seldin |
| 5,681,310 A | 10/1997 | Yuan et al. |
| 5,681,311 A | 10/1997 | Foley et al. |
| 5,702,395 A | 12/1997 | Hopf |
| 5,713,899 A | 2/1998 | Marnay et al. |
| 5,713,900 A | 2/1998 | Benzel et al. |
| 5,716,415 A | 2/1998 | Steffee |
| 5,720,746 A | 2/1998 | Soubeiran |
| 5,776,196 A | 7/1998 | Matsuzaki et al. |
| 5,843,082 A | 12/1998 | Yuan et al. |
| 5,876,402 A | 3/1999 | Errico et al. |
| 5,888,228 A | 3/1999 | Knothe et al. |
| 5,904,683 A | 5/1999 | Pohndorf et al. |
| 5,925,047 A | 7/1999 | Errico et al. |
| 5,951,558 A | 9/1999 | Fiz |
| 5,954,722 A | 9/1999 | Bono |
| 6,030,389 A | 2/2000 | Wagner et al. |
| 6,066,175 A | 5/2000 | Henderson et al. |
| 6,106,557 A | 8/2000 | Robioneck et al. |
| 6,136,002 A | 10/2000 | Shih et al. |
| 6,139,550 A | 10/2000 | Michelson |
| 6,152,927 A | 11/2000 | Farris et al. |
| 6,159,211 A | 12/2000 | Boriani et al. |
| 6,159,213 A | 12/2000 | Rogozinski |
| 6,159,245 A | 12/2000 | Meriwether et al. |
| 6,171,307 B1 | 1/2001 | Orlich |
| 6,193,721 B1 | 2/2001 | Michelson |
| D440,311 S | 4/2001 | Michelson |
| 6,224,602 B1 | 5/2001 | Hayes |
| 6,235,033 B1 | 5/2001 | Brace et al. |
| 6,235,034 B1 | 5/2001 | Bray |
| 6,235,059 B1 | 5/2001 | Benezech et al. |
| 6,245,108 B1 | 6/2001 | Biscup |
| 6,258,089 B1 * | 7/2001 | Campbell et al. ........... 606/86 B |
| 6,261,291 B1 | 7/2001 | Talaber et al. |
| 6,261,586 B1 | 7/2001 | McKay |
| 6,264,655 B1 | 7/2001 | Pisharodi |
| 6,293,949 B1 | 9/2001 | Justis et al. |
| D449,692 S | 10/2001 | Michelson |
| 6,306,136 B1 | 10/2001 | Baccelli |
| 6,306,139 B1 | 10/2001 | Fuentes |
| 6,328,738 B1 | 12/2001 | Suddaby |
| 6,361,537 B1 * | 3/2002 | Anderson ................... 606/86 B |
| 6,368,351 B1 | 4/2002 | Glenn et al. |
| 6,371,986 B1 | 4/2002 | Bagby |
| 6,383,186 B1 | 5/2002 | Michelson |
| 6,398,783 B1 | 6/2002 | Michelson |
| 6,413,259 B1 | 7/2002 | Lyons et al. |
| 6,416,528 B1 | 7/2002 | Michelson |
| 6,428,542 B1 | 8/2002 | Michelson |
| 6,432,106 B1 | 8/2002 | Fraser |
| 6,454,769 B2 | 9/2002 | Wagner et al. |
| 6,454,771 B1 | 9/2002 | Michelson |
| 6,485,517 B1 | 11/2002 | Michelson |
| 6,503,250 B2 | 1/2003 | Paul |
| 6,527,776 B1 | 3/2003 | Michelson |
| 6,533,786 B1 | 3/2003 | Needham et al. |
| 6,558,423 B1 | 5/2003 | Michelson |
| 6,558,424 B2 | 5/2003 | Thalgott |
| 6,569,201 B2 | 5/2003 | Moumene et al. |
| 6,572,619 B2 | 6/2003 | Santilli |
| 6,575,975 B2 | 6/2003 | Brace et al. |
| 6,592,586 B1 | 7/2003 | Michelson |
| 6,599,290 B2 | 7/2003 | Bailey et al. |
| 6,602,256 B1 | 8/2003 | Hayes |
| 6,602,257 B1 | 8/2003 | Thramann |
| 6,605,090 B1 | 8/2003 | Trieu et al. |
| 6,613,053 B1 | 9/2003 | Collins et al. |
| 6,616,666 B1 | 9/2003 | Michelson |
| 6,620,163 B1 | 9/2003 | Michelson |
| 6,626,907 B2 | 9/2003 | Campbell et al. |
| 6,652,525 B1 | 11/2003 | Assaker et al. |
| 6,669,700 B1 | 12/2003 | Farris et al. |
| 6,676,703 B2 | 1/2004 | Biscup |
| 6,679,883 B2 | 1/2004 | Hawkes et al. |
| 6,699,249 B2 | 3/2004 | Schlapfer et al. |
| 6,712,818 B1 | 3/2004 | Michelson |
| 6,730,127 B2 | 5/2004 | Michelson |
| 6,755,833 B1 | 6/2004 | Paul et al. |
| 6,776,781 B1 * | 8/2004 | Uwaydah ....................... 606/279 |
| 6,776,798 B2 | 8/2004 | Camino et al. |
| 6,837,905 B1 | 1/2005 | Lieberman |
| 6,852,113 B2 * | 2/2005 | Nathanson et al. ............. 606/71 |
| 6,890,334 B2 | 5/2005 | Brace et al. |
| 6,916,320 B2 | 7/2005 | Michelson |
| 6,926,737 B2 | 8/2005 | Jackson |
| 6,936,050 B2 | 8/2005 | Michelson |
| 6,936,051 B2 | 8/2005 | Michelson |
| 6,964,664 B2 | 11/2005 | Freid et al. |
| 6,969,390 B2 | 11/2005 | Michelson |
| 7,001,387 B2 | 2/2006 | Farris et al. |
| 7,033,394 B2 | 4/2006 | Michelson |
| 7,041,105 B2 | 5/2006 | Michelson |
| 7,041,135 B2 | 5/2006 | Michelson |
| 7,044,952 B2 | 5/2006 | Michelson |
| 7,163,561 B2 | 1/2007 | Michelson |
| 7,182,782 B2 | 2/2007 | Kirschman |
| 7,311,712 B2 | 12/2007 | Dalton |
| 7,445,627 B2 | 11/2008 | Hawkes et al. |
| 7,662,154 B2 * | 2/2010 | Ribeiro ........................... 606/70 |
| 7,699,880 B2 | 4/2010 | Orbay et al. |
| 7,780,708 B2 | 8/2010 | Morris et al. |
| 8,088,163 B1 | 1/2012 | Kleiner |
| 2002/0004683 A1 | 1/2002 | Michelson |
| 2002/0045898 A1 | 4/2002 | Freid et al. |
| 2002/0058939 A1 | 5/2002 | Wagner et al. |
| 2002/0120273 A1 | 8/2002 | Needham et al. |
| 2002/0143400 A1 | 10/2002 | Biscup |
| 2002/0173790 A1 | 11/2002 | Chang et al. |
| 2002/0183755 A1 | 12/2002 | Michelson |
| 2002/0183756 A1 | 12/2002 | Michelson |
| 2002/0183757 A1 | 12/2002 | Michelson |
| 2002/0188296 A1 | 12/2002 | Michelson |
| 2003/0018335 A1 | 1/2003 | Michelson |
| 2003/0023307 A1 | 1/2003 | Michelson |
| 2003/0045880 A1 | 3/2003 | Michelson |
| 2003/0060828 A1 | 3/2003 | Michelson |
| 2003/0078668 A1 | 4/2003 | Michelson |
| 2003/0093082 A1 | 5/2003 | Campbell et al. |
| 2003/0105462 A1 | 6/2003 | Haider |
| 2003/0181912 A1 | 9/2003 | Michelson |
| 2003/0187443 A1 | 10/2003 | Lauryssen et al. |
| 2003/0191471 A1 | 10/2003 | Michelson |
| 2003/0191472 A1 | 10/2003 | Michelson |
| 2003/0199876 A1 | 10/2003 | Brace et al. |
| 2003/0199983 A1 | 10/2003 | Michelson |
| 2003/0208204 A1 | 11/2003 | Bailey et al. |
| 2003/0225409 A1 | 12/2003 | Freid et al. |
| 2004/0019353 A1 | 1/2004 | Freid et al. |
| 2004/0030338 A1 | 2/2004 | Paul |
| 2004/0092939 A1 | 5/2004 | Freid et al. |
| 2004/0097934 A1 | 5/2004 | Farris et al. |
| 2004/0122426 A1 | 6/2004 | Michelson |
| 2004/0127896 A1 | 7/2004 | Lombardo et al. |
| 2004/0127897 A1 | 7/2004 | Freid et al. |
| 2004/0127903 A1 | 7/2004 | Schlapfer et al. |
| 2004/0133205 A1 | 7/2004 | Thramann et al. |
| 2004/0181226 A1 | 9/2004 | Michelson |
| 2004/0181229 A1 | 9/2004 | Michelson |
| 2004/0186476 A1 | 9/2004 | Michelson |
| 2004/0193269 A1 | 9/2004 | Fraser et al. |
| 2004/0193270 A1 | 9/2004 | DiMauro et al. |
| 2004/0193271 A1 | 9/2004 | Fraser et al. |

| | | | | | | | |
|---|---|---|---|---|---|---|---|
| 2004/0199254 | A1 | 10/2004 | Louis et al. | DE | 4409833 | A1 | 10/1995 |
| 2004/0210313 | A1 | 10/2004 | Michelson | EP | 0179695 | A1 | 4/1986 |
| 2004/0210314 | A1 | 10/2004 | Michelson | EP | 0307241 | A2 | 3/1989 |
| 2004/0230309 | A1 | 11/2004 | DiMauro et al. | EP | 599640 | A1 | 6/1994 |
| 2005/0038513 | A1 | 2/2005 | Michelson | EP | 1169971 | A2 | 1/2002 |
| 2005/0096657 | A1* | 5/2005 | Autericque et al. ............ 606/69 | EP | 1437105 | A1 | 7/2004 |
| 2006/0276792 | A1 | 12/2006 | Ensign | FR | 2727005 | A1 | 5/1996 |
| 2007/0043366 | A1 | 2/2007 | Pfefferle et al. | FR | 2827150 | A1 | 1/2003 |
| 2007/0106388 | A1 | 5/2007 | Michelson | WO | 89/09035 | A1 | 10/1989 |
| 2007/0118125 | A1* | 5/2007 | Orbay et al. .................... 606/69 | WO | 97/20526 | A1 | 6/1997 |
| 2008/0097444 | A1* | 4/2008 | Erickson et al. ................ 606/69 | WO | 99/63914 | A1 | 12/1999 |
| 2008/0243193 | A1 | 10/2008 | Ensign | WO | 00/66044 | A1 | 11/2000 |
| 2009/0234359 | A1* | 9/2009 | Onoue et al. .................... 606/71 | WO | 00/66045 | A1 | 11/2000 |
| | | | | WO | 0203885 | A2 | 1/2002 |
| | | | | WO | 03005939 | A2 | 1/2003 |
| | | | | WO | 2004086990 | A1 | 10/2004 |

FOREIGN PATENT DOCUMENTS

| | | | |
|---|---|---|---|
| CA | 2163243 | A1 | 9/1995 |
| CA | 2383634 | A1 | 8/2001 |
| DE | 1139331 | B | 11/1962 |

* cited by examiner

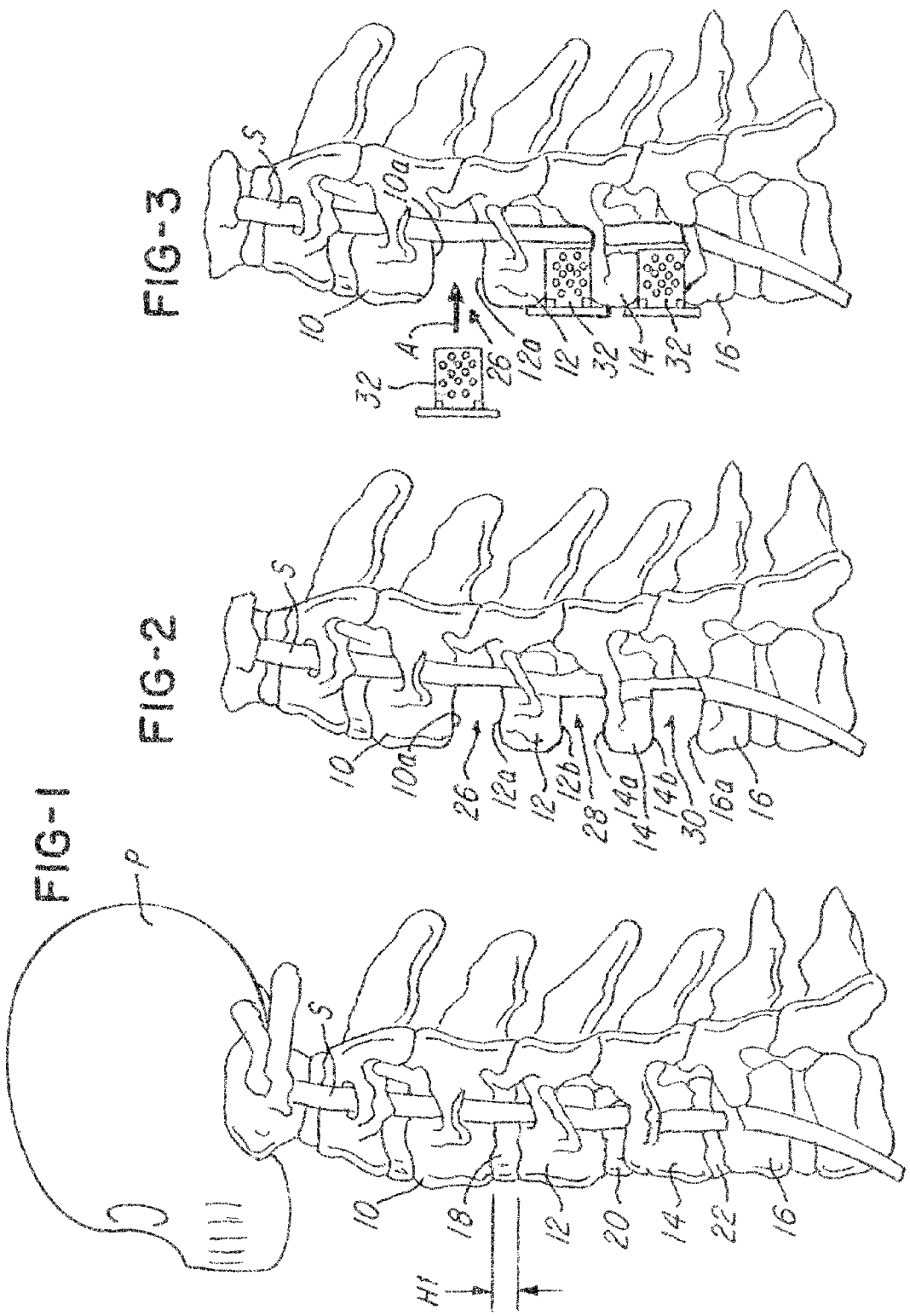

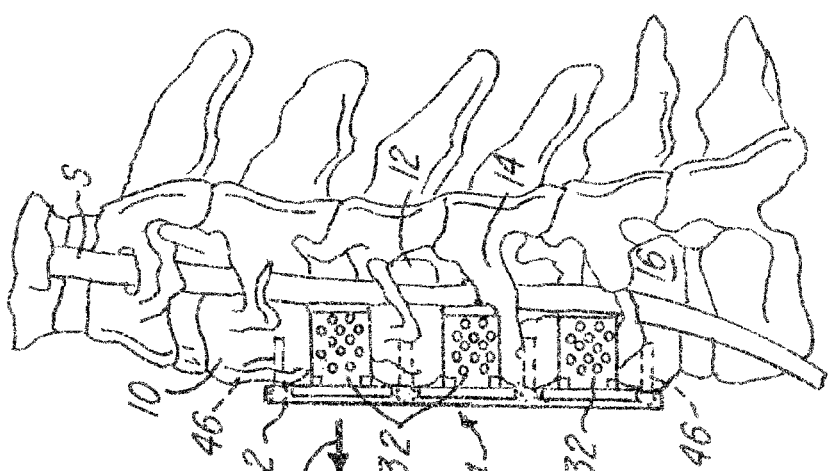
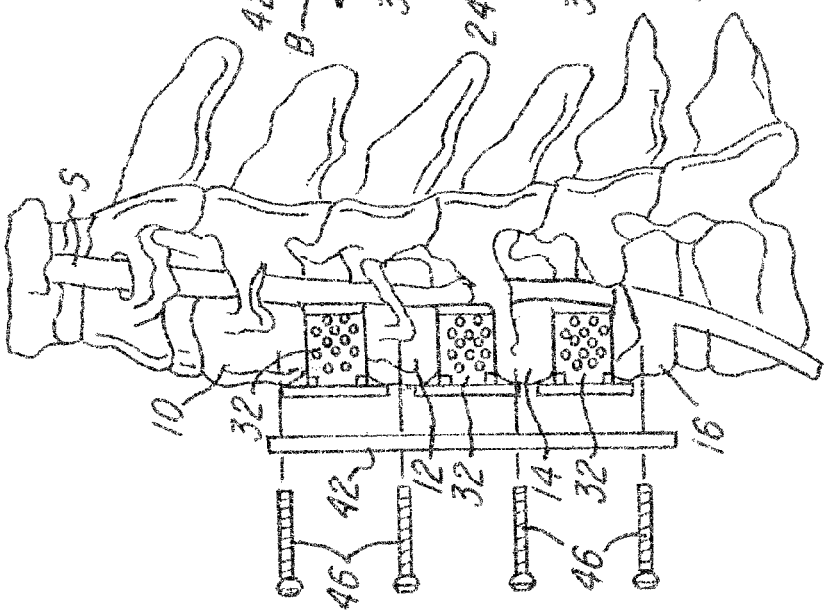
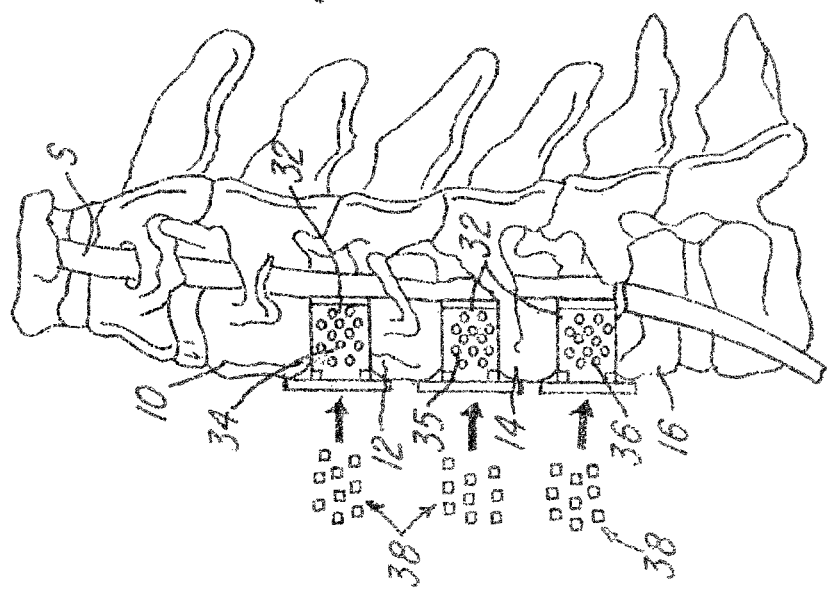

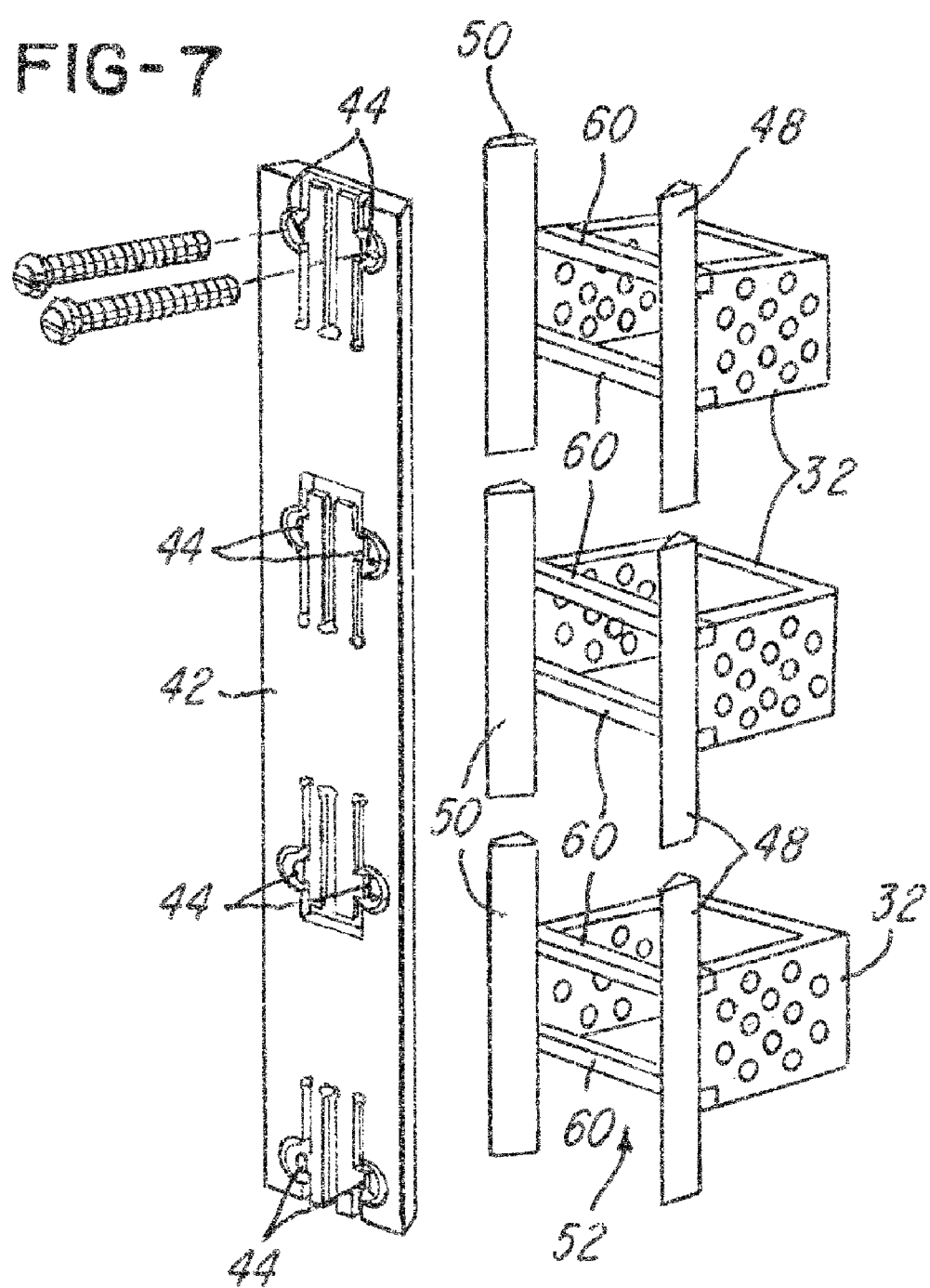

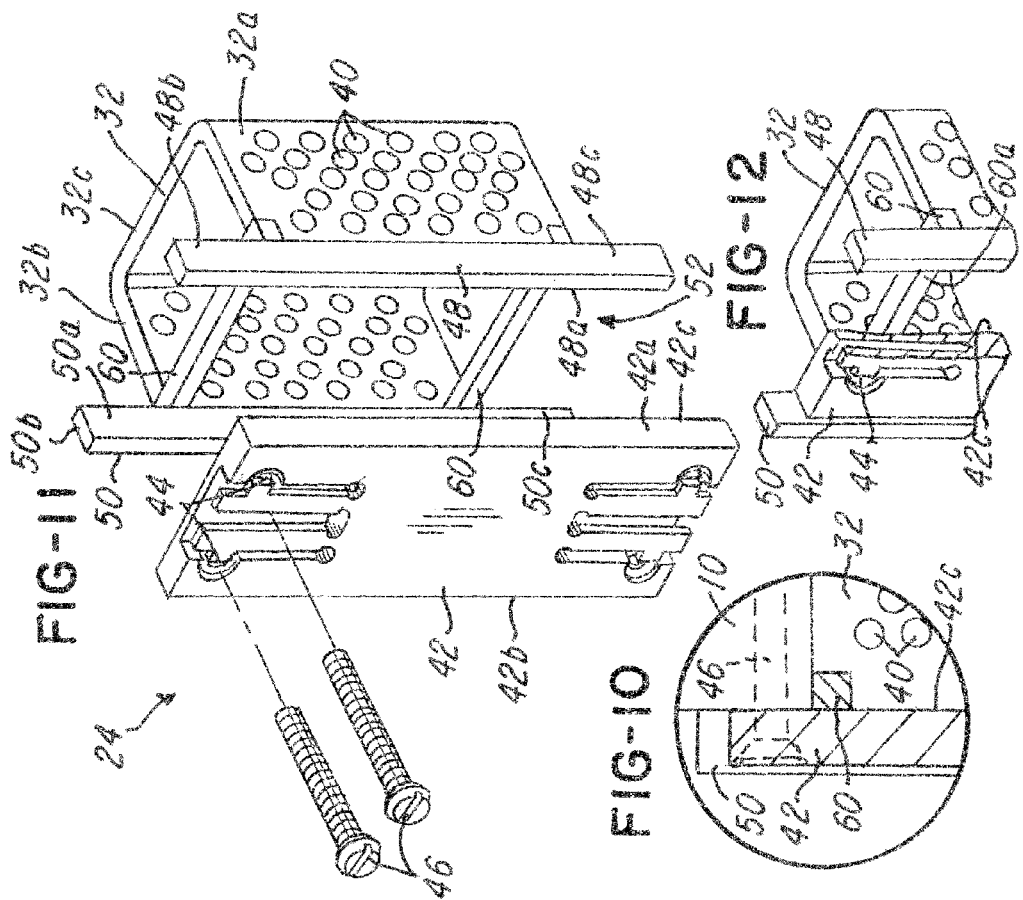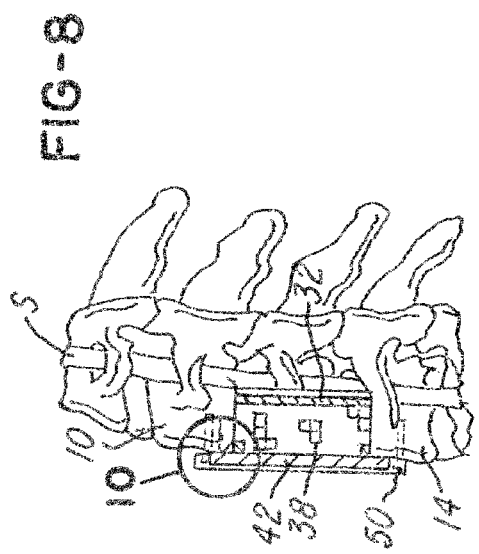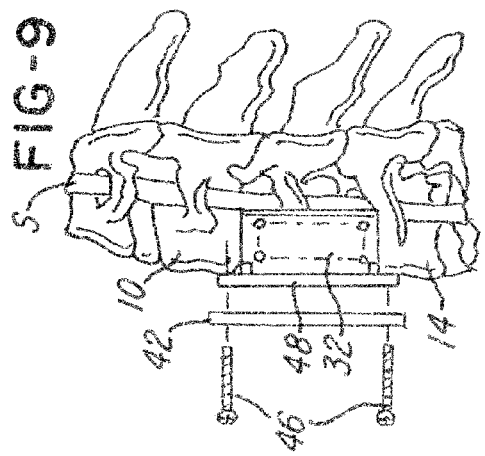

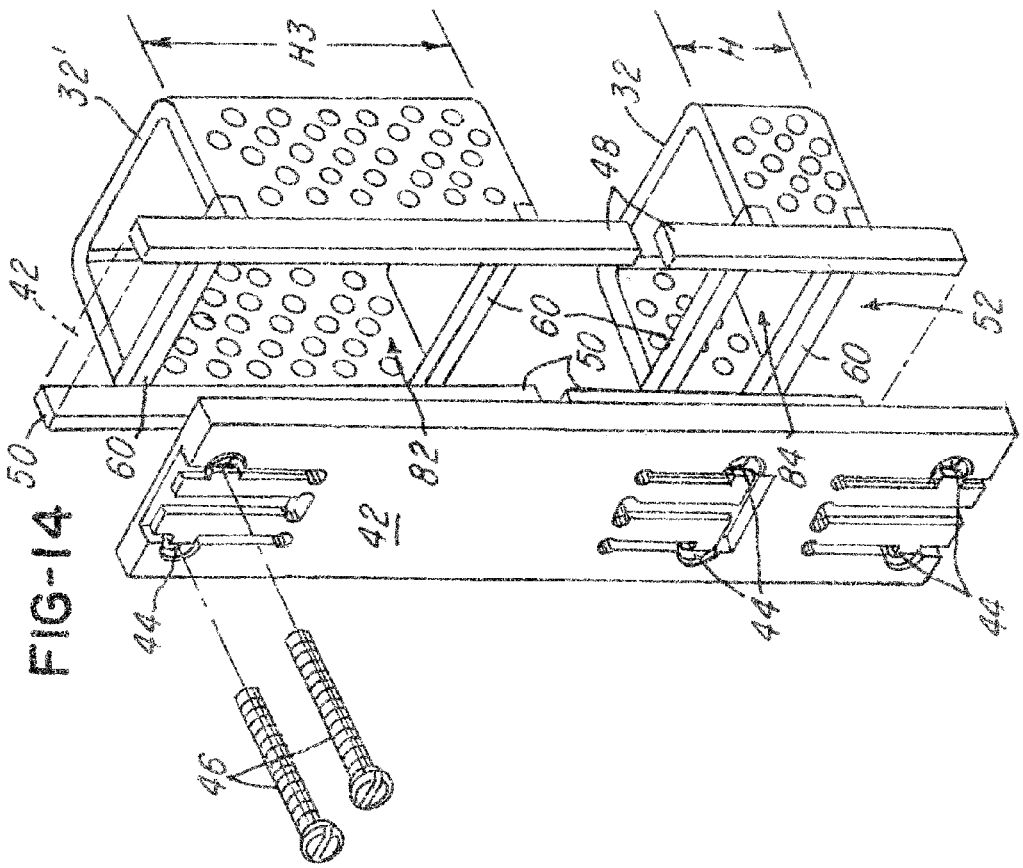
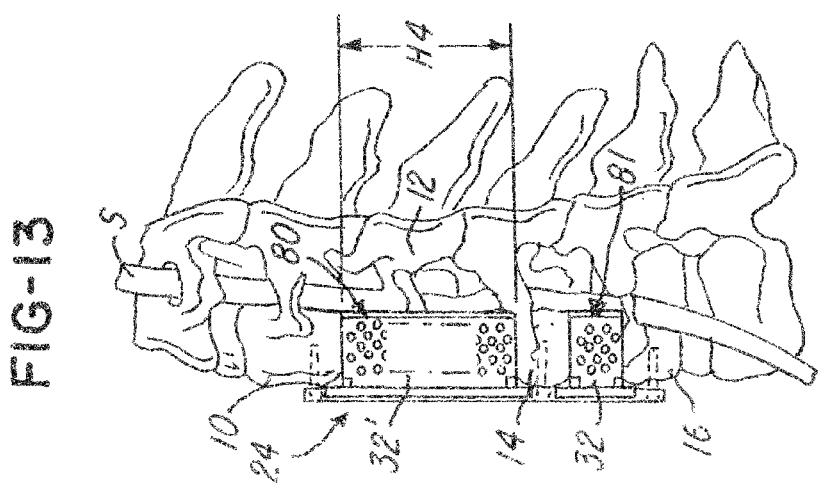

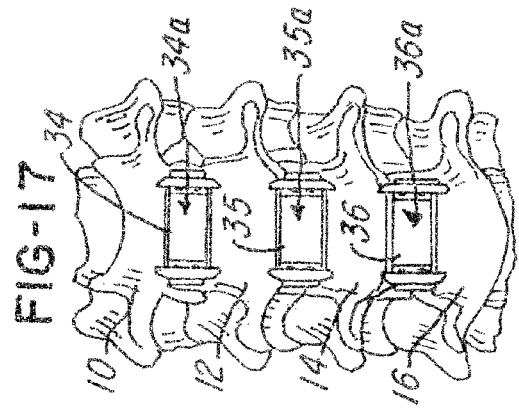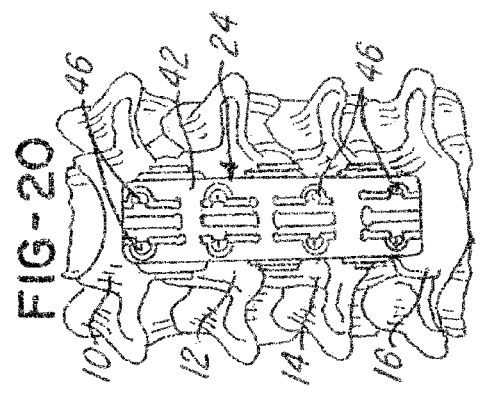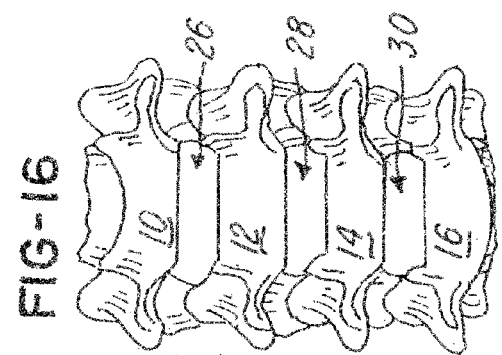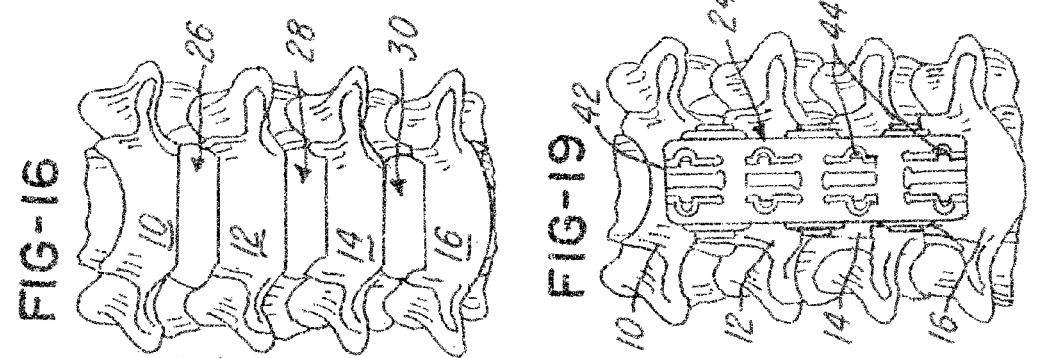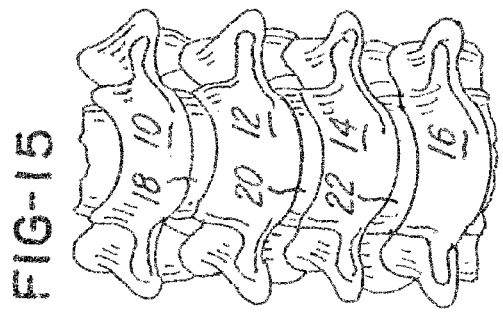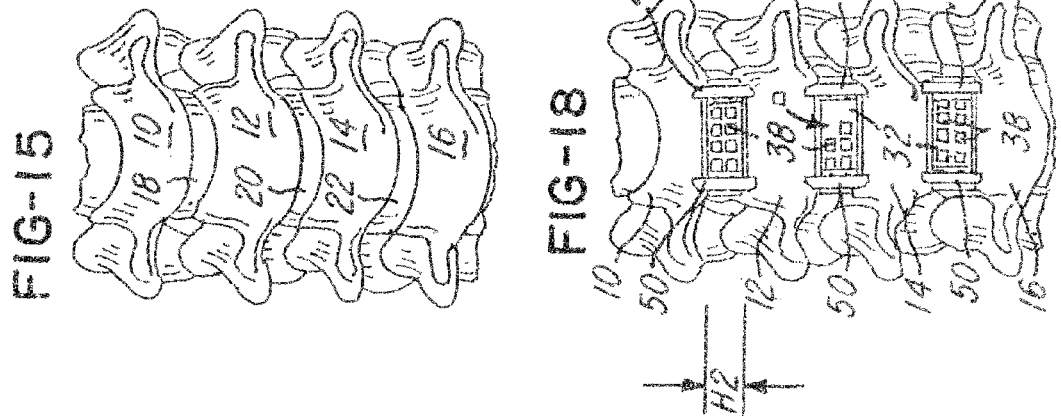

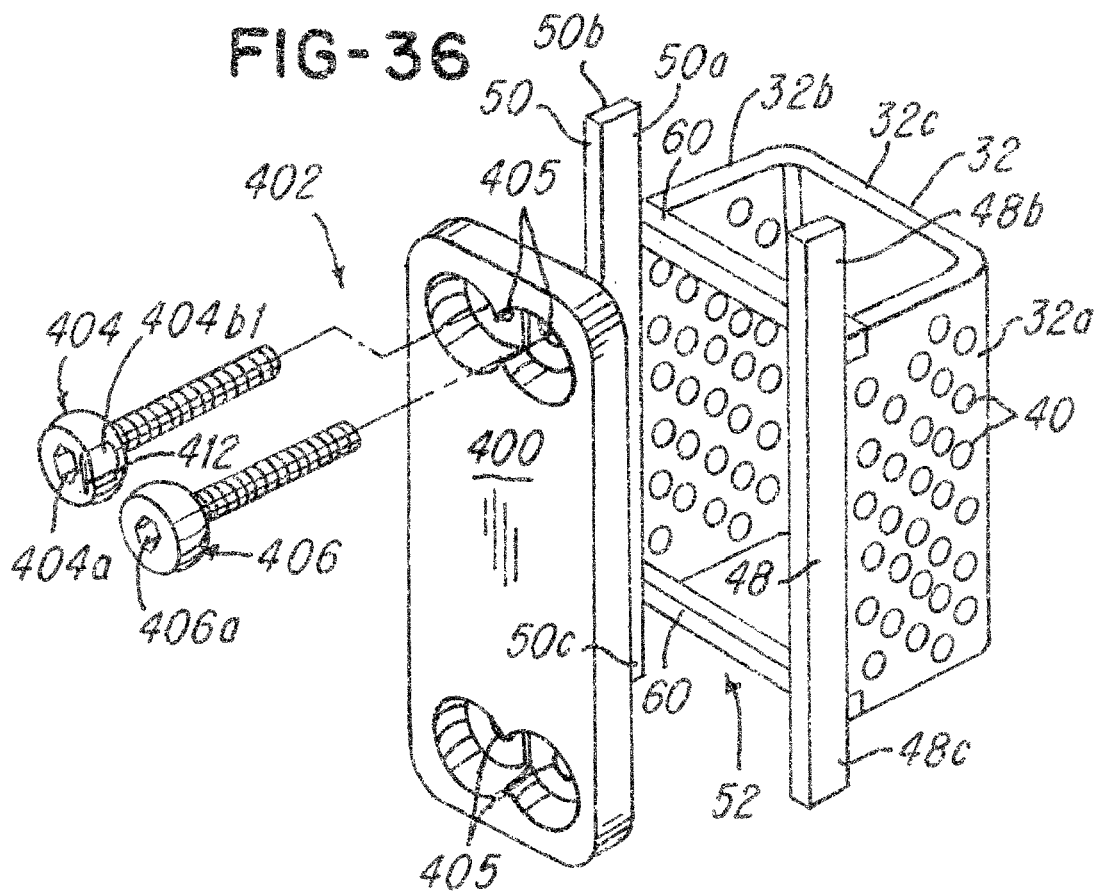
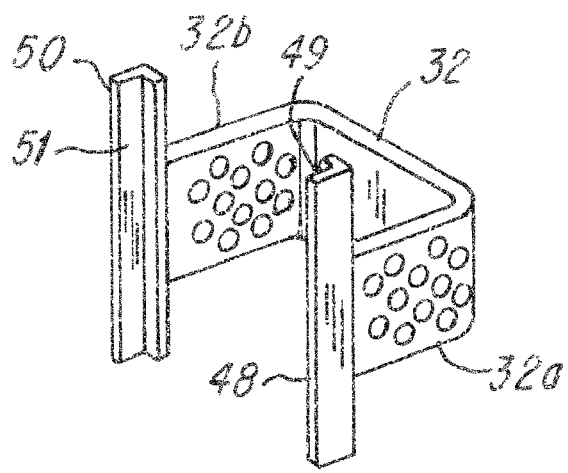

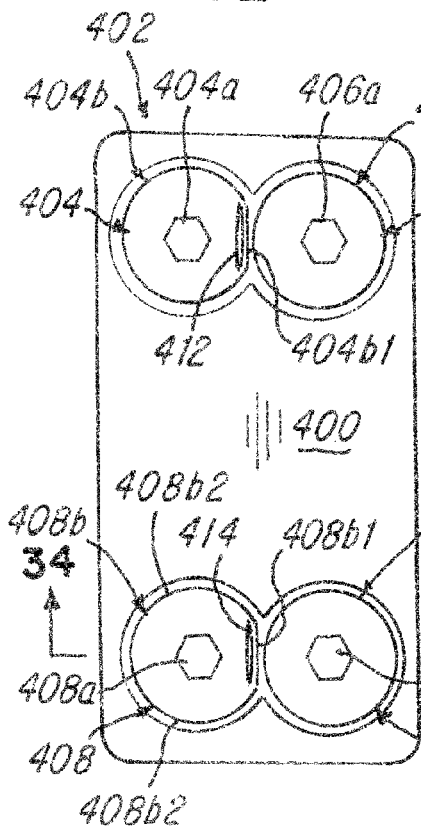
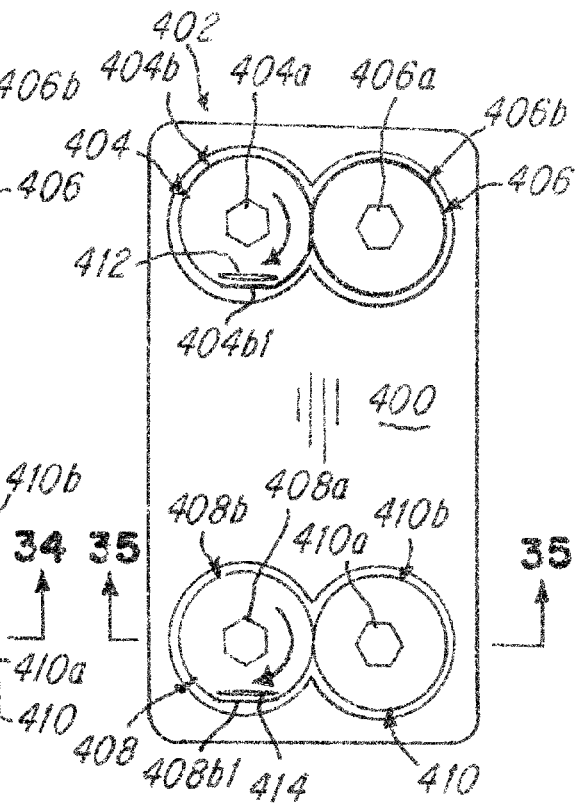
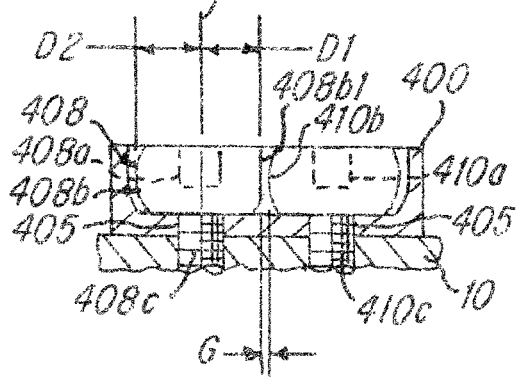
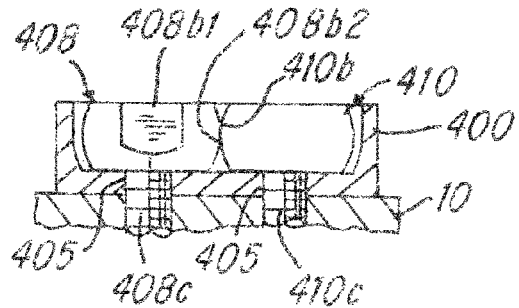

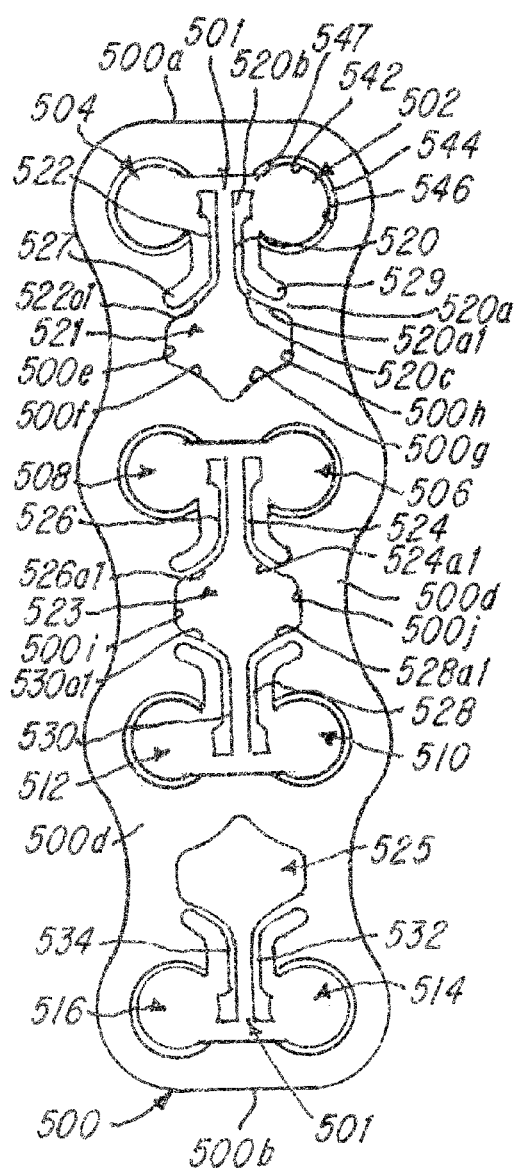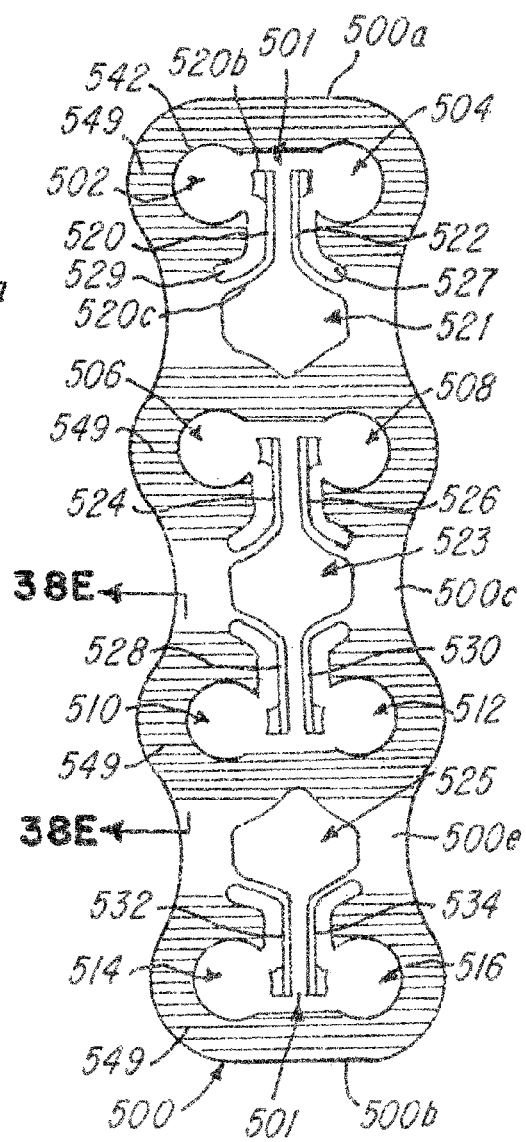

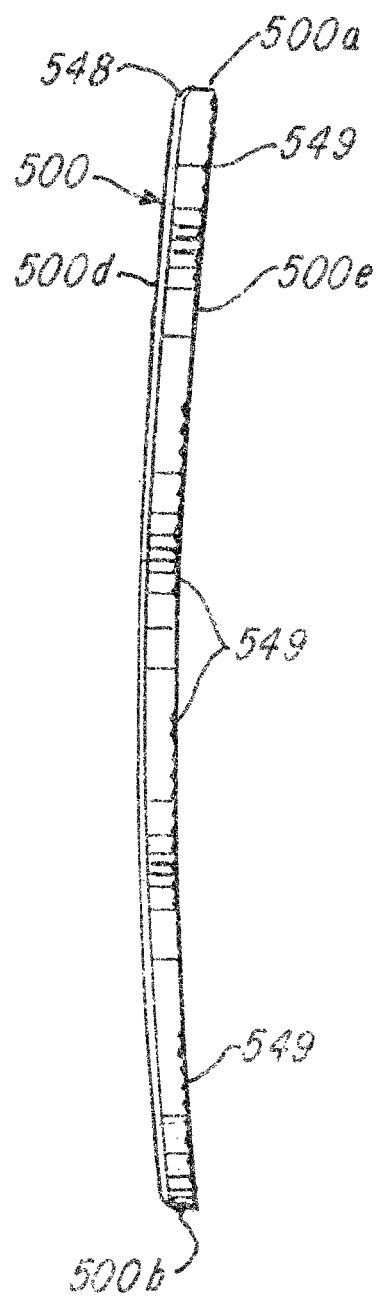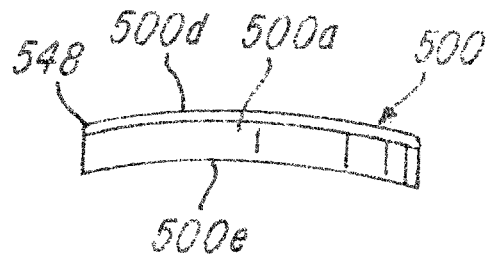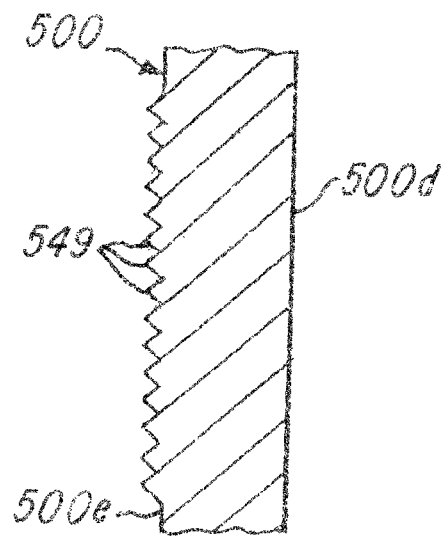

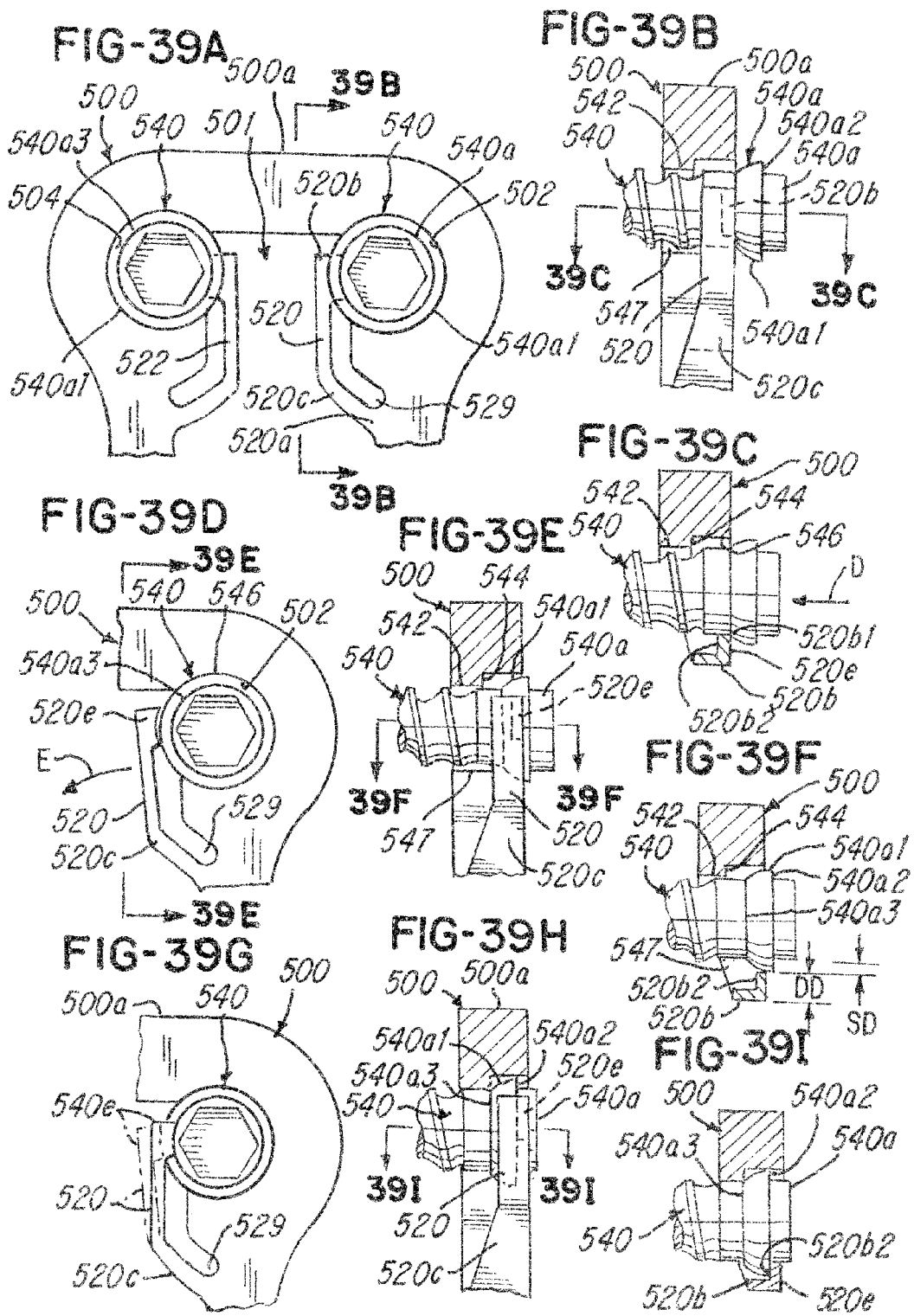

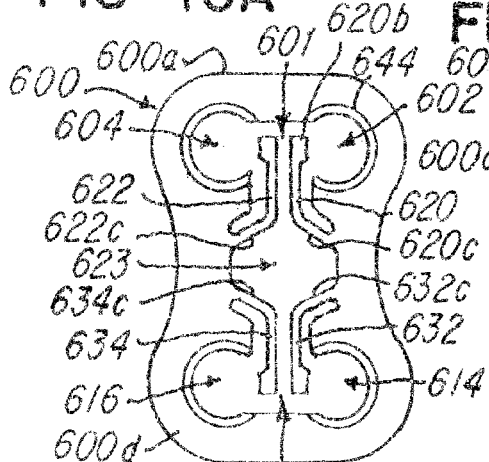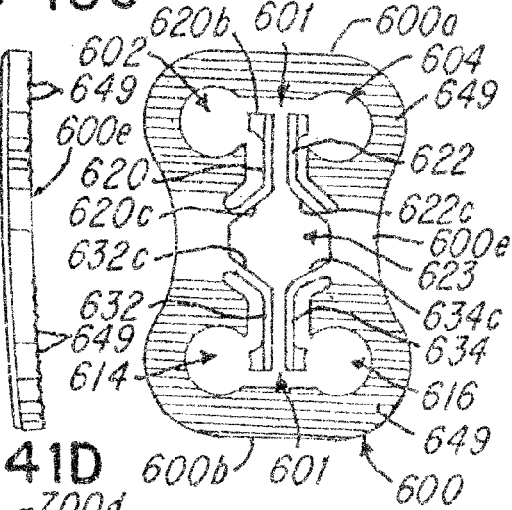
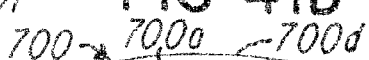
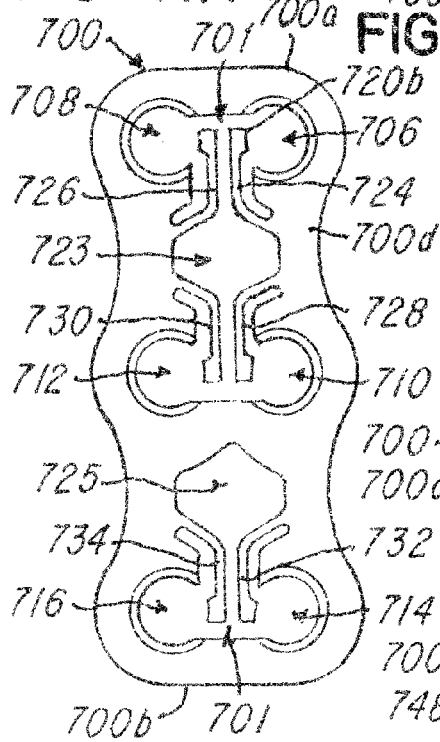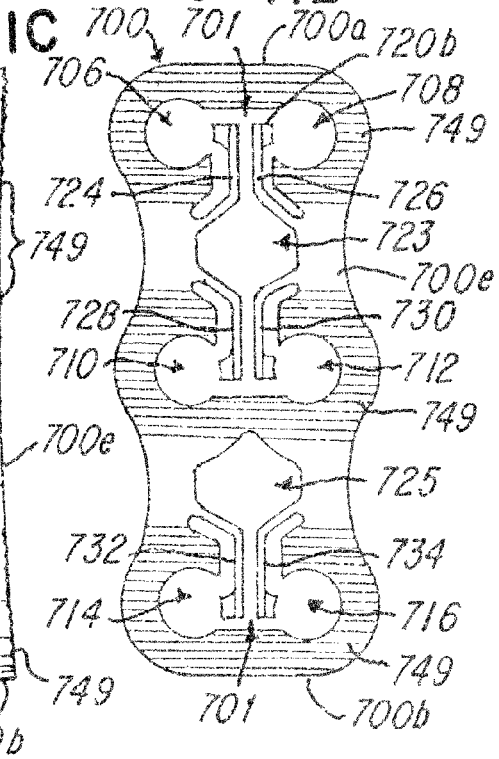

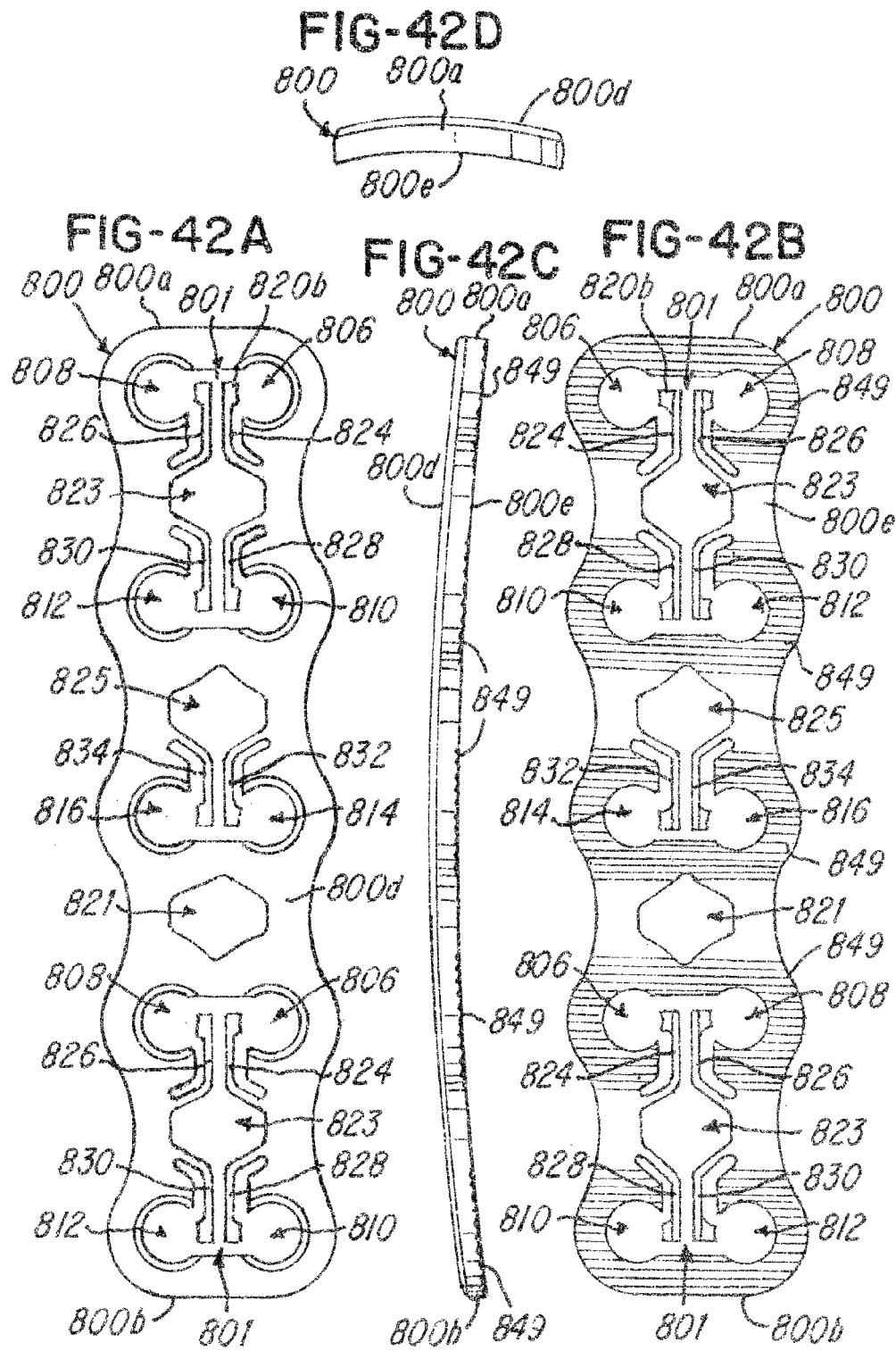

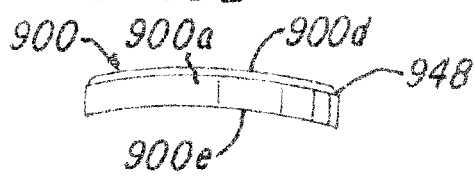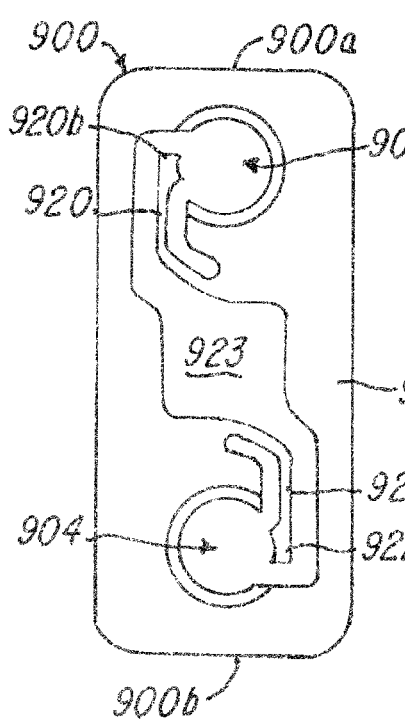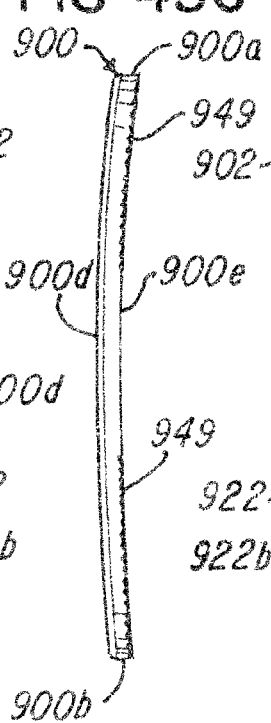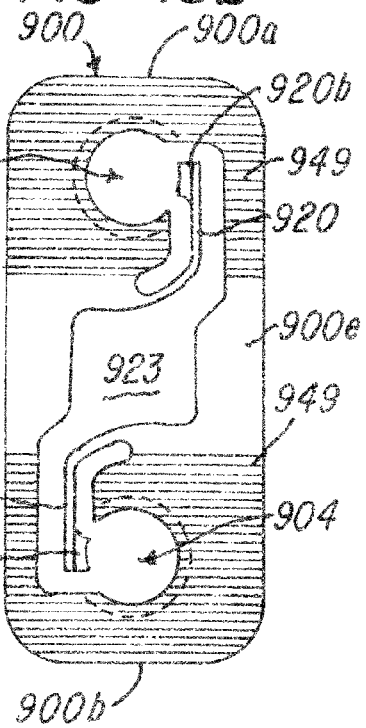

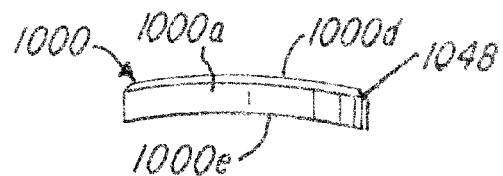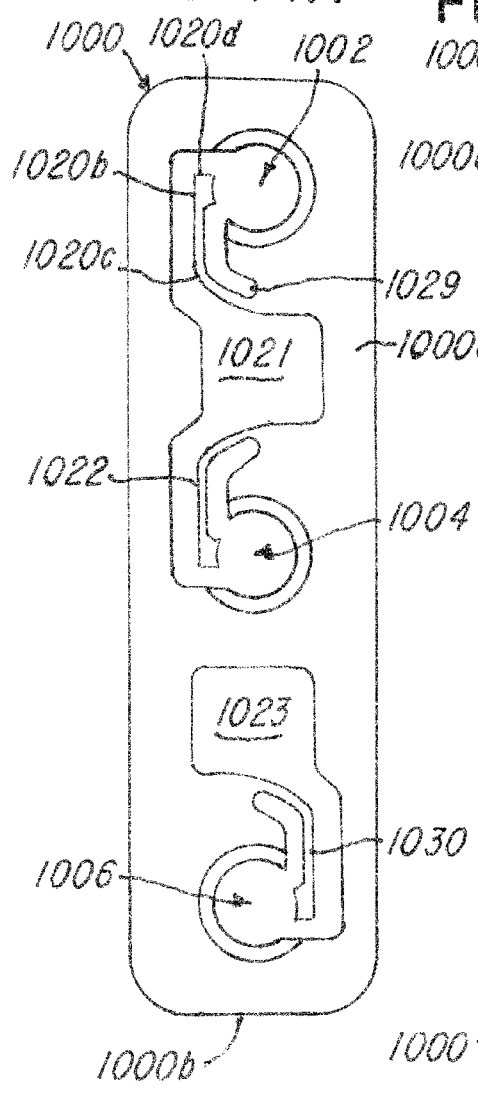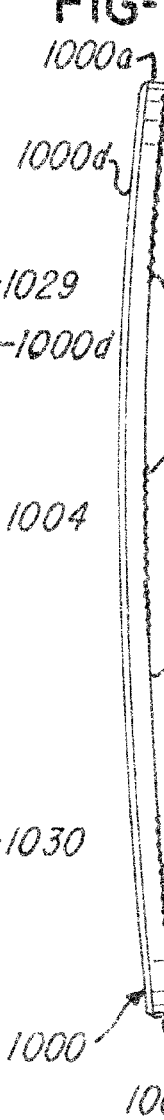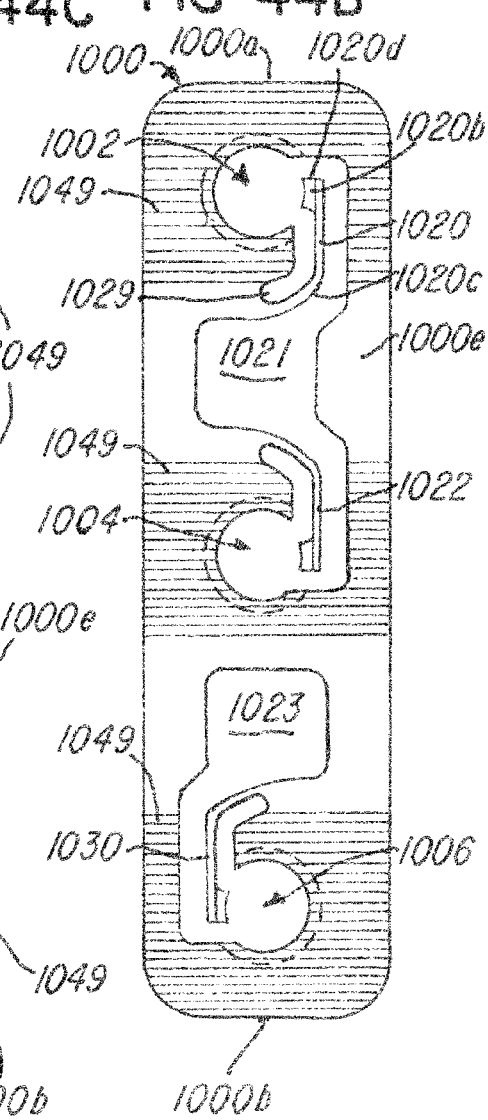

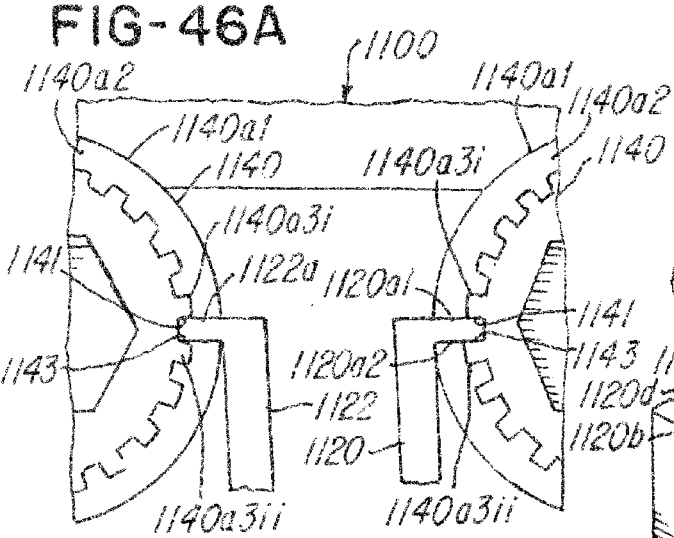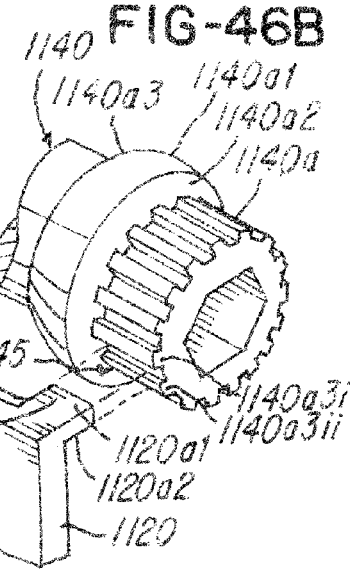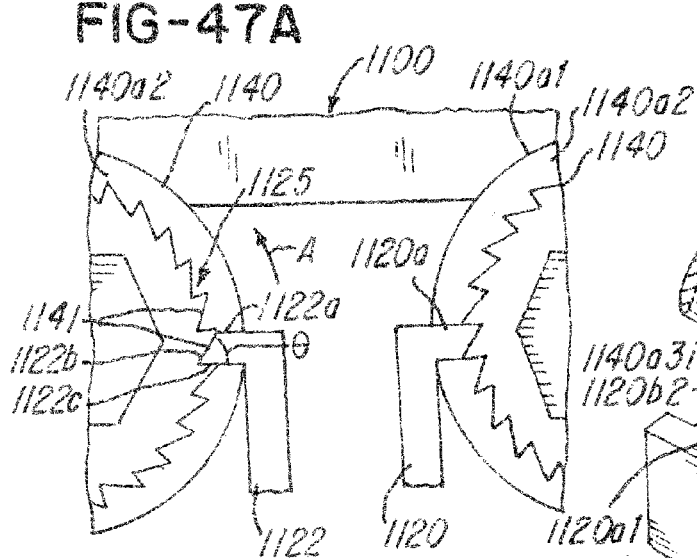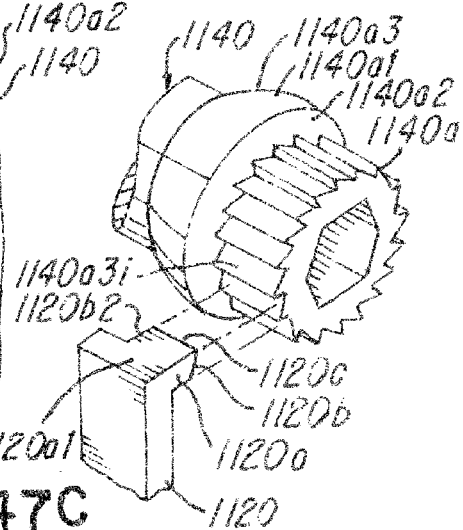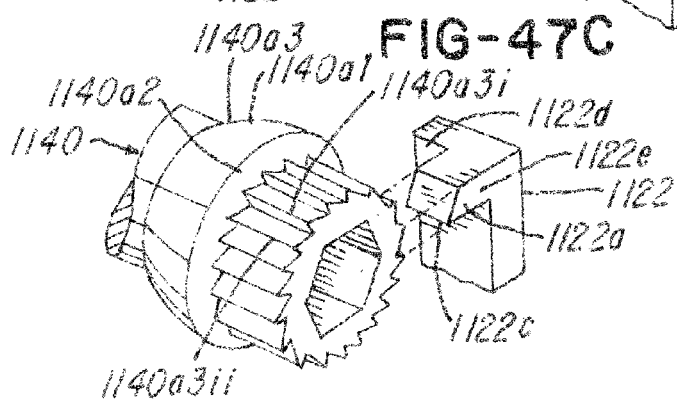

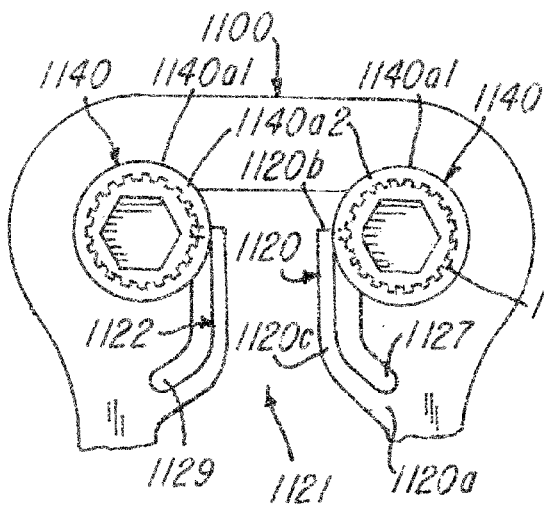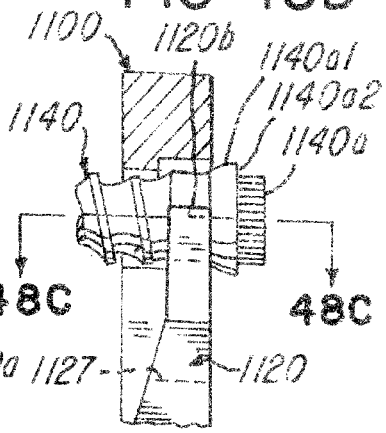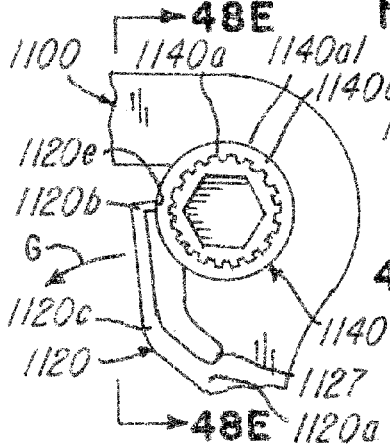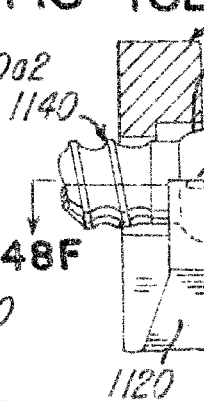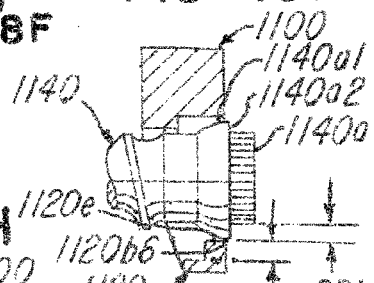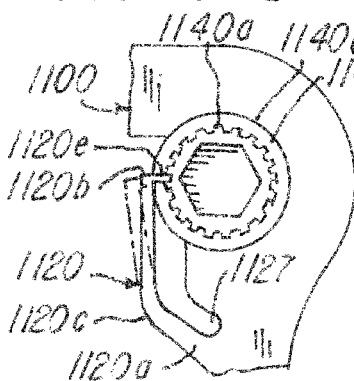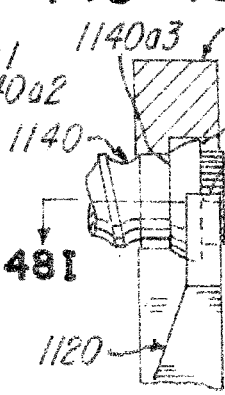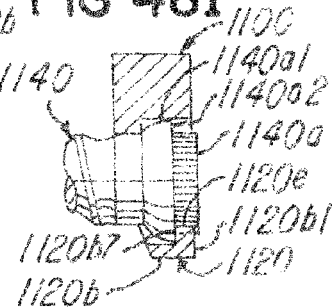

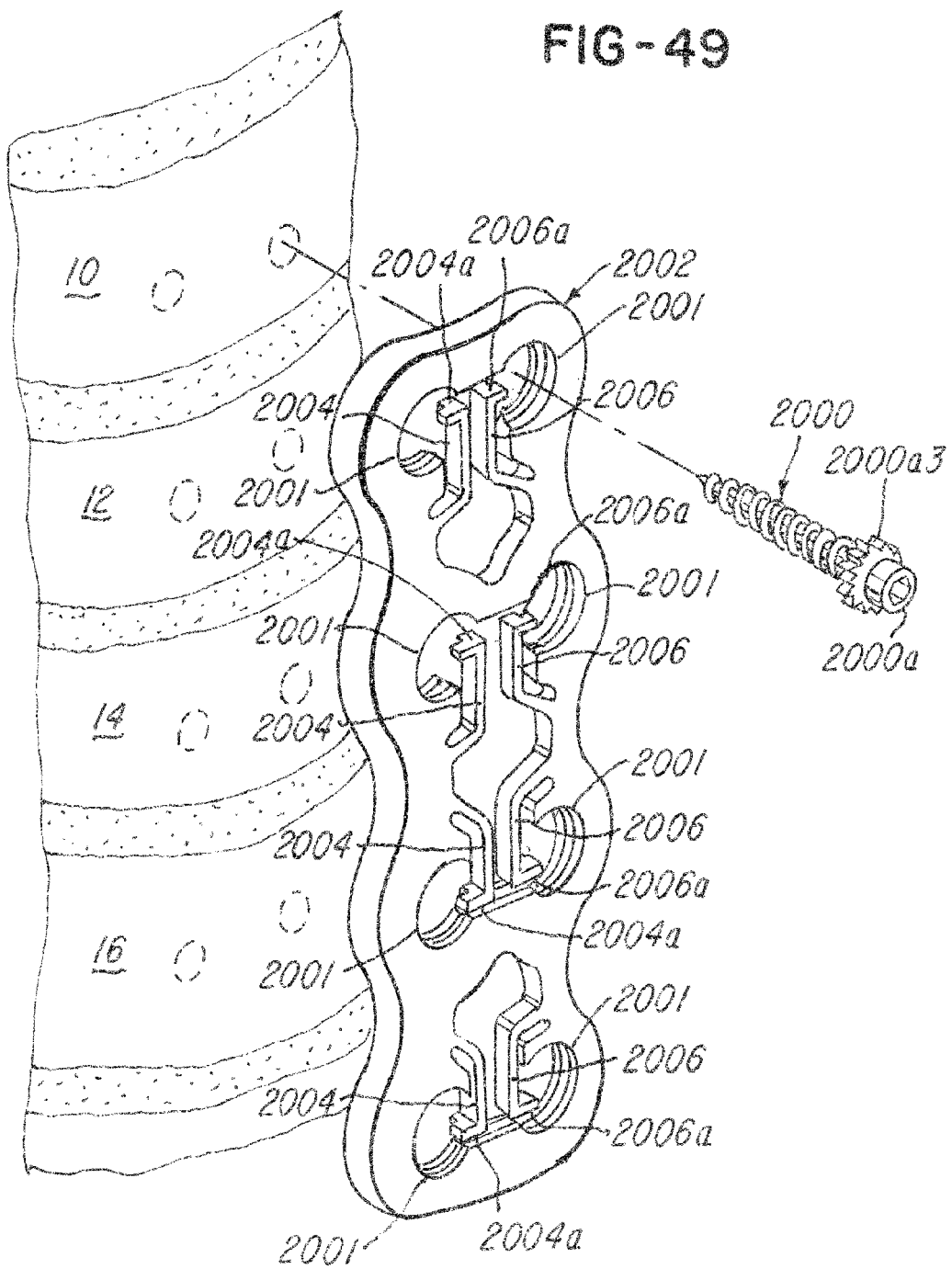

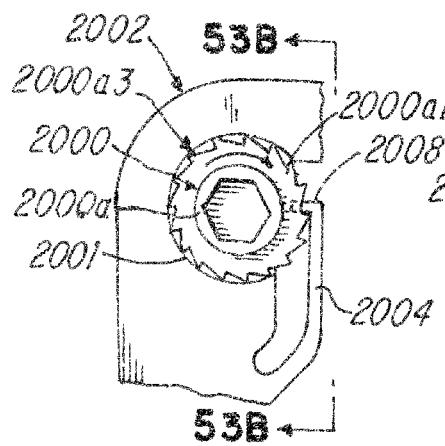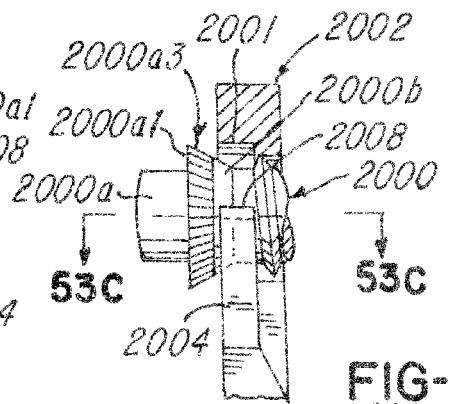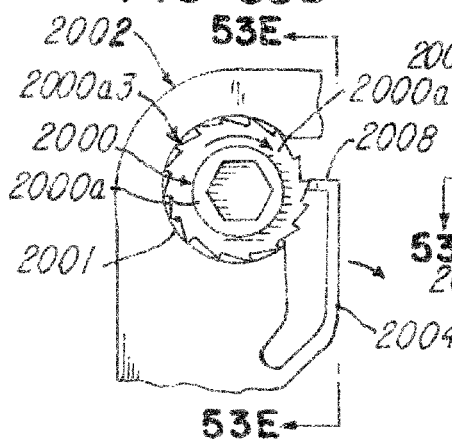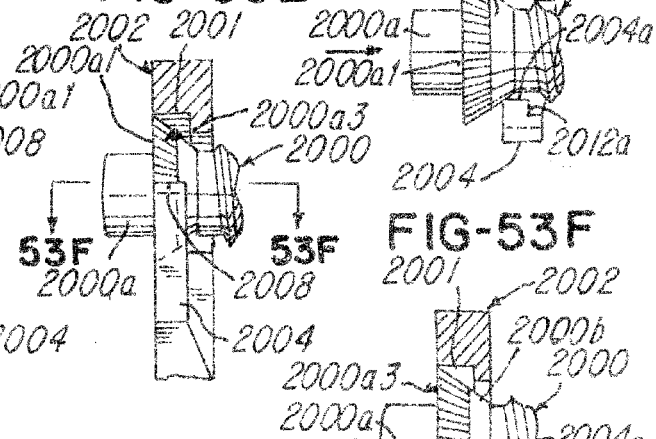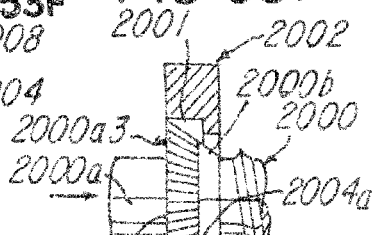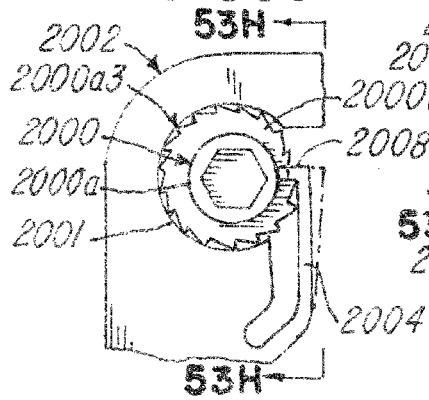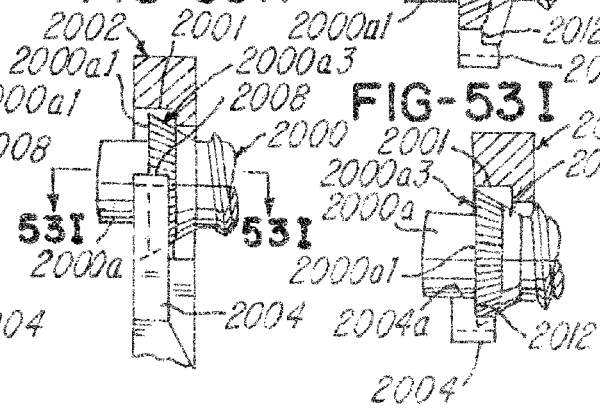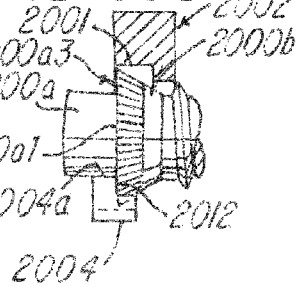

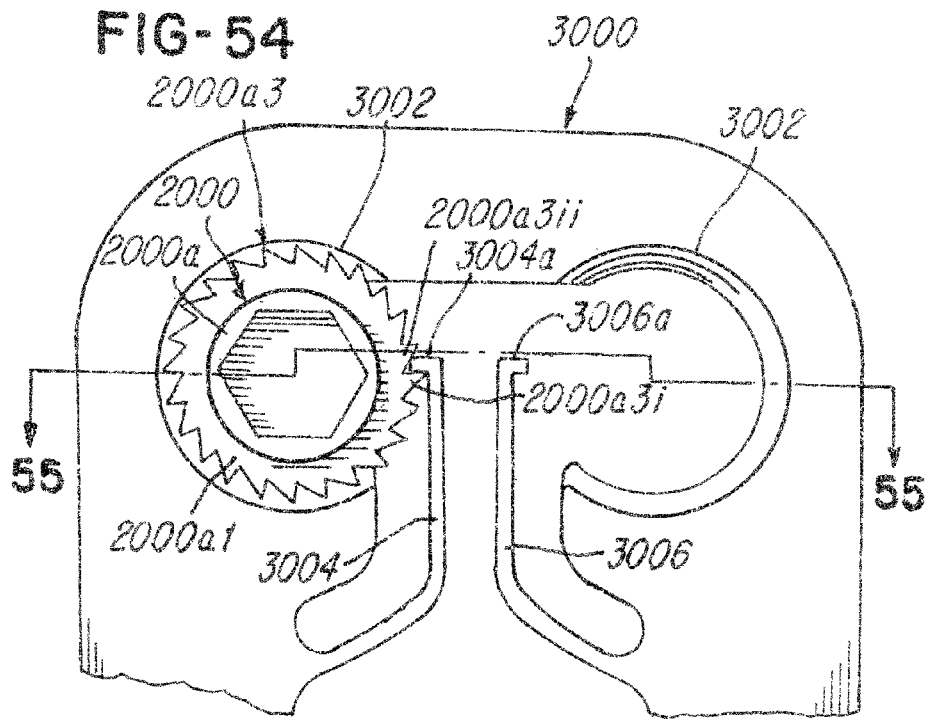
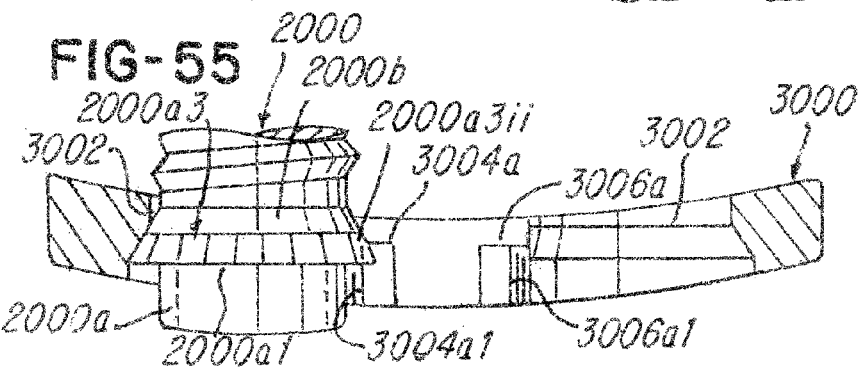
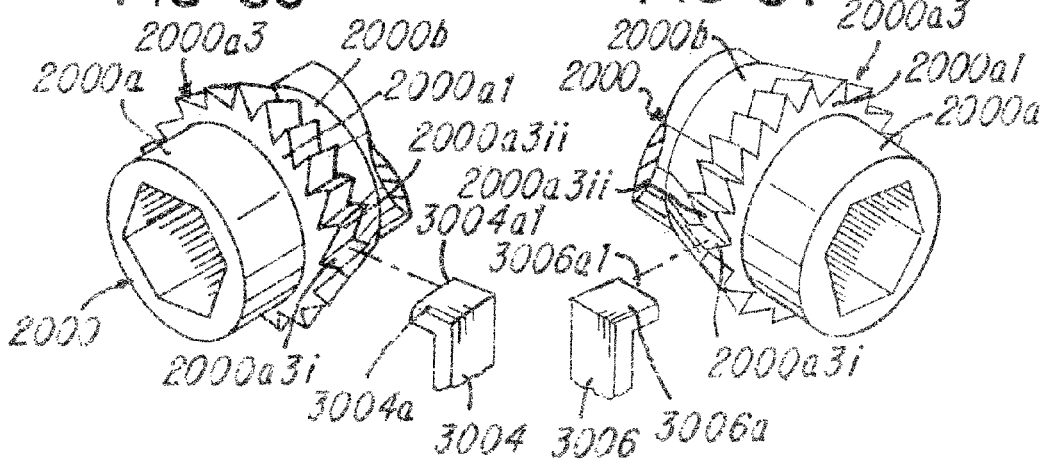

US 8,372,152 B2

SPINAL FUSION SYSTEM UTILIZING AN IMPLANT PLATE HAVING AT LEAST ONE INTEGRAL LOCK AND RATCHET LOCK

RELATED APPLICATION DATA

This application is a continuation-in-part of U.S. patent application Ser. No. 11/379,301 filed Apr. 19 2006, which is a continuation-in-part of U.S. patent application Ser. No. 10/858,629, filed Jun. 2, 2004, which is a continuation-in-part of U.S. patent application Ser. No. 10/675,361 filed Sep. 30, 2003, now issued as 7,182,782, all of which are incorporated herein by reference and made part hereof.

BACKGROUND OF THE INVENTION

1. Field of the Invention

This invention relates to a implant plate system and device and a method for implanting the device and, more particularly, to a fusion system and method for fusing bones. The preferred application for the device is in spinal surgery, however applications in other areas of orthopedic surgery are appropriate.

2. Description of the Related Art

Many types of prosthetic devices have been proposed in the past. For example, U.S. Pat. No. 5,192,327 to Brantigan concerns a surgical prosthetic modular implant used singularly or stacked together to support and fuse together adjacent vertebrae or to totally or partially replace one or more vertebrae in a vertebral column. Other surgical implant devices and methods are shown in U.S. Pat. Nos. 4,488,543; 5,192,327; 5,261,911; 5,549,612; 5,713,899; 5,776,196; 6,136,002; 6,159,245; 6,224,602; 6,258,089; 6,261,586; 6,264,655; 6,306,136; 6,328,738; 6,361,537; and 6,592,586. Some or all of these devices have improved the success rate and have simplified the surgical techniques in inter-body veritable fusion.

U.S. Pat. No. 6,258,089 B1 issued Jul. 10, 2001 to Campbell et al. for an Anterior Cervical Plate And Fixation System discloses an anterior cervical plate is disclosed, along with threaded fasteners for securing the plate to vertebrae or other osseous material. The cervical plate has several pockets or apertures, preferably at least four, to receive a corresponding number of the fasteners. The pockets have spherical surfaces, and the fasteners have heads with similarly sized spherical surfaces, which when engaged permit each of the fasteners to be oriented at a variety of projection angles with respect to the plate. In connection with each pocket, the cervical plate incorporates a fastener retaining feature. The feature can take the form of a cantilevered tab or a beam supported at its opposite ends, in each case plastically deformable between an open position for admitting the fastener and a closed position for preventing retraction.

U.S. Pat. No. 5,549,612 issued Aug. 27, 1996 to Yapp et al. for Osteosynthesis Plate System discloses an osteosynthesis plate system is particularly well adapted to securely fuse adjacent cervical vertebrae. The plates are adapted for mounting upon the anterior or posterior surfaces of the vertebrae. Plates for mounting on the anterior vertebral surfaces have a concave bone contacting surface and a bone screw locking mechanism integral with each screw hole. Moreover, the bone contacting surface of the plate has a plurality of bone penetrating protrusions to more securely affix the plate to bone. Plates for mounting on the posterior vertebral surfaces also have bone penetrating protections on their bone contacting surfaces. Such plates are formed so as to have a curved bone contacting surface that is concave in the transverse axis of the plate and convex in the longitudinal axis of the plate. The screw holes of such plates are constructed so as to guide a bone screw along a desired angle to improve the anchoring of the screws in bone.

U.S. Pat. No. 4,488,543 issued Dec. 18, 1984 to Tornier for Device For Osteosynthesis Of Fractures Of The Extremities Of The Femur discloses a device for osteosynthesis of the fractures of the extremities of the femur comprises a plate in which holes are provided for the passage of screws intended to be inserted into the bone to make the fractured bone and the plate solid. One end of the plate to be applied against one of extremities of the femur is wider than the other end and includes three holes arranged in an isosceles triangle. The median plane of the one end defines a plane which forms, with the plane of the rest of the plate, an obtuse angle of between 160° and 175°.

U.S. Pat. No. 6,361,537 B1 issued Mar. 26, 2002 to Anderson for Surgical Plate With Pawl And Process For Repair Of A Broken Bone discloses a surgical plate and process for preventing screw backout of repaired bones. At least one pawl is provided on a surgical plate adjacent to a screw hole. A screw having a ratchet wheel is inserted through the hole and screwed into the bone. The pawl engages the ratchet wheel to prevent rotational movement of the screw to prevent the screw from backing out. In a preferred embodiment, a pawl plate comprising a base portion is rigidly connected to the surgical plate and a torsion bar is pivotally connected to the base portion. The pawl is positioned at the end of the torsion bar. In the preferred embodiments, several of these special screw holes with pawls, and several screws (each with a ratchet wheel) are used in bone repair.

While the above approaches may have yielded favorable results in certain circumstances, there remains a need for reducing the need for multiple parts or tools and for providing a simpler, more reliable means and system of facilitating prevention of the screws from migrating out of the bone by axial or rotational movement after the plate is fixed thereto.

Among some of the problems associated with the prior art devices is that after the device is inserted into a patient during a surgical procedure, there was a possibility of inadequate fixation of the implant device due to false-locking of fixating screws.

Another problem with the prior art devices is that the implant device and associated bone graft could loosen after the surgical procedure due to undesired back-out of fixating screws.

Moreover, in some of the prior art devices, the fixation screws are locked to the prosthetic device in a multiple-step process, increasing the possibility for user error or false fixation.

Another problem with prior art implant plate systems is that the screws or fasteners which secured the plate had a tendency to withdraw, causing injury to local structures by the screws themselves.

What is needed, therefore, is a system and method, which facilitates overcoming one or more of the aforementioned problems as well as other problems and to provide a device that has unique features that will facilitate reducing the risk associated with neurological surgeries and advance the present state of the art.

Therefore, there is a need for a plate and fixation system in which bone screws or other fasteners are more securely retained and less likely to work loose or migrate, which reduces or eliminates the need for auxiliary components, screws, tools or additional fixtures.

SUMMARY OF THE INVENTION

It is, therefore, one object of the embodiments to provide a plate having a system that improves over devices of the past.

Another object is to provide a plate having locking members that are arcuate, resilient and that reduce or eliminate the requirement of the need for tools, separate parts or components.

In one aspect this invention comprises an implant plate comprising a plate member having a plurality of apertures, each of the plurality of apertures being capable of receiving at least one screw, a plurality of resilient stop members, each of the plurality of resilient stop members being integral with the plate and being operatively associated with at least one of the plurality of apertures, respectively; the screw comprising a head having a plurality of areas for receiving at least a portion of at least one of the plurality of resilient stop members; and each of the plurality of resilient stop members cooperating with at least one of the plurality of areas to facilitate preventing the at least one screw from moving in at least one of a rotational direction or an axial direction.

In another aspect this invention comprises an implant plate system comprising: a plate member having a plurality of screw-receiving apertures for receiving a screw; and a plurality of locks formed in or mounted on the plate member for preventing migration of a plurality of screws situated in the plurality of screw-receiving apertures, respectively, the plurality of locks being adapted to facilitate preventing axial and rotational movement of said plurality of screws, respectively.

In still another aspect this invention comprises prosthetic implant plate comprising: a plate; and a lock for preventing rotational movement and axial movement of at least one screw after the at least one screw is received in the plate and screwed into a spinal bone.

In still another aspect this invention comprises implant plate comprising: at least one aperture; and at least one integral lock integral with the plate and having an end associated with the at least one aperture for facilitating preventing a screw received in the at least one aperture from rotating in at least one of a clockwise or counterclockwise direction; the at least one integral lock being resilient and normally biased into the at least one aperture.

In still another aspect this invention comprises implant plate system comprising: a plate member having a plurality of screw-receiving areas, each of the plurality of screw-receiving areas being capable of receiving a screw; and a plurality of locking fingers associated with the plurality of screw-receiving areas, respectively, each of the plurality of locking fingers being resilient adapted to prevent axial movement of the screw and having an end that is normally biased into at least one of the plurality of screw-receiving areas and urges itself against the screw after the screw is received in one of the plurality of screw-receiving areas.

In still another aspect this invention comprises implant system comprising: a plate member having a plurality of screw-receiving openings; a plurality of detents integral with the plate member and having a detent portion in communication with the plurality of screw-receiving openings, respectively; and a plurality of screws for situating into the plurality of screw-receiving openings, respectively, each of the plurality of screws being adapted to cooperate with at least one of the plurality of detents, respectively, and be retained by the plate member by the plurality of detents such that each of the plurality of screws are restricted from moving in both an axial direction or a rotational direction.

In still another aspect of this invention comprises plate system comprising: a screw having a screw head; a plate having an aperture for receiving the screw head and a window area; and at least one pawl for restricting or preventing the screw from moving in at least one of an axial direction or a rotational direction and the at least one pawl being urged into the window area in response to a screw being received in the aperture.

These and other objects and advantages of the invention will be apparent from the following description, the accompanying drawings and the appended claims.

BRIEF DESCRIPTION OF THE DRAWINGS

FIG. 1 is a partial side view a human spine illustrating anteriorly discs between various spinal bones;

FIG. 2 is a partial side view of the spinal column shown in FIG. 1 illustrating several of the discs removed, for example, after surgical procedure;

FIG. 3 is a partial side view of the human spine with the housings according to one embodiment of the invention situated therein;

FIG. 4 is a partial side view of the human spinal column illustrating graft material being inserted anteriorly into the housing;

FIG. 5 is a partial exploded side view of the embodiment shown in FIG. 1-4 illustrating a cover and a plurality of screws which will secure the cover to the spinal column;

FIG. 6 is a side view similar to FIG. 5 illustrating after the cover has been mounted to the spinal column;

FIG. 7 is a exploded view of the device shown in FIG. 6, illustrating a plurality of housings and a single cover for use with covering the plurality of housings;

FIG. 8 is partial side view illustrating an elongated housing and cover used during a vertebrectomy procedure;

FIG. 9 is a partial side view of the spinal column illustrated in FIG. 8 showing the elongated housing situated between adjacent spinal bones in a single cover to be affixed to those spinal bones;

FIG. 10 is an exploded view of the circle area shown in FIG. 8;

FIG. 11 is a exploded view of the elongated housing illustrated in FIGS. 8 and 9 and the cover and screws associated therewith;

FIG. 12 is a partial fragmentary view of the cover and housing after the cover has been situated between a pair of rails associated with the housing;

FIG. 13 illustrates a partial side view of an embodiment showing a plurality of housings of different sizes used with a single cover;

FIG. 14 is a exploded view of the housings and cover illustrated in FIG. 13;

FIG. 15 is a partial anterior side view a human spine illustrating the discs between various spinal bones;

FIG. 16 is a partial anterior view of the spinal column shown in FIG. 1 illustrating several of the discs removed, such as by surgical procedure;

FIG. 17 is a partial anterior view of the human spine with the housings according to one embodiment of the invention situated therein;

FIG. 18 is a partial anterior view of the human spinal column illustrating graft material being inserted anteriorly into the housing;

FIG. 19 is a partial exploded anterior view of the embodiment shown in FIG. 1-4 illustrating a cover and a plurality of screws for securing the cover to the spinal column;

FIG. 20 is a anterior view similar to FIG. 5 illustrating the cover mounted to the spinal column;

FIG. 31 is a view of a housing having walls having recessed areas for receiving the cover;

FIG. 32 is a view of another embodiment of the invention showing the plurality of fasteners or screws in an unlocked position;

FIG. 33 is a view of the fasteners or screws shown in FIG. 32 in a locked position;

FIG. 34 is a view taken along the line 34-34 in FIG. 32;

FIG. 35 is a view taken along the line 35-35 in FIG. 33;

FIG. 36 is an exploded view of the other embodiment of the invention with the locking screws illustrated in FIGS. 32-35;

FIGS. 38A-38E are various views of the embodiment shown in FIG. 37, illustrating various details of the embodiment shown in FIG. 37;

FIGS. 39A-39I are various fragmentary and sectional views illustrating the integral lock, detent or resilient finger for retaining or maintaining a screw in a lock position in the spinal bone;

FIGS. 40A-40D illustrate another embodiment of the invention showing two pairs of apertures and associated resilient fingers, detents or integral locks;

FIGS. 41A-41D is still another embodiment in the invention showing three pairs of apertures and resilient fingers, detents or integral locks;

FIGS. 42A-42D illustrate another embodiment of the invention showing five pairs of apertures and associated resilient fingers, detents or integral locks;

FIGS. 43A-43D illustrate another embodiment of the invention for the plate having a single screw per spinal bone application; and FIGS. 44A-44D illustrate yet another embodiment illustrating a single aperture or a single screw per spinal bone for an application that contemplates the use of a single screw in each of three spinal bones.

FIGS. 46A-46B are fragmentary views illustrating a two-way ratchet and pawl detent and lock;

FIGS. 47A-47C are fragmentary views illustrating a one-way ratchet and pawl detent and lock;

FIGS. 48A-48I are various fragmentary and sectional views illustrating the ratchet and pawl lock, detent for retaining or maintaining a screw in a locked position so that is restricted from axial movement and rotational movement;

FIG. 49 is a perspective view of another embodiment of the invention;

FIGS. 53A-53I are various fragmentary and sectional views showing various details of the embodiment shown in FIG. 49;

FIG. 54 is a view illustrating another embodiment of the invention; and

FIGS. 55-57 are various views of the embodiment showing various details of the embodiment shown in FIG. 54.

DETAILED DESCRIPTION OF ACCOMPANYING DRAWINGS

Figure 22:
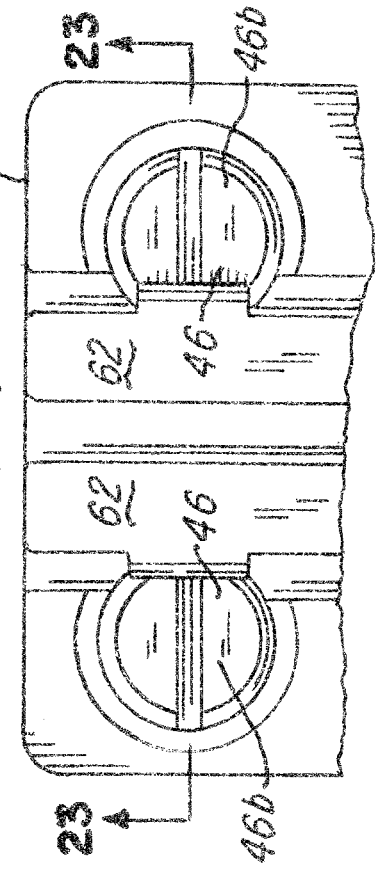
FIG. 22 is another fragmentary view of the cover after the screws are mounted and the locking mechanism retains the screws therein.

Referring now to FIG. 1, a partial side view of a patient or person P is shown having a spinal column S and a plurality of spinal bones, such as vertebrae, 10, 12, 14 and 16. Note that a disc, such as discs 18, 20 and 22 in FIG. 1, is located between adjacent pairs of spinal bones (e.g., between spinal bones 10 and 12, 12 and 14, and 14 and 16). During a spinal fusion procedure, such as a discectomy, the discs 18, 20 and 22 may be removed so that adjacent vertebrae may be fused together FIG. 2 illustrates a fragmentary view of the spinal column S shown in FIG. 1, with the discs 18, 20 and 22 removed. It should also be understood that during another surgical procedure, such as a vertebrectomy, it may be desired to remove part of all of one of the spinal bones 10-16, as illustrated in FIG. 13. In this type of neurological procedure, it may also be desired to fuse adjacent spinal bones together for reasons that are conventionally known. This invention provides means for facilitating and performing such procedures. For ease of illustration, FIGS. 15-20 provide corresponding anterior views to the side views shown in FIGS. 1-6, respectively.

In the embodiment being described, a spinal fusion system 24 is provided for use as a prosthetic implant during a neurological procedure such as the aforementioned vertebrectomy or discectomy. In general, after the discs 18, 20 and 22 (FIG. 1) are removed, as illustrated in FIG. 2, a plurality of receiving areas 26, 28 and 30 (FIGS. 2 and 17) are defined by the areas between the surfaces of adjacent spinal bones 10, 12, 14 and 16. As illustrated in FIG. 2, the receiving area 26 is bounded in part by the surface 10*a* of spinal bone 10 and surface 12*a* of spinal bone 12. Likewise, area 28 is partially bounded by surface 12*b* of spinal bone 12 and surface 14*a* of spinal bone 14, and area 30 is bounded by surface 14*b* of spinal bone 14 and surface 16*a* of spinal bone 16.

As illustrated in FIGS. 3-7 and 11 and as will be described in more detail later herein, the spinal fusion system 24 comprises a housing 32 dimensioned to be situated or received between adjacent spinal bones, such as spinal bones 10 and 12. A housing 32 is situated in each of the plurality of receiving areas 26, 28 and 30, as illustrated in FIGS. 3-4. Each housing 32 cooperates with adjacent spinal bones to define a graft area, such as areas 34, 35 and 36 in the view illustrated in FIG. 17, for receiving graft material 38 (FIGS. 4 and 18). As illustrated in FIGS. 4 and 18, the graft material 38 is situated in the areas 34, 35 and 36 after placement of the housing 32.

As illustrated in FIG. 11, the housing 32 is generally U-shaped as shown. In the embodiment being described, the housing 32 comprises a well 33 defining multiple sides and comprises a predetermined shape selected to cause the graft material to be formed into a multi-sided fused coupling between adjacent spinal bones, such as spinal bones 10 and 12 in FIG. 3. Although not shown, the housing 32 could define a shape other than rectangular, such as semi-circular, oval or other suitable shape as may be desired. Note that the housing 32 comprises a first wall 32a, a second wall 32b and a third wall 32c joining the first wall 32a and the second wall 32b. One or more of the walls 32a-32c may comprise a plurality of holes or apertures 40 which facilitate the fusing process. The apertures 40 also permit visualization of graft material 38 on x-rays.

As mentioned later herein, the predetermined shape defined by the spinal fusion system 24 may provide a fused multi-sided plug of fusion material 32 having a height H (FIGS. 14 and 16) of at least two millimeters, but typically less than approximately 180 millimeters. This height H may vary depending on the vertical size or height H (as viewed in FIG. 16) of the receiving areas 26-30 to be filled. For example, in the receiving area 26 illustrated in FIGS. 2, 14 and 16, the height H of the receiving area 26 generally corresponds to a height H1 (FIG. 1) of a disc, such as disc 18. Thus, the graft material 38 (FIG. 18) would resultantly have a fused height H2 (FIG. 18) that generally corresponds to the height H (FIG. 16) and height H1 (FIG. 1). If, for example, a housing 32 having a longer height is required, such as height H3 in FIG. 14 and height H4 in FIG. 13, such as in the event of a vertebrectomy, then the spinal fusion system 24 and housing 32 will define a height that generally corresponds to the dimension or height H (FIG. 9) to be traversed. Thus, it should be understood that the dimensions of the generally U-shaped housing 32 of the spinal fusion system 24 is selected depending on the size of the receiving areas 26-30 to be filled and the environment or application in which the spinal fusion system 24 is used. In general, the width and depth of the housing 32 will be approximately 9-20 millimeters and 7-20 millimeters, respectively.

As illustrated in FIGS. 5-7, 11,14 and 21-22, the spinal fusion system 24 further comprises a cover 42 comprising a plurality of apertures 44 that receive a plurality of screws 46, respectively, which are screwed directly into the spinal bones 10 and 16, as illustrated, for example, in FIGS. 5-6.

Figure 23:
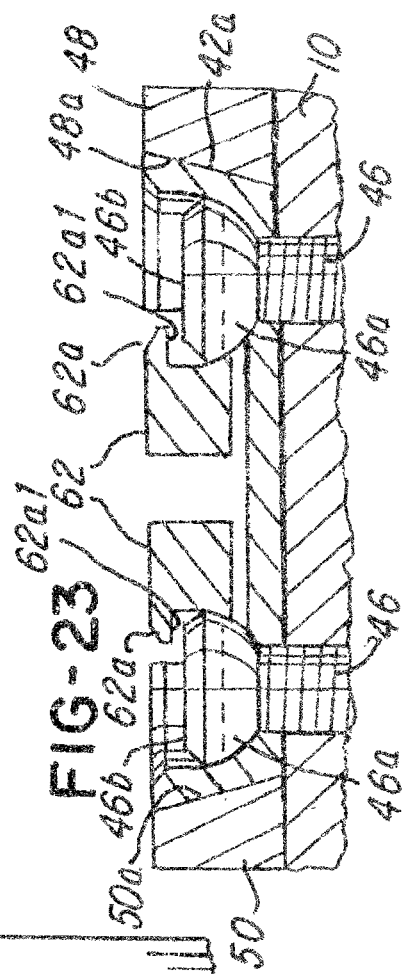
FIG. 23 is a fragmentary sectional view of the embodiment shown in FIG. 22 illustrating various features of the locking mechanism.

As illustrated in FIG. 11, the housing 32 comprises a first rail, channel wall or wall portion 48 and a second rail, channel wall or wall portion 50 which cooperate to define a channel area 52 for receiving the cover 42. It should be understood that when the cover 42 is received in the channel area 52, the sides 42a and 42b become associated with the sides 48a and 50a. It should be understood that the cover 42 is not directed permanently secured to the housing 32 after it is received in channel area 52. This feature permits the housing 32 secured to the housing 32 to migrate or float relative to the cover 42 even after the cover 42 is fixed to one or more of the spinal bones 10-16 as illustrated in FIGS. 6 and 20. As illustrated in FIG. 23, the sides 42a and 42b of cover 42 and sides 48a and 50a may be beveled and complementary to facilitate locating and mating engagement between the cover 42 and housing 32.

As illustrated in FIGS. 3-6 and 16-20, after the graft material 38 is placed in the housing 32 and the graft areas 35-36 (FIG. 17) defined by the housing 32 and adjacent spinal bones, then the cover 42 is situated between the walls or rails 48 and 50, as illustrated in FIGS. 6 and 19. The screws 46 may then be used to secure the cover 42 to one or more of the spinal bones 10-16 as illustrated in FIGS. 6 and 20. It should be understood that a feature of the invention is that the cover 42 facilitates aligning the housings 32 in a substantially co-lineal or relatively aligned position relative to each other and to the spinal bones 10-16, as illustrated in FIGS. 6,19 and 20. In the setting of multiple level discectomy, the floating cover 42 allows limited, controlled settling of the cages or housings 32 in the vertical plane with respect to the cover 42. As illustrated in FIGS. 6, 8,10 and 20, the cover 42 also provides means for providing a mechanical fixation of the adjacent spinal bones 10-16 relative to each other. Thus, while the housing 32 cooperates with adjacent spinal bones, such as spinal bones 10 and 12, to define a graft receiving area 34, the cover is multi-functional in that it not only covers the opening of any graft areas, such as area 34 (FIG. 17), but it also secures and retains the spinal bones 10-16 in a fixed spatial relationship relative to each other and relative to the housings 32. It should also be understood that the cover 42 may be fixed to one or more of the spinal bones 10-16 as may be desired to accomplish either of the aforementioned functions.

As illustrated in FIG. 11, note that the walls 48 and 50 further define projections 48b, 48c, 50b and 50c as shown. As illustrated in FIGS. 3-6 and 17-20, the projections 48b, 48c, 50b and 50c provide a plurality of migration preventers for preventing the housing 32 from migrating posteriorly in the direction of arrow A (FIG. 3) toward the spinal cord S or other neurological elements after the housing 32 is situated between the adjacent spinal bones 10-16 as illustrated. Further, the migration preventers 48b, 48c, 50b and 50c enable a surgeon to locate each housing 32 between adjacent spinal bones, such as spinal bones 10-16 in FIG. 1, and move the housing 32 in the direction of arrow A in FIG. 3 until the migration preventers 48b, 48c, 50b and 50c engage the surface 10a of spinal bone 10 and migration preventers 48b, 48c, 50b and 50c engage the surface 12a of spinal bone 12. As illustrated in FIG. 3, after the housings 32 are situated between the spinal bones 10-16 as shown, the migration preventers 48b, 48c, 50b and 50c facilitate preventing the third wall 32c from being over-inserted by the surgeon or from being over-inserted to a point where it engages the spinal cord S or other neurological elements.

Figure 26:
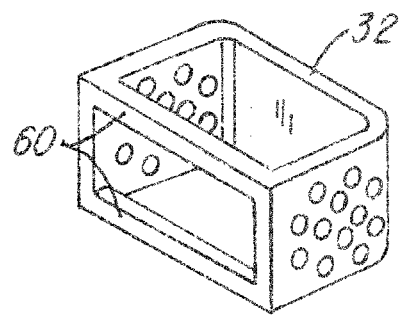
FIG. 26 is a view of another embodiment of the invention showing the crossbars integrally formed in the housing and without migration preventers.
Figure 29:
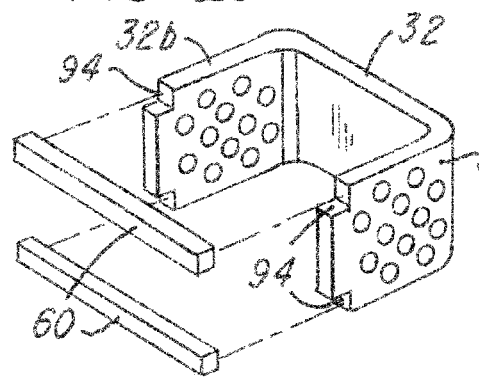
FIG. 29 is another view of the housing illustrating a plurality of removable crossbars without any migration preventers.
Figure 30:
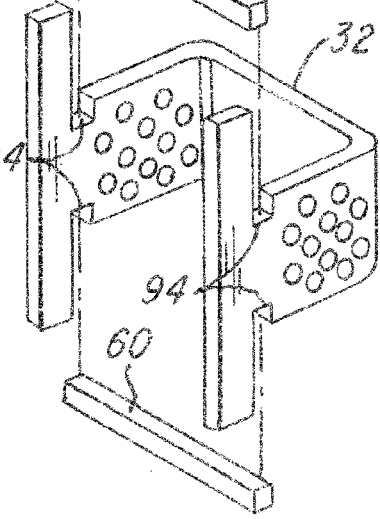
FIG. 30 illustrates another embodiment of the invention, similar to the devices illustrated earlier relative to FIG. 1-20 showing details of the cross bars and notches for receiving them.

The spinal fusion system 24 further comprises at least one migration stop or crossbar 60 as illustrated in FIGS. 11, 12, 29 and 30. The crossbar 60 may be either integrally formed in housing 32, as shown in FIG. 26, or separate as illustrated in FIGS. 11, 29 and 30, as illustrated in FIGS. 7, 12 and 14, for example. As illustrated in the exploded view in FIGS. 10 and 11, the surface 60a of crossbar 60 engages and cooperates with surface 42c of cover 42 to prevent anterior migration in the direction of arrow B). Thus, the spinal fusion system 24 of the embodiment being described provides means for preventing insertion of the housing 32 to a point where it might engage the spinal cord S (FIG. 3) or other neurological elements, such as dura mater, thecal sac, and also means for facilitating prevention of migration of the housing 32 in an anterior direction or in the direction of arrow B in FIG. 10 after the housing 32 is situated as described herein and the cover 42 is mounted to one or more of the spinal bones 10-16.

It should be understood that a plurality of the migration stops or cross bars 60 may be used alone or in combination with the migration preventers 48b, 48c, 50b and 50c. It should be understood that the stops 60 could be detachable, as shown in FIG. 26, or they could be integrally formed in housing 32 (as shown in FIG. 26). Also, these cross bars 60 may be removably received in the notched receiving areas 94 (FIGS. 29-30). For example, in anatomy that provided limited space, the surgeon may elect not to use housing with cross bars 60 or use a housing that does not have integrally formed cross bars.

The spinal fusion system 24 further comprises a system or means for preventing retraction or back out of the screws 46 after they are screwed into the spinal bones 10-16 in order to secure the cover 42 thereto. The spinal fusion system 24 of the present invention may be used with conventional screw lock devices or with a unique locking mechanism and system, which will now be described relative to FIGS. 21-23.

Figure 21:
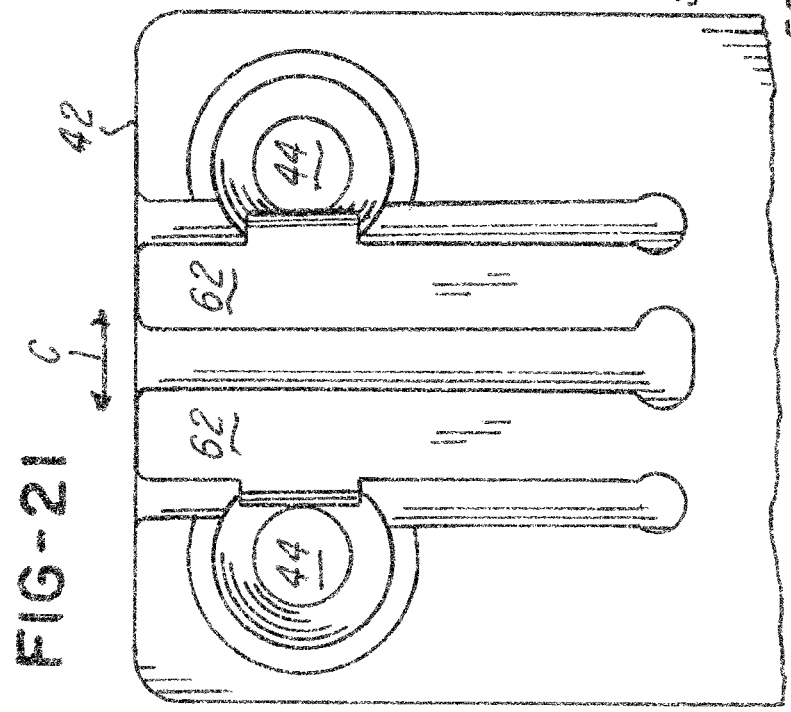
FIG. 21 is a fragmentary view illustrating various features of the cover.

As illustrated in FIGS. 21-23, the spinal fusion system 24 and, more particularly, cover 42 may be provided with at least one or a plurality of resilient detents 62 which are generally L-shaped as shown and are resilient so that they can move laterally in the direction of double arrow C in FIGS. 21-22 towards and away from a home position (FIG. 21) to permit the screws 46 first received in the apertures 44, and, second, locked into the cover 42. Thereafter, the screws 46 may be screwed into a spinal bone, such as spinal bone 10, and when a screw head 46*a* of the screw 46 engages a detent portion 62*a* of the resilient lock 62, the resilient lock 62 moves in a direction away from the apertures 44 until the screw head 46*a* clears the portion 62*a*. After a top surface 46*b* of the screw head 46*a* has cleared the bottom surface 62*a*1 (as viewed in FIG. 23) of portion 62*a*, the resilient lock 62 moves back toward aperture 44 to the home position until the portion 62*a* and surface 62*a*1 are operatively positioned over surface 46*b* of screw 46, thereby retaining and preventing the screws 46 from backing out of the cover 42 and thereby preventing the screws 46 from backing out of the spinal bone 10.

In the embodiment being described, the components of the spinal fusion system 24, such as the housing 32, first channel wall portion 48 and second channel wall portion 50, crossbar 60, cover 42 and screws 46 may be made of any desired composition or material such as a polymer, composite polymer, titanium, stainless steel, carbon fiber or other suitable material.

A method for fusing spinal bones together will now be described relative to FIG. 22. It should be understood that this procedure may be used during a vertebrectomy or discectomy or other neurological procedure during which it is desired to fuse spinal bones together. For ease of illustration, the embodiment will be described as used during a discectomy procedure during which the discs 18-22 (FIG. 1) are removed so that spinal bones 10-16 may be fused together. The procedure begins by situating a patient P on an operating table (not shown) and providing an appropriate incision as conventionally known to expose the spinal bones such as the spinal bones 10-16 illustrated in the side view shown in FIG. 1 and in the anterior view illustrated in FIG. 15. (Block 70 in FIG. 22). At Block 72, the vertebrae or discs, such as discs 18-22 in FIGS. 1 and 15, are surgically removed revealing the areas 26-30 in FIGS. 2 and 16. At Block 74, the housings 32 are inserted in the direction of arrow A (FIG. 3) into the areas 26, 28 and 30 until the migration preventers 40*b*, 48*c*, 50*c* and 50*d* engage the surfaces of the spinal bones 10-16, such as the surfaces 10*a* and 12*a* illustrated in FIG. 3. (Block 74 in FIG. 22). As mentioned earlier herein, the migration preventers facilitate preventing inserting the housing 32 to a point which would cause the third wall 32*c* to engage the spinal column S.

As illustrated in FIGS. 3 and 17, the housing 32 cooperates with adjacent spinal bones, such as spinal bones 10 and 12 to define the graft receiving area or cavity 34 in which the graft material 38 (FIG. 4) may be inserted. As mentioned earlier herein, these graft areas 34-36 may comprise a shape which is generally rectangular, as defined by the shape of the housing 32, but it could comprise another shape by simply providing a housing 32 having a different predetermined shape. Thus, the housing 32 may be provided in a circular or arcuate shape in which case the graft area 34 would define a generally circular or arcuate area, which would cause the graft material to form a similar shape. Other curved or multi-sided shapes may be defined by providing an appropriately or correspondingly shaped housing 32, depending on the selected or desired shape that the physician would like the fused graft material 38 to assume after it has fused to the adjacent spinal bones.

At Block 76, the graft material 38 is inserted and at Block 78, the cover 42 is situated in the slot or channel area 52 defined by the walls 48 and 50. As mentioned earlier herein, the cover 42 facilitates covering the openings, such as openings 34*a* and 36*a* of the graft areas 34 and 36, respectively. The surgeon secures the cover 42 to one or more of the bones, as illustrated in FIGS. 5-6 and 19-20 and then closes the patient (Block 80).

Figure 24:
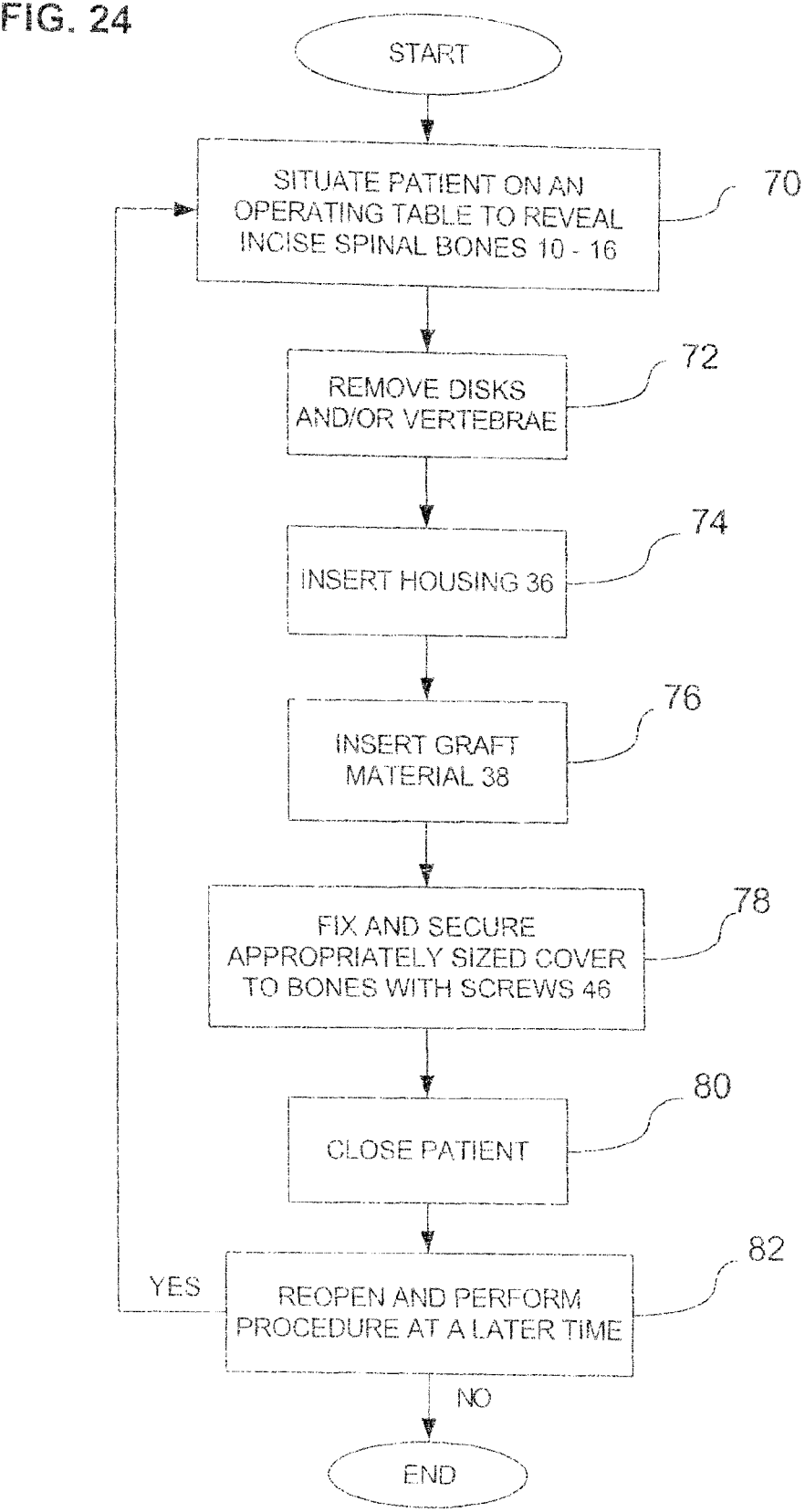
FIG. 24 is a schematic view of a process or method in accordance with an embodiment of the invention.

Again, and as mentioned earlier, a feature of the invention is that it provides a fixing system for fixing the location of the spinal bones 12-16 relative to each other. Simultaneously, the spinal fusion system 24 permits the housing 32 to "float" between adjacent bones, such as spinal bones 10 and 12 in FIGS. 3 and 6. This is advantageous for reasons mentioned earlier herein. Another advantage on this feature of the invention is that if it is necessary to operate on the same patient at a later time (Block 82 in FIG. 24) and, for example, add one or more housings 32 in order to fuse other spinal bones together, then the cover 42 can simply be removed at a later time, another discectomy or vertebrectomy performed and another housing 32 inserted. Another cover 42, or perhaps a second cover may then be used to seal the additional housing 32 after it is situated in the manner described herein. Thus, this invention provides a system and method, which is flexible and will permit the addition or insertion of additional housings 32 of the same or different sizes during a second operating procedure as illustrated in Block 82.

FIGS. 1-8 and 15-20 illustrate the general procedure and use of the invention in an illustrative discectomy wherein three discs are removed, replaced with housing 32, and graft material 38 inserted as described and cover 42 situated and mounted as described herein. In the illustration shown in FIGS. 1-8 and 15-20, three discs 18-22 are removed and the spinal bones 12-16 are fused together using the system and method as shown and described. It should be appreciated, however, that this system and method may be used with fewer or more housings 32 and with one or a plurality of covers 42 as may be desired or required. For example, if only one of the discs 18-22 needed to be excised and only two of the spinal bones 10-16 fused together, then only one housing 32 and cover 42 may be necessary. Likewise, as mentioned earlier herein, the housings 32 may comprise a different dimension or different height H (FIG. 14) to span a greater area, such as the area H4 illustrated in FIGS. 13 and 14. For example, FIGS. 13 and 14 illustrate a vertebrectomy wherein the spinal bone 12 has been removed along with the disc between spinal bones 14 and 16. This provides areas 80 and 81 in which an elongated housing 32', such as the housing 32' illustrated in FIG. 14 may be inserted. After the housings 32 and 32' are inserted between the spinal bones 10-14 and 14-16 as shown in FIG. 13, graft areas 82 and 84 are provided for receiving the graft material 38. As illustrated in FIG. 13, the cover 42 would have a corresponding elongated shape for fixing the spinal bones 10 and 14 together and for covering both openings 82 and 84 or housings 32 and 32'.

It is also anticipated that the invention may be used in a multitude of procedures, such as a vertebrectomy (FIGS. 8 and 9), discectomy (FIGS. 1-7, 13-20, or even a combination of a vertebrectomy and discectomy as illustrated in FIGS. 13-14. As mentioned and described earlier herein, a combination of different sizes of housings 32 and covers 42 may be used as shown. Although it is preferred that a single cover 42 be used, it may be desired in some applications to use multiple covers 42, such as where the removed discs are not adjacent.

In the illustrations being described, the housings 32 comprise the crossbar 60 which cooperate with the cover 42 to prevent anterior migration of the housing after the screws 46 are secured to the spinal bones as illustrated in FIGS. 6, 9 and 13.

Figure 25:
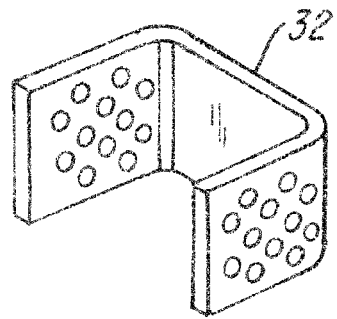
FIG. 25 illustrations another embodiment of the invention without crossbars or migration preventers.

FIGS. 25-30 illustrate other embodiments of the invention. In FIG. 25, a generally U-shaped housing 32 is provided without the walls 48 and 50 or crossbar 60. This embodiment may be useful. This may be useful if it were desired to insert housing 32 in local anatomy so that it could be loaded from the side or laterally, rather than anteriorly, as previously described.

In FIG. 26 a housing 32''' is provided with the crossbars 60, but without the walls 48 and 50. In this embodiment it may be useful to use such a housing design when the local anatomy provides limited space.

Figure 27:
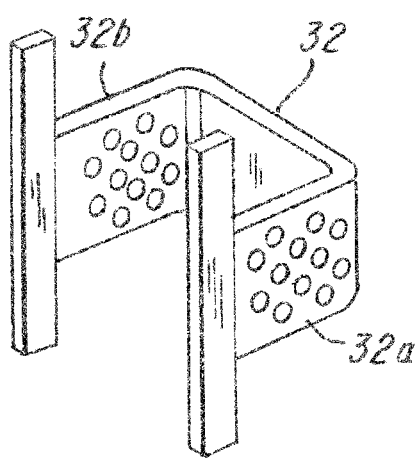
FIG. 27 is a view illustrating a plurality of migration preventers, without any crossbars.
Figure 28:
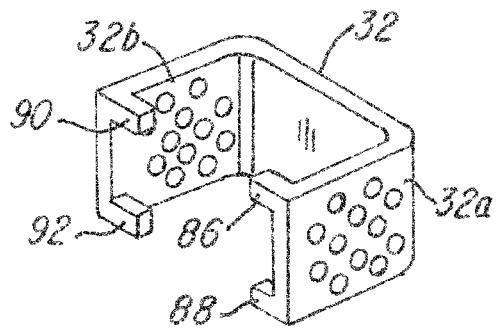
FIG. 28 is a view illustrating a housing with a plurality of projections which cooperate with the cover to prevent the housing from migrating anteriorly.

FIG. 27 illustrates yet another embodiment of the invention illustrating a housing 32 that is provided with a plurality of protrusion 86, 88, 90 and 92 that do not span completely between the walls 32b or 32a together but yet provide the protrusions 86-92 which will engage the cover 42 if the housing attempts to migrate anteriorly as described earlier herein. FIGS. 1-24, 29 and 30 show embodiments of the invention where the crossbars 60 are not integrally formed with the housing 32, but received in the notched areas 90 as shown. As mentioned earlier, the crossbars 60 may be separate or may be integrally provided with the housing 32. Providing detachable crossbars 60, such as is shown in the embodiments illustrated in FIGS. 25, 28 and 29, enable the walls 32a and 32b to flex towards and away from each other. The housing 32 may be provided with a malleable material in which case the surgeon can change the general U-shape of the housing 32 to accommodate the size or shape of the areas 34 and 36 (FIG. 17). In the embodiment described, housing 32 and cover 42 may be made of titanium, polymer or a bioresorbable material.

FIG. 31 illustrates the walls 48 and 50 having notched areas 49 and 51 for receiving the cover 42 which is dimensioned to fit, thereby eliminating the need for cross bars 60.

FIGS. 32-36 illustrate another embodiment of the invention. In this embodiment, those parts that are the same or similar to the parts illustrated in FIGS. 1-30 are identified with the same part number. except that the parts in FIGS. 31-36 have an apostrophe ("'") mark added thereto.

In this embodiment, the spinal bones 10 comprises a cover 400 for situating in the channel area 52 (FIG. 11) to facilitate preventing interior migration of the graft material 38. In order to secure the cover 400 over the graft area 38, a locking system, means and method are provided for retaining the cover 400 on the housing 32. In the embodiment being described, the locking system 402 comprises a plurality of screws, fastening means or fasteners 404, 406, 408 and 410 that are received in openings, such as openings 405 in the cover plate 400 as shown. Note that the fasteners 404-410 comprise a plurality of female openings or slots 404a, 406a, 408a and 410a for receiving a tool, such as a hex wrench for tightening and loosening the fasteners 404-410.

In the embodiment being described, the fasteners 404 and 408 comprise a head 404b and 408b that have a planar or flat portion 404b1 and 408b1 as shown. As best illustrated in FIGS. 34 and 35, note that the fasteners 408 and 410 each comprise threads or a threaded portion, such as threads or portions 408c and 410c of fasteners 408 and 410, respectively. Note that a distance or small radius D1 between center C1 and edge, 408b1 in FIG. 34 is smaller than the distance or large radius D2 measured by the distance between center C1 and edge 408b1 in FIG. 34. The difference in the distances D1 and D2 facilitates defining a cam surface or lobe on the wall 408b2 whose use and purpose will be defined later herein.

In the embodiment being described, one or more of the heads 404b, 406b, 408b and 410b may comprise an indicia, such as a grind mark or other indicator 412 and 414 (FIG. 32), to facilitate and assist a user, such as a doctor, to identify the small radius portion D1 during a surgical procedure. Thus, the indicia 412 and 414 facilitate defining the surface associated with the flat portion, such as portion 404b1.

It should be understood that when the pairs of fasteners 404-406 and 408-410 are aligned such that the surfaces 404b1 and 408b1 and short or small radius portion D1 are situated in opposite or closest to wall 406b of screw 406 and wall 410b of screw 410 the adjacent fasteners 406 and 410 respectively, may be rotated and screwed into, for example, vertebrae 10, which will secure and retain the cover 400 over the graft area 38. Although not shown, the locking system of the present invention may comprise eccentric fasteners of screws having eccentric heads (i.e. where a head center is offset from a thread axis) and fasteners that are used with non-eccentric fasteners. For example, and as illustrated in FIG. 33, fasteners 404 and 408 may comprise the aforementioned eccentric, while adjacent fasteners 406 and 410, respectively, may be non-eccentric fasteners or screws.

In any event, the small radius portion D1 permits the adjacent fastener or screw such as screw 410, whether it has an eccentric or not, to be turned when the small radius portion D1 or flat portion 408b1 is situated in opposed relationship to the adjacent screw (as illustrated in FIGS. 32 and 34). For example, FIG. 34 illustrates that when the fasteners are aligned such that the indicia 414 are aligned as illustrated in FIG. 32, a gap G exists between the portions 408d1 and wall 410d of screw 410 as shown. The gap G permits either or both of the fasteners 408 and 410 to rotate in either a counter-clockwise or clockwise direction during fastening and unfastening of the fasteners to the vertebrae as described earlier herein with the prior embodiments.

When it is desired to secure the cover 400 over the housing 32, the fasteners 404-408 are placed in the cover and aligned as illustrated in FIG. 32. The fasteners 404-408 are rotated and screwed into vertebrae 10 in a clockwise direction until it is seated. These fasteners 404 and 408 are then "backed out" less than a full turn until flat surface 404b1 and 408b1 are aligned as shown in FIG. 32. The surgeon may use the indicator 412 and 414 to perform this alignment. This alignment presents the gap G (FIG. 34), which permits the fastener 410 to be rotated in a clockwise direction until completely screwed into vertebrae 10.

Next, the adjacent fastener (406 for the 404-406 pair and 410 for the 408-410 pair) is inserted into opening 405 in cover 400 and in FIG. 32 and 34 until they are fully seated into the vertebrae 10. For example, in the illustration shown in FIGS. 32 and 34, the fastener 408 is rotated in a clockwise direction with a tool, such a hex wrench (not shown) until it is fully seated into the vertebrae 10.

The fastener 408 is again rotated in the clockwise direction (as viewed) until the large radius portion D2 and the wall portion 408b2 engages and comes against the wall 410b of the fastener 410.

It should be appreciated that when the fasteners 404-410 are secured in the locked position in the manner described, they facilitate retaining themselves in the locked position. For example, if fastener 410 begins to rotate in a counterclockwise direction (as viewed in FIG. 33) it will cause fastener 408 to rotate in a clockwise direction which, in turn, causes fastener 408 to tighten and resist the counterclockwise rotation of fastener 410. If fastener 410 would rotate, fastener 408 would screw deeper into the vertebrae 10.

FIG. 36 is an illustration similar to FIG. 11 showing the orientation and alignment of the cover 400 and fasteners 404-410 to the housing 32.

FIGS. 37-44D show further embodiments illustrating several different plates or covers, such as a plate or cover 500 (FIG. 37), 600 (FIG. 40A), 700 (FIG. 41 A), 800 (FIG. 42A), 900 (FIG. 43A) and 1000 (FIG. 44A), each of which comprises an integral lock 501 similar to the resilient lock 62 relative to the embodiment illustrated in FIGS. 21-23.

Referring to FIGS. 37, 38A-38E and 39A-39E, a system and method are shown for facilitating and retaining the plate or cover to the spinal bones, such as spinal bones 10,12,14 and 16. In this embodiment, the implant cover or plate 500 comprises the plurality of apertures 502, 504, 506, 508, 510, 512, 514 and 516, each of which are capable of receiving a screw 540. The plate 500 has a plurality of integral locks, resilient detents or flexible fingers 520, 522, 524, 526, 528, 530, 532 and 534 associated with the apertures 502-516 as shown. In this embodiment, note that each of the plurality of integral locks, resilient detents or flexible fingers 520, 522, 524, 526, 528, 530, 532 and 534 are integral with the plate 500 and are resilient and flexible as with the prior embodiments. For ease of description, the structure and function of one of the integral locks, resilient detents or flexible fingers and associated aperture, namely detent or finger 520 of plate 500 and aperture 502 will be described. However, it should be understood that the plurality of apertures and associated plurality of detents and flexible fingers in the embodiments shown in the embodiments in FIGS. 40A-44D are substantially the same in structure and function.

In the illustration shown in FIGS. 37-39I, notice that the plate or cover 500 comprises a plurality of screw-receiving areas, such as apertures 502 and 504. Notice in FIG. 38A that each of the plurality of resilient detents or flexible fingers, such as finger 520, are defined by a cut-out portion, channel or area, such as area 529, that facilitates defining the resilient detent or flexible finger 520. Notice also that the cut-out area or channel 529 is in communication with the screw-receiving aperture or area 502 and also the window area 521 as shown. Notice that the channel area 529 is generally curved or arcuate and the resilient detent or flexible finger 520 comprises a similar or complementary curved or arcuate shape. It should be understood that the channel 529 enable the plurality of resilient detents or flexible fingers, such as fingers 520 and 522, to move toward and away from an axis of its the screw-receiving aperture or area, such as areas 502 and 504, respectively. A plurality of cut-out areas, apertures or channels, such as areas 527 and 529, are in communication with the areas 502 and 504, respectively, and facilitate providing or defining the plurality of resilient detents or flexible fingers 520 and 522, respectively. As with embodiments previously described, note that the integral portion 520a is integrally formed into plate 500, so the plate 500 and integral fingers are a one-piece construction, as with the embodiment shown and described relative to FIGS. 21-23. Also, as with the embodiment illustrated in FIGS. 21-23, note that each resilient detent or flexible finger 520 is capable of flexing or moving toward and away from aperture 502 as will be described later herein. Note that the screw 540 comprises the screw head 540a that comprises a camming portion 540a1 and a shoulder portion 540a2 as shown.

Figure 37:
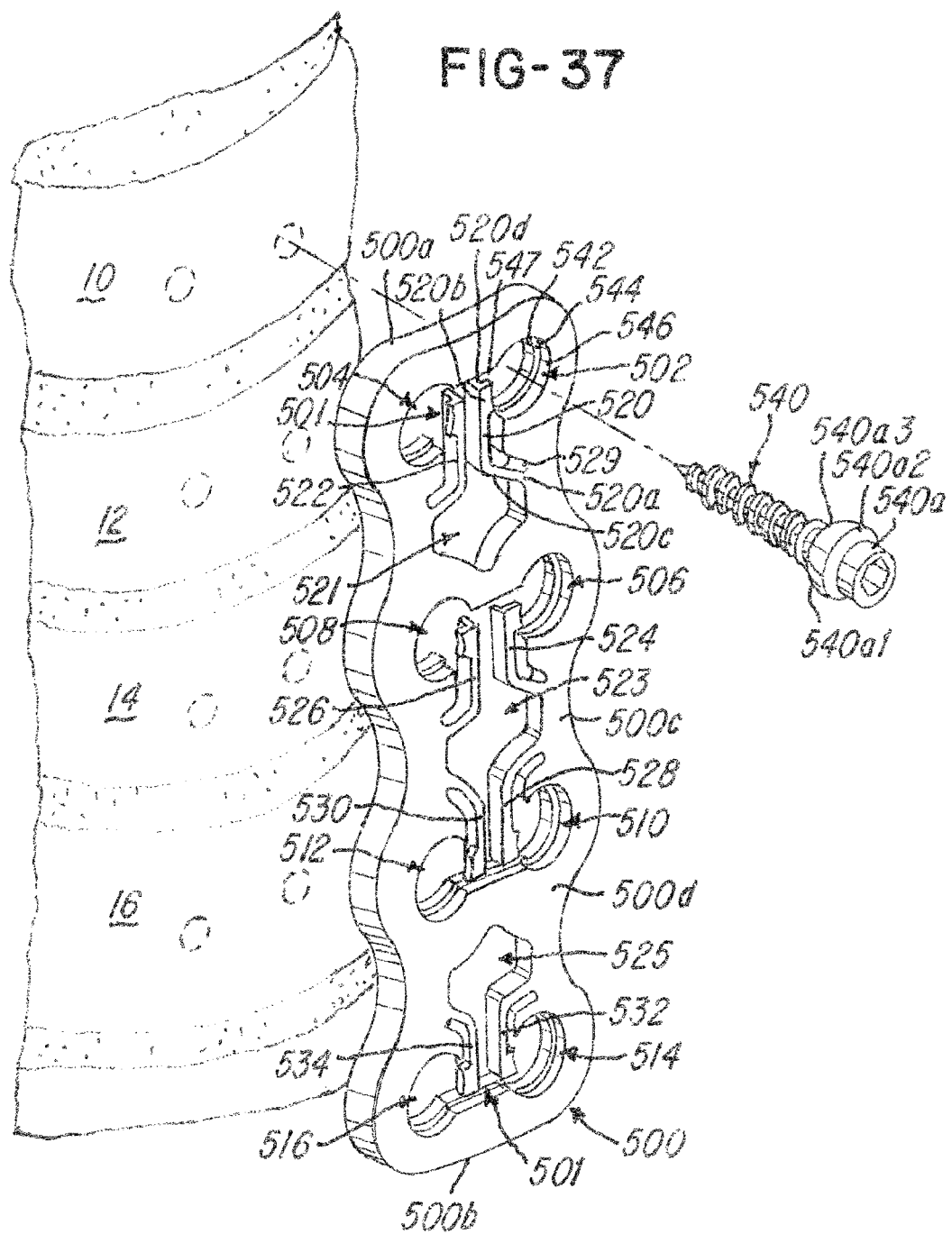
FIG. 37 is perspective view of another embodiment of the invention.

Each of the plurality of resilient detents or fingers, such as finger 520 in FIGS. 37 and 38A, comprises an integral portion 520a that is integral with the plate 500, a detent portion 520b, and a joining portion 520c that joins the detent portion 520b and integral portion 520a as shown. In this embodiment, notice that the detent portion 520b is situated toward an end 520d of the resilient detent or finger 520. Note that each of the plurality of resilient detents or flexible fingers 520, 522, 524, 526, 528, 530, 532 and 534 are not linear and the joining portion 520c comprises the curved or arcuate shape mentioned earlier, which facilitates or causes the detent portion 520b to become operatively positioned in or near the screw-receiving aperture 502 as shown. Thus, each resilient detent or finger 520 comprises a configuration and shape that causes the detent portion 520b to be associated with at least one of the apertures or screw-receiving areas, such as screw-receiving area 546, as shown. Note that each of the screw-receiving apertures or areas 502-516 each have at least one of the resilient detents or flexible fingers 520-534, respectively, associated therewith as shown. As mentioned earlier, the screw-receiving area 502 is capable of receiving a screw 540 that secures or fastens the plate 500 to the spinal bone 10 in the illustration in FIG. 37.

Each plate or cover 500 may comprise at least one or a plurality of windows, such as windows 521, 523 and 525 (FIGS. 37 and 38A), in an interior area 500c of the plate 500. The at least one or plurality of windows 521, 523 and 525, enable the surgeon to view the grafting areas, such as areas 26, 28 and 30 in FIG. 16, during the surgical procedure.

In the embodiment illustrated in FIG. 37-39I, the plate or cover 500 comprises a first end 500a, a second end 500b and the interior area 500c that joins the first and second ends 500a and 500b. In the embodiment illustrated, a first pair of resilient detents or fingers, namely fingers 520 and 522, is situated toward the first end 500a in association with apertures 502 and 504, respectively, as shown. A second pair of resilient detents or fingers 532 and 534 is situated toward the second end 500b in association with apertures 514 and 516, respectively. FIG. 37 illustrates two other pairs of resilient detents or flexible fingers 524, 526, 528, 530 and 532, 534, respectively. Note that the pairs, 524, 526 and 528,536 are situated in the interior area or portion 500c of plate 500.

Referring to FIG. 37, 38A, 39B, 39C, 39E, 39F, 39H and 39I, the aperture 502 is defined by a generally cylindrical wall 546 defining a circumference that is not endless. The wall 546 terminates at an open area or opening 547. Notice that the resilient detent or flexible finger 520 is configured and comprises the shape mentioned earlier that facilitates causing detent portion 520b to become operatively positioned in or associated with the opening 547 so that it can cooperate with and/or engage the screw 540 to retain and lock the screw 540 in the plate 500, thereby preventing the screw 540 from backing out of the spinal bone 10 to which it is secured. The plate 500 also comprises a second wall 542 having a smaller diameter than the wall 546. The second wall 542 also terminates at the opening 547 and provides a shoulder 544 that defines a seat that engages and supports a bottom portion 540a3 of screw head 540a. Notice that in the illustrations shown in FIGS. 37-42D, it is contemplated that a screw 540 be inserted into each of the screw-receiving apertures. The operation of the resilient detent or flexible finger 520 and screw 540 will now be described.

As mentioned earlier, the plate or cover 500 comprises the screw-receiving aperture or area 502 that receives the screw 540 as shown in FIG. 39D. As the screw 540 is screwed into the spinal bone 10, the screw 540 moves or is screwed in the direction of arrow D in FIG. 39D. As the screw 540 moves in the direction indicated by arrow D, notice that a bottom portion 540a3 of screw head 540a engages a top surface 520e of the resilient detent or flexible finger 520, as illustrated in FIGS. 39D-39E. In the illustration being described, notice in FIGS. 39B, 39C, 39F and 39I, that the detent portion 520b is generally L-shaped in cross-section and comprises the first leg portion 520b and the second leg portion 520b2. As the screw 540 continues to be screwed into the spinal bone 10, a shoulder 540a2 of screw head 540a engages a side wall 520b1 of the second leg portion 520b4 of locking or detent portion 520b and forces it to move or flex in the direction of arrow E in FIG. 39D. It should be understood that each of the plurality of resilient detents or flexible fingers, including the finger 520, in plate 500 is generally biased to a home position, illustrated in FIGS. 37, 38A and 39A-39C. As the screw 540 moves farther into aperture 502, the finger 520 is caused to flex or move away from its home position. In this regard, notice that the camming portion 540a1 of screw head 540a defines or provides a rounded engaging or camming surface that acts against and engages the flexible fingers 520 and forces it to move in the direction of arrow E, as illustrated in FIG. 39D.

After the portion or surface 520b2 of detent portion 520 clears the shoulder 540a2 of the screw head 540a, as illustrated in FIGS. 39G, 39H and 39I, the generally planar portion or surface 520e of detent portion 520b flexes, moves or returns in a direction opposite arrow E (FIG. 39D) and toward the home position, at which time the surface 520b1 comes into proximity with or engages a generally cylindrical wall 540a3 of screw head 540a. Notice in FIG. 39D that the wall 520b1 may have a curvature or curved surface that generally corresponds to a circumference or curvature of the cylindrical wall 540a3 in order to facilitate enabling the head 540a to be screwed or rotated while the wall 540a3 engages, rides along or follows the surface 540a3.

A bottom surface 520b2 (FIG. 39C, 39E, 39F and 39I) of the detent portion 520b becomes operatively associated with and opposed to the shoulder 540a2, as illustrated, for example, in FIGS. 39C, 39F and 39I. Notice that the dimension SD (FIG. 39F), which is a width of the shoulder 540a2, generally corresponds to a dimension DD (FIG. 39F), which is a cross-sectional width of a portion of the detent portion 520e.

After the resilient detent or flexible finger 520 moves, flexes or returns to the home position illustrated in FIGS. 39A and 39B, the surface 520b2 of leg portion 520b becomes operatively related and generally opposed to the shoulder 540a2 as shown, thereby locking the screw 540 to the plate or cover 500 and retaining the screw 540 in a locked position in the spinal bone, such as the spinal bone 10, so that it cannot back out of either the plate 500 or the spinal bone 10 to which it is attached.

In the embodiment being described, and as mentioned earlier, the plurality of the resilient detents or flexible fingers 520-534 are provided in a plurality of pairs, such as the pairs 520, 522; 524, 526; 528, 530; and 532, 534 as shown in FIG. 37. In the illustration being described relative to FIG. 37 and 38A-38E, each of the resilient detents or flexible fingers making up the pairs is associated with at least one of the plurality of apertures 502-516, respectively, as shown.

The plate or cover 500 further comprises the plurality of windows or window areas 521, 523 and 525 mentioned earlier. Note that each of the plurality of window areas 521, 523 and 525 are defined or bounded at least in part by at least one or a plurality of the resilient detents or fingers 520-534 in the illustration being shown. For example, one or more of the window areas 521, 523 and 525 may be bounded by and in communication with the integral portion 520a and joining portion 520c of one or more of the resilient detent or flexible fingers 520-534. Thus, as illustrated in FIG. 38A, notice that the area or window area 521 is bounded or defined at least in part by the walls 500e, 500f, 500g and 500h and also the surfaces or walls 520a1 and 522a1. Likewise, the middle window 523 is bounded by the surfaces or walls 524a1, 526a1, 500i, 530a1, 528a1 and 500j. Alternatively, notice in the embodiment shown in FIG. 42A, an interior window 837 may be provided that is not partially bound by any portion of any resilient detent or fingers.

One advantage or feature of the windows, such as window area 531, is that it permits easy access and visualization to the associated graft area, such as area 28.

In the illustration being described, the plate or cover 500 may be curved or crowned along its length (FIG. 38C) and/or its width (FIG. 38D) to conform or complement the shape of the spinal bones 10-16. Notice that a front side 500d of plate 500 may be generally smooth and have a curved or beveled edge 548 (FIG. 38C) as shown. A back or rear side 500e (FIG. 38B) may comprise serrated areas 549 that facilitate retaining the plate or cover 500 in a secure position against the spinal bones 10-18. FIG. 38E illustrates a cross-sectional, enlarged and fragmentary view of the serrated areas 549.

It should be understood that the plate 500 may be provided with less or more apertures and associated resilient detents or fingers, and FIGS. 40A-44D illustrate several other illustrative embodiments. Similar parts and components in these embodiments bear the same part number, except that part numbers in the other embodiments are incremented by 100. For example, the shoulder 544 in FIG. 38A is substantially the same and operates in the same manner as the shoulder 644 in FIG. 40A.

In the illustration shown in FIG. 40A-40D, notice that plate 600 comprises two pairs of apertures 602, 604 and 614, 616. The apertures 602, 604, 614 and 616 have associated pairs of resilient detents or flexible fingers, namely, fingers 620, 622, 632 and 634, respectively, as shown. Thus, each of the screw-receiving apertures or openings in this embodiment has a corresponding resilient detent or finger associated therewith, as with the other illustrative embodiments. Notice in the embodiment illustrated FIGS. 40A-40D that the plate or cover 600 comprises only one open area or window 623 defined at least in part by the joining portions 620c, 622c, 632c and 634c. This embodiment may be useful, for example, when affixing the plate or cover to just two adjacent bones.

FIGS. 41A-41D are yet another illustrative embodiment showing a plate or cover 700 having three pairs of apertures 706, 708; 710, 712; and 714, 716, with each aperture having an associated resilient detent or flexible fingers 724, 726, 728, 730, 732, and 734, as shown. Notice that each of the screw-receiving apertures or areas 806, 808, 810, 812, 814, 816 is in communication with at least one window, such as windows 823 and 825.

FIGS. 42A-42D illustrate another embodiment with five pairs of aperture, namely apertures 806, 808; 810, 812; 814, 816; 806, 808; and 810, 812 with each aperture having an associated resilient detent or finger 820, as shown.

Thus, it should be understood that the plate or cover may have more or fewer screw-receiving apertures, resilient detents or flexible fingers and windows depending upon the application. Although not shown, some of the apertures may be provided without a resilient detent or finger or with multiple resilient detents or fingers, although it is preferred and each screw-receiving aperture or area has an associated detent, lock or finger. Also, the plate or cover may be provided with more or fewer windows 821, 823 and 825.

In the illustrations being described, note that each of the screw-receiving apertures, and associated detents, such as aperture 502 and detent 520 in FIG. 37, is in communication with at least one window. For example, note that the window 521 in FIG. 37 is in communication with the screw-receiving apertures or areas 502 and 504. Note that the bottom window 725 in FIG. 41A is in communication with the bottom pair (as viewed in FIG. 41A) of screw-receiving apertures or areas 714 and 716 as shown.

The embodiments illustrated in FIGS. 37-39I, 40A-40D and FIGS. 41A-41D are suitable for use as prosthetic implants that will be secured into multiple spinal bones, such as spinal bones 10 and 12 or spinal bones 10,12 and 14 (FIG. 37). These illustrations contemplate that a plurality of pairs of screws 540 will be used to secure the plate or cover to each spinal bone, such as spinal bones 10,12,14 and 16 (FIG. 37). However, a plate and an integral lock that utilizes a single screw for each spinal bone is also contemplated. This will now be described relative to FIGS. 43A-44D.

As illustrated in the embodiment shown in FIGS. 43A-43D, the plate or cover 900 comprises apertures 902 and 904. A plurality of integral resilient detents or flexible fingers 920 and 922, respectively, are configured and have detent portions 920b and 922b that are operatively associated with the apertures 902 and 904 as shown. As with prior embodiments, the resilient detents or flexible fingers 920 and 922 comprise the same components and are formed and function in the same manner as the finger 520 described earlier. The fingers 920 and 922 provide integral locks for retaining the screw, such as screw 540, in the locked position in the plate 900 and spinal bone, such as spinal bone 10,12,14 or 16 illustrated in FIG. 37.

FIGS. 44A-44D illustrate yet another embodiment wherein the plate or cover 1000 comprises a plurality of apertures 1002, 1004 and 1006 as shown. Notice that the apertures 1004 and 1006 are in communication with a window 1021. As with the embodiment described earlier relative with FIGS. 43A-43D, notice the embodiment shown in FIGS. 44A-44D also comprise the plurality of resilient detents or flexible fingers 1020 and 1022, respectively, that are in operative relationship with the plurality of screw-receiving areas or apertures 1004 and 1006, respectively as shown. As with the illustration shown in FIG. 43A, each of the plurality of resilient detents or flexible fingers, such as finger 1020, comprises the integral portion 1020a, a detent portion 1020b and a generally curved joining portion 1020c as shown. The plurality of resilient detents or flexible fingers 1020, 1022 and 1034 and associated components, such as integral portions 1020a-1020c associated with finger 1020 function in substantially the same manner as the resilient detents or fingers 520 and associated components shown and described earlier relative to FIG. 37.

Advantageously, the embodiments illustrated in FIGS. 43A-43D and FIGS. 44A-44D provide plates or covers 900 and 1000 that utilize a single screw 540 to secure the plate or cover 900 and 1000 to each of the spinal bones, such as spinal bones 10, 12, 14 or 16, while also having at least one integral lock, resilient detent or flexible finger 920, 1020 associated with each screw 540 for retaining or locking the screw 540 in the plate or cover. As with embodiments illustrated in FIGS. 37-42D, the embodiments illustrated in FIGS. 43A-44D may optionally include at least one window, such as window 1021 shown in FIG. 44A, mentioned earlier, that are in communication with one or more of plurality of screw-receiving areas or apertures.

Advantageously, the illustrations in FIG. 37-44D show a one-piece integral plate comprising at least one or a plurality of integral locks manufactured from a single material to provide a one-piece plate. The plate may be made from titanium, titanium alloy, carbon fiber, polymer or other biocompatible material.

Advantageously, the various embodiments of the invention provide a system and method for inserting graft material 38 into a graft area 34 and 36 (FIG. 17) to fuse a plurality of bones such as spinal bones 10-18 together. The system and method also provide means for fixing the spinal bones 10-18 relative to each other, while permitting the housing 32 to cooperate with adjacent bones 10-18 to define a graft area 34 and 36 (FIG. 17) and to also float relative to the cover 42. The locking system illustrated in FIGS. 21-23 further facilitates providing a locking system that does not require the use of any tools, yet prevents back out of the screws 46.

Referring now to FIGS. 45-48I, another embodiment is shown illustrating a system and method for facilitating retaining a plate or cover to the spinal bones, such as spinal bones 10,12,14 and 16.

In this embodiment, a plate or cover 1100 is provided with at least one or a plurality of locks, integral locks, resilient detents or flexible fingers 1120, 1122, 1124, 1126, 1128, 1130, 1132 and 1134 are integral with the plate 1100 and are resilient and flexible as with the integral locks, flexible fingers or resilient detents in prior embodiments. However, as illustrated in FIGS. 45-49, this embodiment comprises a ratchet and pawl lock, detent or means for preventing movement of a screw 1140 along its axis as well as rotational movement of the screw 1140 in at least one or a plurality of directions, such as a counter-clockwise direction or a clockwise direction. For ease of description and illustration, the structure, function and features of a pair of the integral locks, resilient detents or flexible fingers and associated aperture, namely fingers 1120 and 1122, will be described. However, it should be understood that the plurality of apertures, associated plurality of detents, integral locks and flexible fingers 1124-1134 in the embodiments shown in FIGS. 45-49 are substantially similar in structure, operation and function as the fingers 1120 and 1122.

Figure 45:
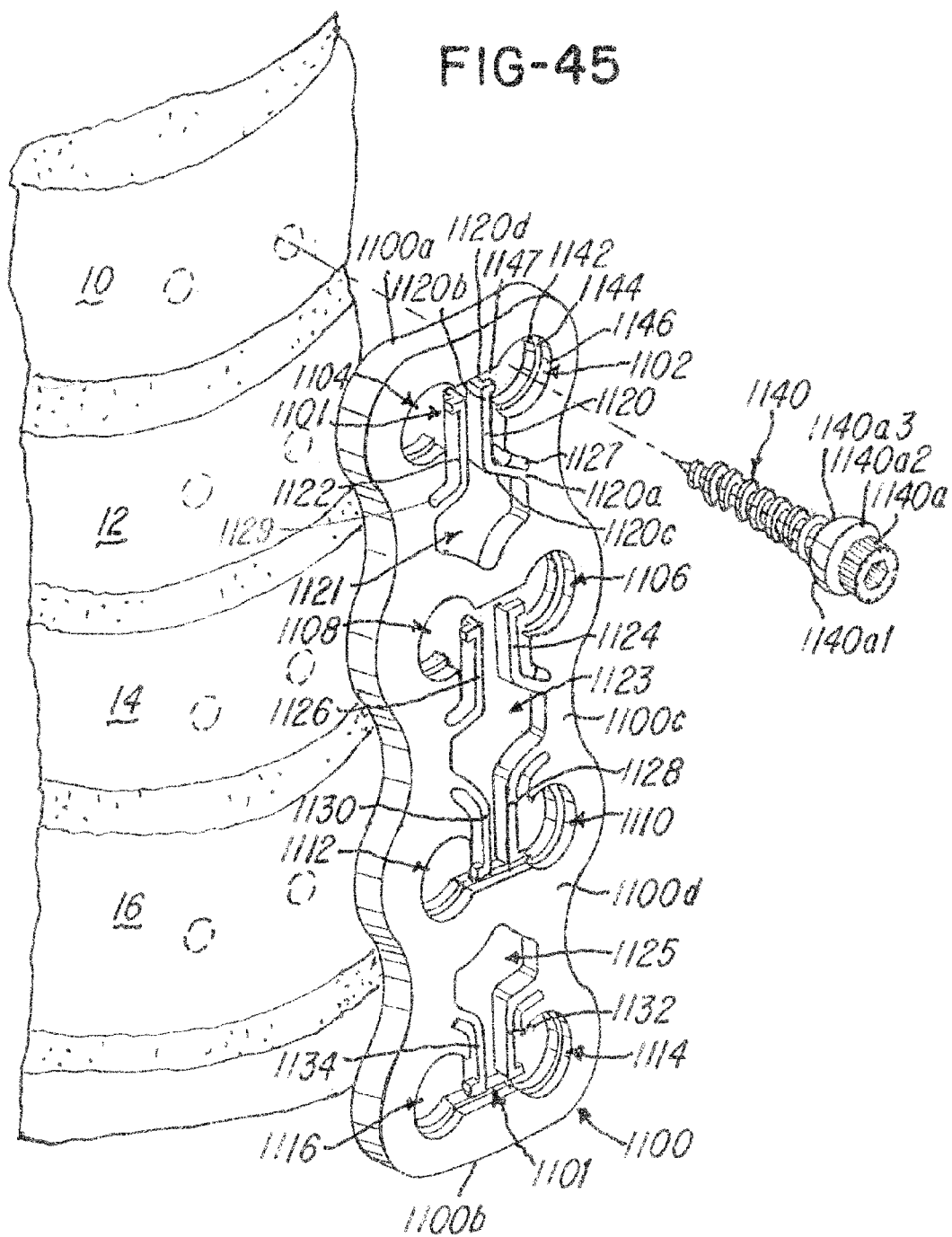
FIG. 45 is a perspective view of another view of the embodiment of the invention.

In the illustration shown in FIGS. 45-46A, notice that plate 1100 comprises a plurality of screw-receiving openings, apertures or areas, such as apertures 1102 and 1104. Notice in FIG. 45 that each of the plurality of resilient detents or fingers 1120-1134, such as finger 1120, is defined by a cut-out portion, channel or area, such as area 1129 (FIG. 48A) that facilitates defining the resilient detent or flexible finger 1120. Notice also that the cut-out area or channel 1129 is in communication with the screw-receiving aperture or area 1102 in the window area 1121 as shown. Notice that the channel area 1129 is curved or arcuate and resilient detent or flexible finger 1120 comprises a similar complementary curved or arcuate shape. It should be understood that the channel 1129 enables the plurality of resilient detents or flexible fingers, such as fingers 1120 and 1122, to move toward and away from an axis of its respective screw-receiving aperture or area, such as areas 1102 and 1104 (FIG. 45), respectively. A plurality of cut-out areas, apertures or channels, such as areas 1127 and 1129 are in communication with the areas 1102 and 1104, respectively, and facilitate providing or defining the plurality or resilient detents or flexible fingers 1120 and 1122, respectively. As with the embodiments previously described, note that an integral portion 11 20a is integrally formed into the plate 1100, so that the plate 1100 and integral fingers are a one-piece construction, as illustrated with prior embodiments. Also, with the embodiments illustrated previously herein, note that each of the resilient detents or flexible fingers 1120 may flex or move toward and away from aperture 1102 as will be described later herein.

Each of the plurality of resilient detents or flexible fingers, such as finger 1120 in FIG. 45, comprises an integral portion or detent 1120b, a joining portion 1120c that integrally joins the detent portion 1120b to the portion 1120a as shown. In this illustration, notice that the detent portion 1120b is situated toward an end or surface 1120d of the resilient detent or finger 1120. Note that each of the plurality of resilient detents or flexible fingers 1120, 1122, 1124, 1126, 1128, 1130, 1132, and 1134 are resilient and flexible and are not linear, and their respective joining portion, such as 1portion 1120c per detent 1120, comprises the curved or arcuate shape mentioned earlier. This shape facilitates or causes the detent portion 1120b to become operatively positioned at or near the screw-receiving aperture 1102 as shown. Thus, each resilient detent or finger, such as finger 1120, comprises a configuration and shape that causes the detent portion 1120b to be associated with at least one of the apertures or screw-receiving areas, such as screw-receiving area 1102 as shown.

Each of the screw-receiving apertures or areas 1102-1116 have at least one of the resilient detents or flexible fingers 1120-1134, respectively, associated therewith as shown. As with prior embodiments, each screw-receiving area 1102-1116, such as screw-receiving area 1102, is capable of receiving a screw 1140 that secures of fastens the plate 1100 to the spinal bone, such as spinal bone 10, in the illustration in FIG. 45.

The plate or cover 1100 may comprise at least one or a plurality of windows, such as windows 1121, 1123 and 1125 (FIG. 45), and an interior area or portion 1100c of the plate 1100. The at least one or plurality of windows 1121, 1123 and 1125 enable the surgeon to view the grafting areas, such as receiving areas 26, 28 and 30 in FIG. 16, during a surgical procedure.

In the embodiment in FIGS. 45-48I, the plate or cover 1100 comprises a first end 1100a, a second end 1100b and the interior portion 1100c that joins the first and second ends 1100a and 1100b. In the embodiment illustrated, a first pair of resilient detents or fingers, such as fingers 1120 and 1122, are situated toward the first end 1100a in association with the apertures 1102 and 1104, respectively, as shown. The second pair of resilient detents or fingers 1132 and 1134 are situated toward the second end 1100b in association with apertures 1114 and 1116, respectively. FIG. 45 illustrates other pairs of resilient detents or flexible fingers 1124, 1126; 1128, 1130; 1132 and 1134, respectively. Note that the pairs 1124, 1126, and 1128, 1130 are situated in the interior area or portion 1100c of the plate 1100.

Referring to FIGS. 45-48I, the aperture 1102 is defined by a generally cylindrical wall 1146 defining a circumference that is not endless. Similar to prior embodiments, the wall 1146 terminates at an open area or opening 1102. Notice that the resilient detent or finger 1120 is adapted to and comprises the shape mentioned earlier that facilitates causing the detent portion 1120 to become operatively positioned in or associated with the opening 1102 so that it can cooperate with/and engage the screw 1140 to retain and lock the screw 1140 in the plate 1100, thereby preventing the screw from rotating or moving away from the plate 1100 or from backing out of the spinal bone 10 to which it is secured.

In this illustration, note that the screw 1140 comprises a screw head 1140a that comprises a camming portion 1140a1 (FIG. 46B) and a shoulder portion 1140a2, which operate and function similar to the camming portion 540a1 and shoulder portion 540a2, respectfully, mentioned earlier herein. As illustrated in FIGS. 46A-48I, notice that the screw head 1140a further comprises a ratchet portion 1140a3 having a plurality of ratchets, teeth or angled tooth surfaces, such as teeth 1140a3i and 1140a3ii, situated adjacent the shoulder portion 1140a2 as shown.

Notice in the embodiment shown in FIGS. 47A and 47B that the integral lock, resilient detent or flexible fingers 1120 and 1122 each comprise or define a pawl 1122b having a beveled surface 1120b3, respectively. Each also comprise a latch or detent 1120c and 1122c edge or surface that cooperates with the ratchet teeth or surfaces, such as surfaces 1140a3i and 1140a3ii, to prevent movement in a counter-clockwise direction of arrow A in FIG. 47A as shown.

Notice that the ratchet teeth on the head 1140a are generally angled in an opposite direction that the screw 1140 will rotate as shown in FIG. 47A. As with the screw 1140 associated with detent 1122, the screw 1140 associated with the detent 1120 is permitted to rotate in a clockwise direction, but restricted from movement in a counter-clockwise direction as shown. If it is desired to remove a screw 1140 from a bone, the detents 1120b and 1122b are moved or caused to be held open (that is, moved away) from the screw 1140 and, the screw 1140 unscrewed.

Notice that an angle Θ of the surface 1141 (FIG. 47A) of one tooth 1140a3i relative to the surface 1143 of adjacent tooth 1140a3ii generally complements a shape of the notched-out areas, such as area 1125 (FIG. 47A), between adjacent teeth 1140a3i and 1140a3ii. For example, the shape of detent 1122b defined by surfaces, such as surfaces 1122b2 and 1122b3 complements the shape defined by the surfaces 1141 and 1143 shown in FIG. 47A, thereby providing a ratchet and pawl latch.

As illustrated in FIG. 47A, notice that the integral lock, resilient detent or flexible finger 1120 has the detent portion 1120b having a locking edge 1120c. Likewise detent 1122 has the detent 1122b and locking edge 1122c. As mentioned earlier, the ends of the plurality of resilient detents or flexible fingers, such as fingers 1120 and 1122, are resiliently biased toward their respective openings 1102 and 1104, respectively, as illustrated in FIG. 45. Notice that in embodiment of FIGS. 47A-47C and as mentioned earlier, the detent portions 1120b and 1122b are adapted and configured to complement the shape of the ratchet area, such as area 1125 (FIG. 47A). In that embodiment, a one-way stop or latch permits their respective screws 1140 from rotating in one direction, but not in an opposite direction. In the illustration shown, rotational movement of screw 1140 is restricted in a counter-clockwise direction, but movement is permitted in a clockwise direction. Of course, the detents 1120 and 1122 could be adapted for use with left-handed threads so that rotational movement is permitted in a counter-clockwise direction, but not in a clockwise direction. Notice also in this regard that the detent 1120b has surface 1120b2 that is beveled and engages surface 1141 teeth 11403i of the ratchet 1140a. The detent 1120b also has a surface 1120d (FIG. 47B) is adapted and shaped to engage and cooperate with the shoulder or ledge 1140a2 to also restrict axial movement of the screw 1140. The parts 1122a, 1122b, 1122b1, 1122b2, 1122b3 and 1122d operate similarly.

Advantageously, in the illustration shown in FIGS. 45, 47A-47C, the plurality of resilient detents or flexible fingers, such as fingers 1120 and 1122, facilitate preventing the screw 1140 from unscrewing and/or withdrawing from the spinal bone by preventing or restricting movement in both a rotational direction about its axis and in an axial direction along its axis. This further facilitates retaining the screw 1140 in the plate 1100 and in its respective spinal bone.

Referring now to FIGS. 46A-46B, another illustrative embodiment is shown comprising a two-way detent. In this regard, notice in FIG. 46B that the detent 1120b comprises a first stop surface 1120b4 and a second stop surface 1120b5. When the detent 1120b is received in a ratchet area, such as area or slot 1145 (FIG. 46B) between the adjacent teeth 1140a3i and 1140a3ii of the ratchet portion 1140a3 of screw head 1140, the detents become situated between the adjacent teeth, such as teeth 1140a3i and 1140a3ii. The surfaces 1120b1 and 1120b2 engage and cooperate with the walls 1141 and 1143, respectively, of the teeth 1140a3i and 1140a3ii, to prevent the screw 1140 from rotating in either a counter-clockwise or clockwise direction. To rotate the screw 1140, the finger 1122 is held open so that the detent 1120b is not received in the area 1145.

As with prior embodiments described earlier herein relative to FIGS. 47A-47C, notice that when the detent portion 1120b is received in a notched-out area, such as area 1145 (FIG. 46B), the surface 1120d engages the shoulder portion 1140a2 to facilitate preventing axial movement of the screw 1140, thereby facilitating preventing the screw 1140 from retreating or moving axially out of the plate 1100 or spinal bone to which it is mounted.

Advantageously, the embodiment illustrated in FIGS. 46A and 46B restricts movement of the screw 1140 in an axial direction along the axis of screw 1140 and rotational movement about its axis.

Referring now to FIGS. 48A-48I, the operation and use of the ratchet and pawl embodiment illustrated in FIGS. 46A-46B, will be described relative to detent 1120, but it should be understood that the embodiment illustrated in FIGS. 47A-47C as well as the other detents in the plate 1100 operate in substantially the same manner, except that as mentioned earlier herein, the embodiment of FIGS. 47A-47C provides a one-way detent, rather than the two-way detent illustrated in FIGS. 46A-46B and 48A-48I.

The screw 1140 is positioned in the aperture 1102 and the plate 1100 situated in operative relationship with the bones to which it will be attached. As the screw 1140 is screwed into the spinal bone 10, the screw 1140 moves or is screwed in a clockwise direction (as viewed in FIG. 48A). As the screw 1140 moves in the direction indicated by arrow F (FIG. 48C), notice that a bottom portion 1140a3 (FIG. 48H) of screw head 1140a engages a surface 1120b6 (FIG. 48F) of the detent portion 1120b of resilient detent or flexible finger 1120, as illustrated in FIGS. 48D and 48E. In the illustration being described, notice in FIGS. 48C, 48F and 48I that the detent portion 1120b is generally L-shaped in cross-section and comprises a first leg portion 1120b7 and a second leg portion 1120b8 (FIG. 48C). As the screw 1140 is rotated and screwed into bone, a shoulder 1140a2 of screw head 1140a engages surface 1120b6 of locking or detent portion 1120b and forces it to move and flex in the direction of arrow G (FIG. 48D). As mentioned earlier, each of the plurality of resilient detents or flexible fingers or locks, including the finger 1120 in plate 1100, is generally biased to a home or locked position, illustrated in FIGS. 45, 48A, 48G, 48H and 48I. If necessary, the detent 1120 is "held open" (as illustrated in phantom FIG. 48G) until the screw 1140 is screwed to or near its final depth, wherever the finger 1120 is urges, resiliently moves or is released and the detent 1120b can be received in one of the areas or slots 1145 (FIG. 46B) in the head ratchet 1140a.

It should be understood that as the screw 1140 moves further into aperture 1102, the finger 1120 is caused to flex or move away from its home position, as illustrated in FIG. 48D. In this regard, notice that the camming portion 1140a1 of screw head 1140a defines or provides a rounded engaging or camming surface that acts against, urges or engages the flexible finger 1120 and forces it to move in the direction of arrow G in FIG. 48D.

After the portion or surface 1120d1 of leg 1120b7 clears the shoulder 1140a2 of the screw head 1140a, as illustrated in FIGS. 48G, 48H and 48I, the generally planar portion or surface 1120d of detent portion 1120b flexes, moves or returns in a direction opposite arrow G (FIG. 48D) and toward the home position at which time the surface 1120b1 (FIG. 48I) comes into proximity with or engages the ratchet portion 1140a3 of screw head 1140a.

A bottom surface 1120b7 (FIG. 48I) becomes operatively associated with and opposed to the shoulder 1140a2, as illustrated, for example, in FIGS. 48H and 48I. Notice that the dimension SD1 (FIG. 48F), which corresponds to a width of the shoulder 1140a2, is generally smaller to a dimension DD1 (FIG. 48F), which is a cross-sectional width of a portion of the detent portion 112b7, but about the same dimension as the dimension DD2 (FIG. 48D).

Thus, as the plurality of resilient detents or flexible fingers, such as finger 1120, clears the shoulder portion 1140a2 of the ratchet 1140a3 to lock the screw 1140 and prevent it from rotating in at least one direction (for the embodiment illustrated in FIGS. 47A-47C) or in both clockwise and counter-clockwise directions for the embodiment illustrated in FIGS. 46A-46B and 48A-48I.

After the resilient detent or flexible finger 1120 moves, flexes or returns to the home position illustrated in FIGS. 48A and 48B, the surface 1120d1 of portion 1120b "clears" the shoulder 1140a2 and becomes operatively related and generally opposed to the shoulder 1140a2 as shown. The detent 1120b finds and becomes biased in the ratchet area or slot, such as area or slot 1145 (FIG. 48A), whereupon the screw 1140 becomes locked to the plate or cover 1100. The screw 1140 becomes locked in the plate 1100 and spinal bone, such as spinal bone 10, so that it is restricted from rotational movement in an axial direction. The other fingers or detents in the embodiments of FIGS. 45-48I operate in a similar manner.

In the embodiment being described and as mentioned earlier, the plurality of resilient detents or flexible fingers 1120-1134 are provided a plurality of pairs, 1120, 1122; 1124, 1126; 1128,1130; and 1132, 1134 as shown in FIG. 45. In the illustration being described relative to FIG. 45 and FIGS. 48A-48I, each of the plurality of the resilient detents or flexible fingers making up the pairs is associated with at least one of the plurality of apertures 1102-1116, respectively as shown.

As with the embodiment described earlier herein relative to the plate or cover 500, the embodiment illustrated in FIGS. 45-48I may comprise a plurality of windows or window areas 1121, 1123 and 1125 mentioned earlier. Note that each of the plurality of windows 1121, 1123, 1125 are defined or bounded at least in part by at least one or a plurality of the resilient detents or flexible fingers 1120-1134 in the illustration being shown. For example, one or more of the window areas 1121, 1123 and 1125 may be bounded by and in communication with the integral portion 1120a and the joining portion 1120c of the one or more resilient detents or flexible fingers 1120-1134. Thus, as illustrated in FIG. 48A, notice that the area or window area 1121 is bounded or defined at least in part by a plurality of walls similar to embodiments illustrated and described earlier herein relative to plate 500 shown in FIG. 38A. As with the prior embodiments, one advantage or feature of the windows, such as the window area 1121, is that is permits easy access and visualization to the associated graft area, such as area 28.

Similar to the prior embodiments described earlier herein, it should be understood that the plate 1100 may be provided with less or more apertures in the associated resilient detents or fingers and may have one or more of the other illustrative features in FIGS. 40A-44D relative to the embodiment described earlier. Thus, more or fewer apertures and/or pairs of apertures and windows or window areas may be provided as similar to the embodiments illustrated in FIGS. 44A-44D. As with the prior embodiments, note that each of the screw-receiving areas or apertures and associated resilient detents or flexible fingers, such as aperture 1102 and detent 1120 in FIG. 45, is in communication with at least one window. For example, note that window 1121 in FIG. 45 is in communication with the screw-receiving apertures or areas 1102 and 1104. Note that the bottom window 1125 in FIG. 45 is in communication with the bottom pair of screw-receiving apertures 1114 and 1116.

In the illustration being described, the plate or cover 1100 may be curved or crowned similar to the plate or cover 1100, along its length and/or its width to conform or complement the shape of the spinal bones 10-16. Notice that a front side 1100d of plate 1100 may be generally smooth and have a curved or beveled edge similar to the embodiment described earlier herein relative to FIG. 38C. A back or rear side 1100e may comprise serrated areas, similar to the serrated areas 1149, that facilitate retaining the plate or cover 1100 in a secure position against the spinal bones 10-18.

Referring now to FIGS. 49-57, various other illustrations or embodiments are illustrated. In these embodiments, various ways for preventing axial and/or rotational movement of a screw is shown. For example, FIGS. 49-53I illustrate an embodiment that restricts both rotational movement and axial withdrawal movement of a screw 2000. While typical withdraw of a screw from bone is a result of the screw rotating counterclockwise, in some circumstances the screw may withdraw from the bone by moving axially and without any rotational movement of the screw 2000. The terms "axial movement" refer to the screw moving generally along or generally parallel to its axis and withdrawing from the bone in which it is screwed.

Figure 50:
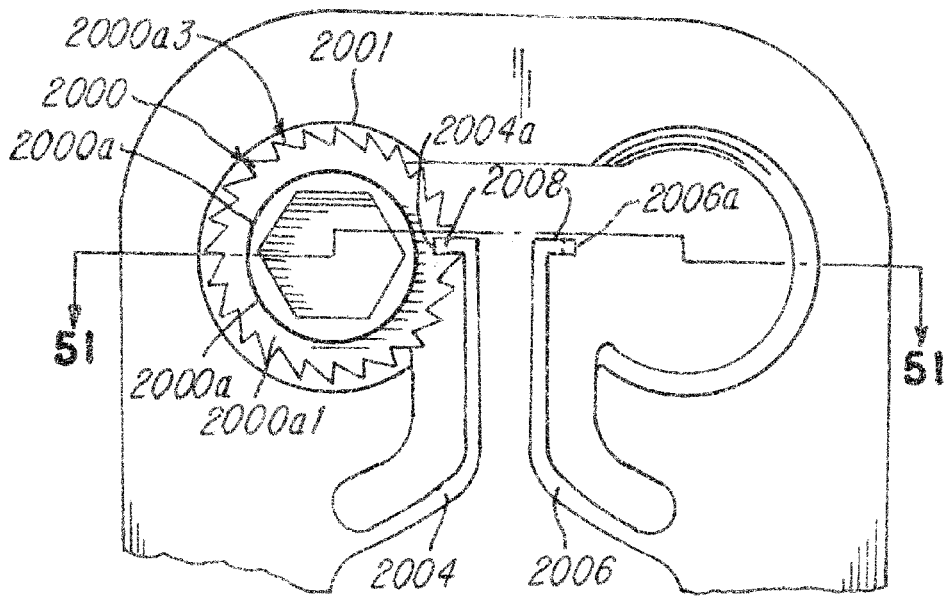
FIG. 50 is a fragmentary view showing features of the embodiment shown in FIG. 49.
Figure 51:
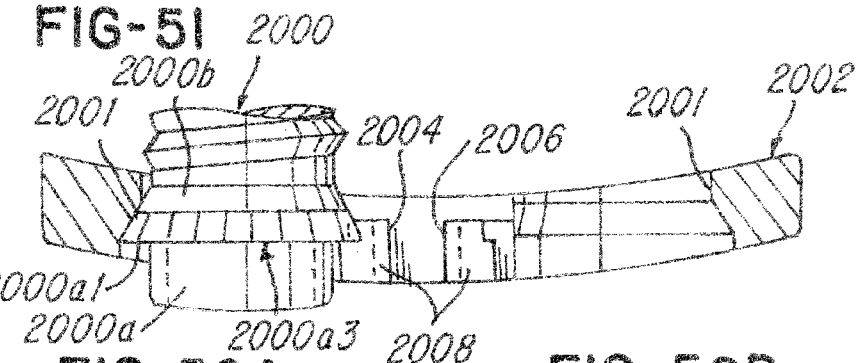
FIG. 51 is a view, taken along the line 51 in FIG. 50.
Figures 52A, 52B:
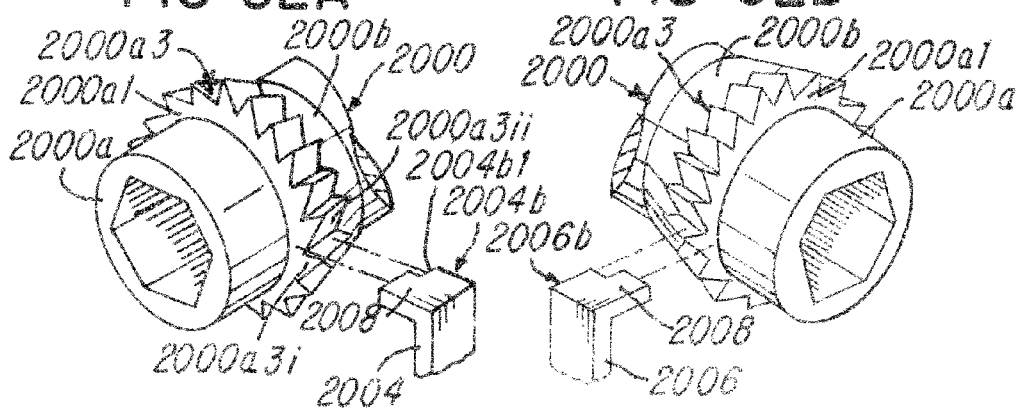
FIGS. 52A-52D are various fragmentary views illustrating further details of the embodiment shown in FIG. 49.
Figure 52C:
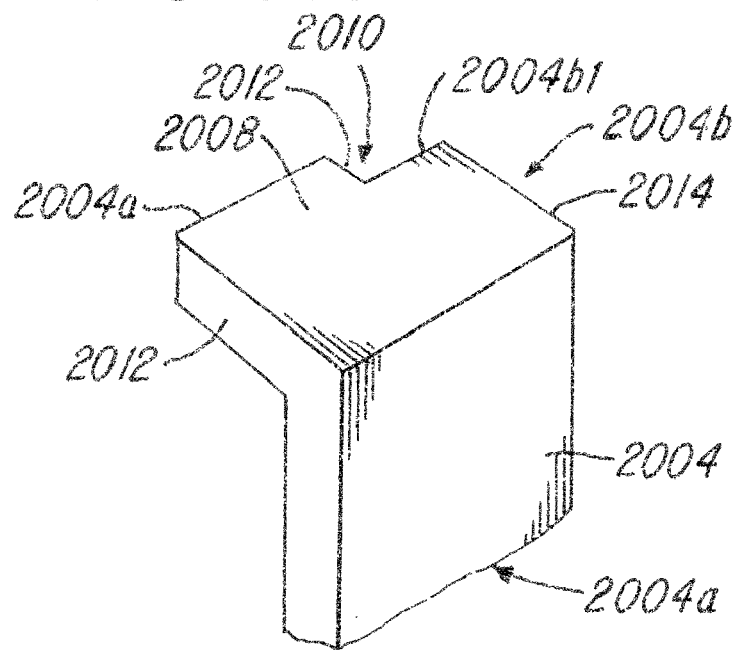
Figure 52D:
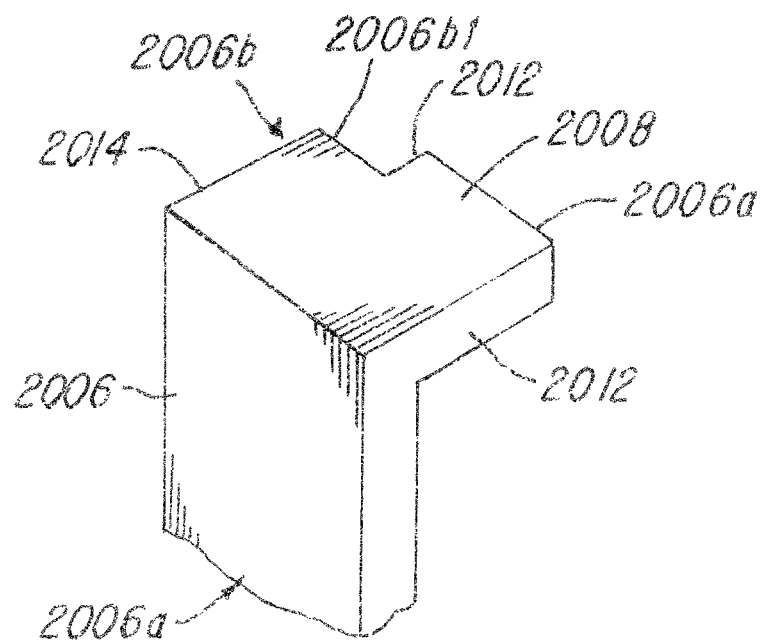

FIGS. 49-53I illustrate another embodiment wherein a plate 2002 comprises at least one or a plurality of apertures, such as aperture 2001, for receiving a screw 2000 having a screw head 2000a. The plate 2002 comprises at least one resilient finger, arm or pawl, such as fingers 2004, 2006 (FIG. 50). For ease of description, features of arm 2004 will be described, but it should be understood that the other fingers, arms or pawls are constructed similarly and perform in substantially the same manner. The resilient pawl, such as pawl 2004, provides a pawl or detent 2004a (FIGS. 50-52B) adapted to cooperate with a ratchet portion 2000a3 and the teeth 2000a3i and 2000a3ii on a head 2000a of screw 2000. The ratchet portion 2000a3 is integral with a camming portion 2000b of screw 2000, as best illustrated in FIGS. 52A-52D.

Similar to the embodiment described earlier herein relative to FIGS. 47A-47C, note that the resilient fingers or pawls 2004 and 2006 are resilient, elastic and deflectable. The detent 2004b having a locking edge 2004b1 for providing a one-way stop or latch similar to the embodiment shown earlier herein relative to FIGS. 47A-47C. Notice in this embodiment that pawls 2004 and 2006 comprises detent 2004b (FIG. 52A) and detent 2006b (FIG. 52B), respectively, and each comprises a portion 2008 (FIG. 52B) having a notched-out area 2010 (FIG. 52C) that defines a first portion 2012 and a second portion 2014 as shown. In this embodiment, the first portion 2012 of pawl 2004 comprises an edge 2004a (FIG. 52A) that cooperates with the teeth 2000a3i and 2000a3ii of the ratchet 2000a3 on screw head 2000a to provide a ratchet and pawl stop or lock. Notice also that an edge or surface 2012a of portion 2012 cooperates with a surface 2000ai (FIGS. 52A-52B) of screw head 2000a to provide an axial movement preventer or stop, as illustrated in FIGS. 51 and 53G-53I. It should be understood that the other fingers, arms or pawls in plate 2002 are constructed similarly.

FIGS. 53A-53C illustrate the resilient arm 2004 yielding to the axial movement of the screw 2000 after the screw 2000 has been received in aperture 2001 (FIG. 49) of plate 2002 and the screw 2000 is screwed into the bone. Notice in FIGS. 53C that a corner or edge 2004a (FIG. 53C) engages a camming portion 2000b of screw 2000 as the screw 2000 is screwed into the bone, which causes the arm 2004 to yield or move away from an axis of screw 2000.

As screw 2000 is screwed into bone, the arm 2004 yields or moves away from the screw axis, as shown in FIGS. 53D-53F. When the edge 2012a (FIGS. 51 and 53I) clears or passes the surface 2000a1 of the ratchet portion 2000a3, as illustrated in FIGS. 53G-53I, then the edge 2006a cooperates with the ratchet portion 2000a3 and the surface 2000a1 to engage the teeth 2000a3i and 2000a3ii of the ratchet 2000a3. Substantially simultaneously, the surface 2012a becomes operatively associated with and generally opposed to the surface 2000a1, as best shown in FIG. 53I, to lock the screw 2000 in the plate 2002. Thus, in this embodiment, similar to the embodiment illustrated in FIGS. 47A-47C, the ratchet and pawl arrangement prevents both axial movement and rotational movement of the screw 2000.

FIGS. 54-57 illustrate another embodiment wherein no axial stop or movement prevention is provided. In this embodiment, notice that a plate 3000 comprises an aperture 3002 comprising at least one or a plurality of resilient fingers or pawls 3004 and 3006 adapted to define a pawl or detent. The pawl 3004 does not have a notched-out area like area 2010 shown in arm 2004 in FIG. 51. In this embodiment, the resilient fingers or pawls, such as fingers 3004 and 3006 have an L-shaped end or pawl 3004a and 3006a, respectively as shown in FIGS. 56-57. The ends 3004a and 3006a have a detent 3004ai and 3006ai, respectively, which cooperate with teeth 2000a3i and 2000a3ii of the ratchet 2000a3 in order to lock the screw 2000 and prevent rotational movement thereof. Notice in FIG. 55 that the end 3004a cooperates with tooth 2000a3i of the ratchet, but that no portion of the detent or end 3004a extends over the surface 2000a1, so no axial movement stop of the type shown in FIGS. 49-53I is provided.

Although not shown, the ratchet portion 2000a3 in the illustrative embodiments of FIGS. 49-57 is shown as a one-way stop, but could be a two-way stop if desired.

Advantageously, various embodiments described relative to FIGS. 49-57 provide various means, apparatus and methods for preventing axial and/or rotational movement of the screw and for providing an integral lock to facilitate retaining the screw in a bone, such as a spinal bone. As with prior embodiments, the system and method according to these embodiments show various means for providing a lock for retaining the screw in the plate in which it is received.

Advantageously, the embodiments illustrated in FIGS. 45-48I may be provided for use with a single screw 1140 and single aperture to secure the plate or cover 1100 to each of the spinal bones, rather than a plurality of screws that secure the plate or cover 1100 to the spinal bone. It should be understood, however, that having at least one integral lock, resilient detent or flexible finger is also desired. Again, it should be understood that more or fewer windows, such as windows 1121, 1123 and 1125, may be provided and in fact the plate 1100 could be provided with no windows.

Advantageously, the embodiments illustrated in FIGS. 45-48I also prevent rotational movement of the screw 1140 and at least one of a clockwise or counter-clockwise direction. As with the embodiment described earlier herein, the plate 1100 also comprises a second wall 1142 having a smaller diameter than the wall 1146. The second wall 1142 also terminates at the opening 1147 and provides a shoulder 1144 that defines a seat that engages and supports a bottom portion 1140a3 of screw head 1140a. Notice that in the illustration shown in FIGS. 45-48I, it is contemplated that at least one screw 1140 be received in each of the screw-receiving apertures, such as aperture 1102, but the plate 1100 and aperture 1102 may be adapted to accommodate a plurality of screws if desired.

The embodiment of FIGS. 45-48I may be made from the same materials as mentioned earlier relative to the other plates, and it may be a one-piece integral construction, or multiple pieces. The plate may be made from multiple materials or a single material.

Advantageously, the system and method provide means and apparatus for locking a screw to a plate and preventing withdrawal of the screw or unscrewing of the screw. The illustrative embodiments provide means and apparatus for facilitating preventing rotational movement of at least one or a plurality of screws in at least one or a plurality of directions and axial movement of the at least one or a plurality of screws.

Moreover, features of the embodiments shown, however, may be used with one or more of the embodiments described in the related applications U.S. patent application Ser. No. 10/675,361, now issued as U.S. Pat. No. 7,182,782; U.S. patent application Ser. No. 10/858,629, published as U.S. Patent Publication No. 2005/0071008; and Ser. No. 11/193, 523, published as U.S. Patent Publication No. 2007/0043357, the specifications of which are incorporated herein by reference and made a part hereof.

While the apparatus and method described constitute preferred embodiments of this invention, it is to be understood that the invention is not limited to this precise apparatus and method, and that changes may be made in either without departing from the scope of the invention, which is defined in the appended claims.

What is claimed is:

1. An implant plate system comprising:
   at least one screw;
   a one-piece integral plate member having a plurality of apertures, each of said plurality of apertures being capable of receiving said at least one screw; and
   a plurality of resilient stop members defined by at least one cut-out portion, channel or area, each of said plurality of resilient stop members having a first end monolithically and integrally formed in said one-piece integral plate member and a resilient portion operatively associated with at least one of said plurality of apertures,
   said at least one screw comprising a head having a generally radial first surface and a second surface that is generally parallel to an axis of said at least one screw, said generally radial first surface and said second surface being integral and monolithically formed in said at least one screw, said second surface having a receiving area;
   said resilient portion having a first portion and a second portion both of which are monolithic and integral with said resilient portion, said first portion and said second portion cooperating with said generally radial first surface and said second surface, respectively, of said at least one screw to facilitate preventing said at least one screw from moving in a rotational direction and an axial direction;
   said first portion of each of said plurality of resilient stop members becoming associated with said generally radial first surface to provide an axial movement preventer or stop and said second portion being received in said receiving area of said second surface to prevent rotational movement of said at least one screw in at least one direction.

2. The implant plate system as recited in claim 1 wherein each of said plurality of resilient stop members define a one-way lock preventing rotation in one direction.

3. The implant plate system as recited in claim 1 wherein each of said plurality of resilient stop members comprises a pawl that is adapted to define both said first portion and said second portion to prevent both axial movement of said at least one screw and rotational movement of said at least one screw.

4. The implant plate system as recited in claim 3 wherein said receiving area defines a ratchet, said pawl and ratchet cooperate to provide at least one of a one-way pawl or a two-way pawl.

5. The implant plate system as recited in claim 3 wherein said receiving area defines a ratchet, said pawl and ratchet cooperate to provide a one-way stop and axial stop.

6. The implant plate system as recited in claim 1 wherein said head has a plurality of notched-out areas for receiving at least a portion of at least one of said plurality of resilient stop members.

7. The implant plate system as recited in claim 1 wherein said second surface defines a wall, each of said first and second portions of said plurality of resilient stop members is defined by a detent portion that follows or engages a wall of said head of said at least one screw after it is screwed into a spinal bone.

8. The implant plate system as recited in claim 1 wherein each of said plurality of resilient stop members comprises an end that is generally L-shaped in cross-section to define said first and second portions.

9. The implant plate system as recited in claim 1 wherein said plurality of resilient stop members each comprise an arcuate portion that defines said resilient portion.

10. The implant plate system as recited in claim 9 wherein said resilient portion is generally L-shaped in cross-section.

11. The implant plate system as recited in claim 1 wherein said plate member comprises at least one window area.

12. The implant plate system as recited in claim 1 wherein said plate member comprises said first end, a second end and a joining portion joining said first and second ends; said implant plate further comprising:
   a first pair of said plurality of apertures located toward said first end of said plate member;
   a first pair of said plurality of resilient stop members extending from said plate member and toward said first pair of said plurality of apertures, respectively, such that their ends become situated in said first pair of said plurality of apertures.

13. The implant plate system as recited in claim 12 wherein said joining portion comprises an arcuate shape.

14. The implant plate system as recited in claim 12 wherein said first pair of said plurality of resilient stop members are situated adjacent each other.

15. The implant plate system as recited in claim 1 wherein each of said plurality of resilient stop members comprises an arcuate portion.

16. The implant plate system as recited in claim 1 wherein said plate comprises at least one window in communication with each of said plurality of apertures.

17. The implant plate system as recited in claim 16 wherein said at least one window is bounded at least in part by at least one of said plurality of resilient stop members.

18. The implant plate system as recited in claim 1 wherein each of said plurality of resilient stop members comprises a curved portion and a detent portion, said detent portion being situated in operative relation to said at least one screw after it is received in one of said plurality of apertures.

19. The implant plate system as recited in claim 1 wherein said plurality of apertures and said plurality of resilient stop members are arranged and adapted such that at least two screws can be used for each spinal bone.

20. The implant plate system as recited in claim 1 wherein said plurality of apertures and said plurality of resilient stop members are arranged and adapted such that a single screw is used for each spinal bone.

21. An implant plate system comprising:
a plurality of screws:
an integral plate member having a plurality of screw-receiving apertures for receiving said plurality of screws; and
a plurality of locks defined by at least one cut-out portion, channel or area, each of said plurality of locks having a first end monolithically and integrally formed in said integral plate member for preventing migration of said plurality of screws situated in said plurality of screw-receiving apertures, respectively, said plurality of locks being adapted to facilitate preventing axial and rotational movement of said plurality of screws, respectively;
each of said plurality of screws comprising a head having a generally radial first surface and a second surface that is generally parallel to a screw axis, said generally radial first surface and said second surface being integral and monolithically formed in each of said plurality of screws and said second surface having a receiving area;
each of said plurality of locks having a resilient portion having a first portion and a second portion both of which are monolithic and integral with said resilient portion, said first portion and said second portion cooperating with said generally radial first surface and said second surface, respectively, of said plurality of screws to facilitate preventing said plurality of screws from moving in a rotational direction and an axial direction;
said first portion of each of said plurality of locks becoming associated with said generally radial first surface to provide an axial movement preventer or stop and said second portion being received in said receiving area of said second surface to prevent rotational movement of said plurality of screws in at least one direction.

22. The implant plate system as recited in claim 21 wherein at least one of said plurality of locks provides a one-way detent.

23. The implant plate system as recited in claim 21 wherein at least one of said plurality of locks comprises a resilient and elastic pawl that is normally biased into at least one of said plurality of screw-receiving apertures.

24. The implant plate system as recited in claim 23 wherein said pawl comprises at least one of a one-way pawl or two-way pawl for cooperating with a ratchet integral with a screw head.

25. The implant plate system as recited in claim 21 wherein each of said plurality of screws comprises a head having a plurality of notched-out areas for receiving an engaging end of at least one of said plurality of locks.

26. The implant plate system as recited in claim 21 wherein each of said plurality of locks is elastic and becomes resiliently biased away from a screw axis of one of said plurality of screws as it is being screwed into a spinal bone.

27. The implant plate system as recited in claim 21 wherein said plate member and said plurality of locks are a one-piece, integral construction, said plate member comprising a window area, at least one of said plurality of locks yielding toward and into said window area in response to a screw is being screwed into a spinal bone.

28. The implant plate system as recited in claim 21 wherein said plurality of locks comprise a joining portion integrally formed in said plate member and a generally arcuate portion.

29. A prosthetic implant plate comprising:
at least one screw:
an integral plate having a plurality of apertures, each of said plurality of apertures being capable of receiving said at least one screw;
a lock for preventing rotational movement and axial movement of said at least one screw after said at least one screw is received in said integral plate and screwed into a spinal bone;
said lock comprising a resilient stop member defined by at least one cut-out portion, channel or area, said resilient stop member having a first end monolithically and integrally formed in said integral plate and a resilient portion operatively associated with an aperture in said integral plate;
said at least one screw comprising a head having a generally radial first surface and a second surface that is generally parallel to an axis of said at least one screw, said generally radial first surface and said second surface being integral and monolithically formed in said screw, said second surface having a receiving area;
said resilient portion having a first portion and a second portion both of which are monolithic and integral with said resilient portion, said first portion and said second portion cooperating with both said generally radial first surface and said second surface, respectively, of said at least one screw to facilitate preventing said at least one screw from moving in a rotational direction and an axial direction;
said first portion of said resilient stop member becoming associated with said generally radial first surface to provide an axial movement preventer or stop and said second portion being received in said receiving area of said second surface to prevent rotational movement in at least one direction.

30. The prosthetic implant plate as recited in claim 29 wherein said lock comprises a pawl having an end that is generally L-shaped and that defines said portion and said second portion.

31. The prosthetic implant plate as recited in claim 30 wherein said pawl comprises a one-way detent.

32. The prosthetic implant plate as recited in claim 29 wherein said at least one screw comprises a head adapted to define a ratchet.

33. The prosthetic implant plate as recited in claim 29 wherein said lock defines a resilient or elastic curved member integral with said plate; said curved member having an end that engages or covers at least a portion of a top surface of a head of said at least one screw.

34. The prosthetic implant plate as recited in claim 33 wherein said end comprises a one-way pawl and said head comprises teeth adapted to cooperate with said one-way pawl to provide said lock.

35. The prosthetic implant plate as recited in claim 34 wherein said plate is titanium, titanium alloy, carbon fiber, polymer or other biocompatible material.

36. A one-piece integral implant plate comprising:
a screw;
at least one aperture;
at least one integral lock integral with said plate and having an end associated with said at least one aperture for facilitating preventing a screw received in said at least one aperture from rotating in at least one of a clockwise or counterclockwise direction; said at least one integral lock being resilient and normally biased into said at least one aperture;
a resilient stop member defined by at least one cut-out portion, channel or area, said resilient stop member having a first end monolithically and integrally formed in said integral plate and a resilient portion operatively associated with said at least one aperture;
said screw comprising a head having a generally radial first surface and a second surface that is generally parallel to an axis of said screw, said generally radial first surface and said second surface being integral and monolithically formed in said screw, said second surface having a receiving area;
said resilient portion having a first portion and a second portion both of which are monolithic and integral with said resilient portion, said first portion and said second portion cooperating with said generally radial first surface and said second surface, respectively, of said screw to facilitate preventing said screw from moving in a rotational direction and an axial direction;
said first portion of said resilient stop member becoming associated with said generally radial first surface to provide an axial movement preventer or stop and said second portion being received in said receiving area of said second surface to prevent rotational movement of said screw in at least one direction.

37. The implant plate as recited in claim 36 wherein said at least one integral lock comprises a one-way detent.

38. The implant plate as recited in claim 36 wherein said screw comprises a head having a plurality of notched-out areas for receiving an end of said at least one integral lock.

39. The implant plate as recited in claim 36 wherein said at least one integral lock comprises a detent portion that follows or engages a wall of a head of said screw after it is screwed into a spinal bone.

40. The implant plate as recited in claim 36 wherein said at least one integral lock comprises a detent and a flexible or resilient portion that permits said detent to flex or move toward and away from said at least one aperture.

41. The implant plate as recited in claim 36 wherein said screw has a ratchet; said ratchet being engaged by an end of said at least one integral lock.

42. An implant plate system comprising:
at least one screw:
a plate member having a plurality of screw-receiving areas, each of said plurality of screw-receiving areas being capable of receiving said at least one screw; and
a plurality of locking fingers associated with said plurality of screw-receiving areas, respectively, each of said plurality of locking fingers being resilient adapted to prevent axial movement of a screw and having an end that is normally biased into at least one of said plurality of screw-receiving areas and urges itself against said screw after said screw is received in one of said plurality of screw-receiving areas;
a plurality of apertures, each of said plurality of apertures being capable of receiving said screw;
said plurality of locking fingers defined by at least one cut-out portion, channel or area, each of said plurality of locking fingers having a first end monolithically and integrally formed in said plate member and a resilient portion operatively associated with at one of said plurality of apertures, respectively;
said at least one screw comprising a head having a generally radial first surface and a second surface that is generally parallel to an axis of said at least one screw, said generally radial first surface and said second surface being integral and monolithically formed in said screw, said second surface having a receiving area;
said resilient portion having a first portion and a second portion both of which are monolithic and integral with said resilient portion. said first portion and said second portion cooperating with said generally radial first surface and said second surface, respectively, of said screw to facilitate preventing said screw from moving in a rotational direction and an axial direction;
said first portion of each of said plurality of locking fingers becoming associated with said generally radial first surface to provide an axial movement preventer or stop and said second portion being received in said receiving area of said second surface to prevent rotational movement of said screw in at least one direction.

43. The implant plate as recited in claim 42 wherein each of said plurality of locking fingers comprises a generally arcuate member having an end that engages said screw.

44. The implant plate as recited in claim 42 wherein said screw comprises a head having a plurality of notched-out areas for receiving at least one of said plurality of locking fingers.

45. The implant plate as recited in claim 44 wherein each of said plurality of locking fingers comprises a curved or arcuate portion that is resilient and adapted to cause an end of said plurality of locking fingers to be urged into one of said plurality of notched-out areas.

46. The implant plate as recited in claim 42 wherein a plurality of said plurality of locking fingers are integrally formed in said plate member.

47. The implant plate as recited in claim 42 wherein each of said plurality of locking fingers comprises a locking pawl for engaging a head of said screw and causing said screw to be retained in an axially and rotatably locked position.

48. The implant plate as recited in claim 42 wherein said plurality of locking fingers each comprise a curved portion between a first portion which is integrally connected to said plate member and a detent portion, said detent portion being adapted to prevent axial or rotational movement of the screw and said curved portion urging said detent portion against said screw after said screw is inserted into a screw-receiving area and without the use of any tool.

49. The implant plate as recited in claim 42 wherein each of said plurality of locking fingers moves toward and away from said plurality of screw-receiving areas.

50. The implant plate as recited in claim 42 wherein said plate member comprises at least one window area.

51. The implant plate as recited in claim 50 wherein said plate member is titanium, titanium alloy, carbon fiber, polymer or other biocompatible material.

52. An implant system comprising:
a plate member having a plurality of screw-receiving openings;
a plurality of detents integral with said plate member and having a detent portion in communication with said plurality of screw-receiving openings, respectively;
a plurality of screws for situating into said plurality of screw-receiving openings, respectively;

each of said plurality of screws being adapted to cooperate with at least one of said plurality of detents, respectively, and be retained by said plate member by said plurality of detents such that each of said plurality of screws are restricted from moving in both an axial direction and a rotational direction;

a plurality of apertures, each of said plurality of apertures being capable of receiving at least one screw;

said plurality of detents defined by at least one cut-out portion, channel or area and each of said plurality of detents having a first end monolithically and integrally formed in said plate member and a resilient portion operatively associated with at one of said plurality of apertures, respectively;

each of said plurality of screws comprising a screw head having a generally radial first surface and a second surface that is generally parallel to a screw axis, said generally radial first surface and said second surface being integral and monolithically formed in said plurality of screws, said second surface having a receiving area;

said resilient portion having a first portion and a second portion both of which are monolithic and integral with said resilient portion. said first portion and said second portion cooperating with said generally radial first surface and said second surface, respectively, of said plurality of screws to facilitate preventing said plurality of screws from moving in a rotational direction and an axial direction;

said first portion of each of said plurality of detents becoming associated with said generally radial first surface to provide an axial movement preventer or stop and said second portion being received in said receiving area of said second surface to prevent rotational movement of said plurality of screws in at least one direction.

53. The implant system as recited in claim 52 wherein each of said plurality of detents comprise a one-way detent and said screw head comprises a ratchet.

54. The implant system as recited in claim 52 wherein each of said plurality of detents comprises a first portion that is integrally connected with said plate member, an engaging portion and a flexible or resilient portion joining said first portion and said engaging portion.

55. The implant system as recited in claim 54 wherein each of said plurality of screws comprises a ratchet portion having teeth and a shoulder portion lying in a plane that is generally radial relative to said axis.

56. The implant system as recited in claim 55 wherein each of said plurality of screws further comprises a camming portion, said camming portion causing at least one of said plurality of detents to flex away or be urged from its associated screw-receiving area and said shoulder portion engaging said at least one of said plurality of detents and retaining said at least one screw in a substantially locked position.

57. The implant system as recited in claim 52 wherein said detent portion is generally L-shaped in cross-section, at least one leg of said L-shape becoming generally opposed to a shoulder surface on said at least one screw.

58. The implant system as recited in claim 52 wherein a first pair of said plurality of detents are adjacent each other with a window area between them.

59. A plate system comprising:
a screw having a screw head;
a plate having an aperture for receiving said screw head and a window area;
at least one pawl for restricting or preventing said screw from moving in at least one of an axial direction or a rotational direction and said at least one pawl being urged into said window area in response to a screw being received in said aperture;
said at least one pawl defined by at least one cut-out portion, channel or area, each of said at least one pawl having a first end monolithically and integrally formed in said plate and having a resilient portion operatively associated with said aperture;
said screw head having a generally radial first surface and a second surface that is generally parallel to an axis of said screw, said generally radial first surface and said second surface being integral and monolithically formed in said screw, said second surface having a receiving area;
said resilient portion having a first portion and a second portion both of which are monolithic and integral with said resilient portion, said first portion and said second portion cooperating with both said generally radial first surface and said second surface, respectively, of said screw facilitate preventing said screw from moving in a rotational direction and an axial direction;
said first portion of said at least one pawl becoming associated with said generally radial first surface to provide an axial movement preventer or stop and said second portion being received in said receiving area of said second surface to prevent rotational movement of said screw in at least one direction.

60. The plate system as recited in claim 59 wherein said at least one pawl is integral with said plate.

61. The plate system as recited in claim 60 wherein said screw head is adapted to provide a ratchet that cooperates with said at least one pawl to restrict or prevent said screw from moving said at least one of an axial direction or a rotational direction 62. The plate system as recited in claim 60 wherein said at least one pawl is generally arcuate.

63. The plate system as recited in claim 60 wherein said at least one pawl is integral with said plate, said screw head comprising a ratchet for cooperating with said at least on pawl to prevent said rotational movement.

64. The plate system as recited in claim 59 wherein said at least one pawl prevents movement of said screw in both axial and rotational directions.

65. The plate system as recited in claim 59 wherein said plate comprises a plurality of walls that define a plurality of apertures for receiving a plurality of screws, respectively, said plate further comprising a plurality of pawls operatively associated with said plurality of apertures, respectively, each of said plurality of pawls engaging at least one screw to prevent axial or rotational movement thereof after said at least one screw is received in said aperture.

66. The plate system as recited in claim 65 wherein each of said plurality of pawls is adapted to prevent both axial and rotational movement of said screw.

* * * * *

UNITED STATES PATENT AND TRADEMARK OFFICE
CERTIFICATE OF CORRECTION

| | | |
|---|---|---|
| PATENT NO. | : 8,372,152 B2 | Page 1 of 1 |
| APPLICATION NO. | : 11/778270 | |
| DATED | : February 12, 2013 | |
| INVENTOR(S) | : Kirschman | |

It is certified that error appears in the above-identified patent and that said Letters Patent is hereby corrected as shown below:

In the Specification

Column 18, line 61, delete "11 20a" and insert -- 1120a -- therefor.

Column 19, line 10, delete "lportion" and insert -- portion -- therefor.

Signed and Sealed this
Twenty-ninth Day of September, 2015

Michelle K. Lee
*Director of the United States Patent and Trademark Office*